US009296826B2

(12) United States Patent
Cong et al.

(10) Patent No.: US 9,296,826 B2
(45) Date of Patent: Mar. 29, 2016

(54) ANTIBODIES AND METHODS FOR WNT PATHWAY-RELATED DISEASES

(71) Applicants: Feng Cong, Quincy, MA (US); Huaixiang Hao, Malden, MA (US); Lloyd B. Klickstein, Newton, MA (US); Rou-Fun Kwong, Westford, MA (US); Ann Taylor, Wickford, RI (US); Yang Xie, Quincy, MA (US)

(72) Inventors: Feng Cong, Quincy, MA (US); Huaixiang Hao, Malden, MA (US); Lloyd B. Klickstein, Newton, MA (US); Rou-Fun Kwong, Westford, MA (US); Ann Taylor, Wickford, RI (US); Yang Xie, Quincy, MA (US)

(73) Assignee: NOVARTIS AG, Basel (CH)

( * ) Notice: Subject to any disclaimer, the term of this patent is extended or adjusted under 35 U.S.C. 154(b) by 13 days.

(21) Appl. No.: 14/351,410

(22) PCT Filed: Oct. 12, 2012

(86) PCT No.: PCT/IB2012/055560
§ 371 (c)(1),
(2) Date: Apr. 11, 2014

(87) PCT Pub. No.: WO2013/054307
PCT Pub. Date: Apr. 18, 2013

(65) Prior Publication Data
US 2014/0328859 A1  Nov. 6, 2014

Related U.S. Application Data

(60) Provisional application No. 61/547,209, filed on Oct. 14, 2011.

(51) Int. Cl.
| C07K 16/40 | (2006.01) |
| A61K 39/395 | (2006.01) |
| A61K 38/53 | (2006.01) |
| A61K 45/06 | (2006.01) |
| A61K 31/40 | (2006.01) |
| C12N 9/00 | (2006.01) |

(52) U.S. Cl.
CPC ............... *C07K 16/40* (2013.01); *A61K 31/40* (2013.01); *A61K 38/53* (2013.01); *A61K 39/3955* (2013.01); *A61K 45/06* (2013.01); *C12N 9/93* (2013.01); *C12Y 603/02019* (2013.01)

(58) Field of Classification Search
CPC .................... C07K 16/40; A61K 39/3955
See application file for complete search history.

(56) References Cited

U.S. PATENT DOCUMENTS

| 2005/0069930 A1 | 3/2005 | Nakamura et al. |
| 2009/0047276 A1 | 2/2009 | Moon et al. |
| 2009/0074782 A1 | 3/2009 | Gurney |

FOREIGN PATENT DOCUMENTS

| EP | 1 487 877 B1 | 10/2010 |
| EP | 2 275 544 A2 | 1/2011 |
| EP | 1 513 934 B1 | 3/2011 |
| WO | 2004/032838 A2 | 4/2004 |
| WO | 2006/017318 A2 | 2/2006 |
| WO | 2009/056634 A2 | 5/2009 |
| WO | 2010/016766 A2 | 2/2010 |
| WO | 2011/004379 A1 | 1/2011 |
| WO | 2012/140274 A2 | 10/2012 |
| WO | 2012/168930 A2 | 12/2012 |
| WO | 2013/130364 A1 | 9/2013 |

OTHER PUBLICATIONS

Casset et al. ((2003) BBRC 307, 198-205).*
De Pascalis et al. The Journal of Immunology (2002) 169, 3076-3084.*
Ward et al. (Nature 341:544-546 (1989)).*
Smith-Gill et al. (J. Immunol. 139:4135-4144 (1987)).*
Padlan et al. (PNAS 1989, 86:5938-5942).*
Lamminmaki et al. (JBC 2001,276:36687-36694).*
International Search Report for application No. PCT/IB2012/055560 mailed Aug. 16, 2013.
International Preliminary Report on Patentability for application No. PCT/IB2012/055560 issued Apr. 15, 2014.
Abo et al., Modulating WNT receptor turnover for tissue repair. Nat Biotechnol. Sep. 2012;30(9):835-6.
International Search Report for application No. PCT/US2013/027441 mailed May 14, 2013.
Liu et al., PD-08-11: Targeting porcupine, a critical node for Wnt signalling in cancer. Cancer Research. Dec. 15, 2011;71(24):Supplement 3. Abstract.
MacDonald et al., A finger on the pulse of Wnt receptor signaling. Cell Research. Oct. 2012;22:1410-2.
Hao et al., ZNRF3 promotes Wnt receptor turnover in an R-spondin-sensitive manner. Nature. Apr. 29, 2012;485(7397):195-200.
Koo et al., Tumour suppressor RNF43 is a stem-cell E3 ligase that induces endocytosis of Wnt receptors. Nature. Aug. 30, 2012;488(7413):665-9.
Shinada et al., RNF43 interacts with NEDL1 and regulates p53-mediated transcription. Biochem Biophys Res Commun. Jan. 7, 2011;404(1):143-7.

(Continued)

*Primary Examiner* — Daniel C Gamett
(74) *Attorney, Agent, or Firm* — John Prince

(57) ABSTRACT

The transmembrane E3 ubiquitin ligases ZNRF3 and RNF43 are negative regulators of β-catenin and the Wnt signaling pathway in eukaryotic cells. The activity of ZNRF3 can be modulated by antibody binding to its extracellular domain, thus causing an increase in Wnt signaling. The ZNRF3 antagonizing antibodies can be used to treat diseases with low Wnt signaling, such as short bowel syndrome, osteoporosis, diabetes, neurodegenerative diseases, and mucositis. In addition, the antagonizing antibodies of the invention can be used to enhance Wnt signaling for tissue repair and wound healing.

10 Claims, 12 Drawing Sheets

(56) References Cited

OTHER PUBLICATIONS

Sugiura et al., A cancer-associated Ring finger protein, RNF43, is a ubiquitin ligase that interacts with a nuclear protein, HAP95. Exp Cell Res. Apr. 15, 2008;314(7):1519-28.
Uchida et al., Ring finger protein 43 as a new target for cancer immunotherapy. Clin Cancer Res. Dec. 15, 2004;10(24):8577-86.
Welters et al., Wnt signaling: relevance to beta-cell biology and diabetes. Trends Endocrinol Metab. Dec. 2008;19(10):349-55.
Yagyu et al., A novel oncoprotein RNF43 functions in an autocrine manner in colorectal cancer. Int J Oncol. Nov. 2004;25(5):1343-8.
Casset et al., Biochem. Biophys. Res. Commun. 307: 198-205 (2003).
De Pascalis et al., J. Immunol. 169: 3076-3084 (2002).
Ward et al., Nature 341: 544-546 (1989).
Smith-Gill et al., J. Immunol. 139: 4135-4144 (1987).
Padlan et al., PNAS 86: 5938-5942 (1989).
Lamminmaki et al., J. Biol. Chem. 276: 36687-36694.

* cited by examiner

```
                          SEQUENCE LISTING

<160> NUMBER OF SEQ ID NOS: 162

<210> SEQ ID NO 1
<211> LENGTH: 936
<212> TYPE: PRT
<213> ORGANISM: Homo sapiens

<400> SEQUENCE: 1

Met Arg Pro Arg Ser Gly Gly Arg Pro Gly Ala Thr Gly Arg Arg Arg
1               5                   10                  15

Arg Arg Leu Arg Arg Pro Arg Gly Leu Arg Cys Ser Arg Leu Pro
                20                  25                  30

Pro Pro Pro Pro Leu Pro Leu Leu Leu Gly Leu Leu Leu Ala Ala Ala
                35                  40                  45

Gly Pro Gly Ala Ala Arg Ala Lys Glu Thr Ala Phe Val Glu Val Val
            50                  55                  60

Leu Phe Glu Ser Ser Pro Ser Gly Asp Tyr Thr Thr Tyr Thr Thr Gly
65                  70                  75                  80

Leu Thr Gly Arg Phe Ser Arg Ala Gly Ala Thr Leu Ser Ala Glu Gly
                85                  90                  95

Glu Ile Val Gln Met His Pro Leu Gly Leu Cys Asn Asn Asn Asp Glu
                100                 105                 110

Glu Asp Leu Tyr Glu Tyr Gly Trp Val Gly Val Val Lys Leu Glu Gln
            115                 120                 125

Pro Glu Leu Asp Pro Lys Pro Cys Leu Thr Val Leu Gly Lys Ala Lys
        130                 135                 140

Arg Ala Val Gln Arg Gly Ala Thr Ala Val Ile Phe Asp Val Ser Glu
145                 150                 155                 160

Asn Pro Glu Ala Ile Asp Gln Leu Asn Gln Gly Ser Glu Asp Pro Leu
                165                 170                 175

Lys Arg Pro Val Val Tyr Val Lys Gly Ala Asp Ala Ile Lys Leu Met
                180                 185                 190

Asn Ile Val Asn Lys Gln Lys Val Ala Arg Ala Arg Ile Gln His Arg
            195                 200                 205

Pro Pro Arg Gln Pro Thr Glu Tyr Phe Asp Met Gly Ile Phe Leu Ala
        210                 215                 220

Phe Phe Val Val Val Ser Leu Val Cys Leu Ile Leu Leu Val Lys Ile
225                 230                 235                 240

Lys Leu Lys Gln Arg Arg Ser Gln Asn Ser Met Asn Arg Leu Ala Val
                245                 250                 255

Gln Ala Leu Glu Lys Met Glu Thr Arg Lys Phe Asn Ser Lys Ser Lys
                260                 265                 270

Gly Arg Arg Glu Gly Ser Cys Gly Ala Leu Asp Thr Leu Ser Ser Ser
            275                 280                 285
```

```
Ser Thr Ser Asp Cys Ala Ile Cys Leu Glu Lys Tyr Ile Asp Gly Glu
    290                 295                 300

Glu Leu Arg Val Ile Pro Cys Thr His Arg Phe His Arg Lys Cys Val
305                 310                 315                 320

Asp Pro Trp Leu Leu Gln His His Thr Cys Pro His Cys Arg His Asn
                    325                 330                 335

Ile Ile Glu Gln Lys Gly Asn Pro Ser Ala Val Cys Val Glu Thr Ser
                340                 345                 350

Asn Leu Ser Arg Gly Arg Gln Arg Val Thr Leu Pro Val His Tyr
            355                 360                 365

Pro Gly Arg Val His Arg Thr Asn Ala Ile Pro Ala Tyr Pro Thr Arg
    370                 375                 380

Thr Ser Met Asp Ser His Gly Asn Pro Val Thr Leu Thr Met Asp
385                 390                 395                 400

Arg His Gly Glu Gln Ser Leu Tyr Ser Pro Gln Thr Pro Ala Tyr Ile
                405                 410                 415

Arg Ser Tyr Pro Pro Leu His Leu Asp His Ser Leu Ala Ala His Arg
            420                 425                 430

Cys Gly Leu Glu His Arg Ala Tyr Ser Pro Ala His Pro Phe Arg Arg
        435                 440                 445

Pro Lys Leu Ser Gly Arg Ser Phe Ser Lys Ala Ala Cys Phe Ser Gln
    450                 455                 460

Tyr Glu Thr Met Tyr Gln His Tyr Tyr Phe Gln Gly Leu Ser Tyr Pro
465                 470                 475                 480

Glu Gln Glu Gly Gln Ser Pro Pro Ser Leu Ala Pro Arg Gly Pro Ala
                485                 490                 495

Arg Ala Phe Pro Pro Ser Gly Ser Gly Ser Leu Leu Phe Pro Thr Val
            500                 505                 510

Val His Val Ala Pro Pro Ser His Leu Glu Ser Gly Ser Thr Ser Ser
        515                 520                 525

Phe Ser Cys Tyr His Gly His Arg Ser Val Cys Ser Gly Tyr Leu Ala
530                 535                 540

Asp Cys Pro Gly Ser Asp Ser Ser Ser Ser Ser Ser Gly Gln Cys
545                 550                 555                 560

His Cys Ser Ser Ser Asp Ser Val Val Asp Cys Thr Glu Val Ser Asn
                565                 570                 575

Gln Gly Val Tyr Gly Ser Cys Ser Thr Phe Arg Ser Ser Leu Ser Ser
            580                 585                 590

Asp Tyr Asp Pro Phe Ile Tyr Arg Ser Arg Ser Pro Cys Arg Ala Ser
        595                 600                 605

Glu Ala Gly Gly Ser Gly Ser Ser Gly Arg Gly Pro Ala Leu Cys Phe
610                 615                 620

Glu Gly Ser Pro Pro Glu Glu Leu Pro Ala Val His Ser His Gly
625                 630                 635                 640

Ala Gly Arg Gly Glu Pro Trp Pro Gly Pro Ala Ser Pro Ser Gly Asp
                645                 650                 655

Gln Val Ser Thr Cys Ser Leu Glu Met Asn Tyr Ser Ser Asn Ser Ser
            660                 665                 670

Leu Glu His Arg Gly Pro Asn Ser Ser Thr Ser Glu Val Gly Leu Glu
        675                 680                 685

Ala Ser Pro Gly Ala Ala Pro Asp Leu Arg Arg Thr Trp Lys Gly Gly
    690                 695                 700
```

```
His Glu Leu Pro Ser Cys Ala Cys Cys Cys Glu Pro Gln Pro Ser Pro
705                 710                 715                 720

Ala Gly Pro Ser Ala Gly Ala Gly Ser Ser Thr Leu Phe Leu Gly
        725                 730                 735

Pro His Leu Tyr Glu Gly Ser Gly Pro Ala Gly Gly Glu Pro Gln Ser
                740                 745                 750

Gly Ser Ser Gln Gly Leu Tyr Gly Leu His Pro Asp His Leu Pro Arg
            755                 760                 765

Thr Asp Gly Val Lys Tyr Glu Gly Leu Pro Cys Cys Phe Tyr Glu Glu
770                 775                 780

Lys Gln Val Ala Arg Gly Gly Gly Gly Ser Gly Cys Tyr Thr Glu
785                 790                 795                 800

Asp Tyr Ser Val Ser Val Gln Tyr Thr Leu Thr Glu Glu Pro Pro
                805                 810                 815

Gly Cys Tyr Pro Gly Ala Arg Asp Leu Ser Gln Arg Ile Pro Ile Ile
            820                 825                 830

Pro Glu Asp Val Asp Cys Asp Leu Gly Leu Pro Ser Asp Cys Gln Gly
            835                 840                 845

Thr His Ser Leu Gly Ser Trp Gly Gly Thr Arg Gly Pro Asp Thr Pro
850                 855                 860

Arg Pro His Arg Gly Leu Gly Ala Thr Arg Glu Glu Arg Ala Leu
865                 870                 875                 880

Cys Cys Gln Ala Arg Ala Leu Leu Arg Pro Gly Cys Pro Pro Glu Glu
                885                 890                 895

Ala Gly Ala Val Arg Ala Asn Phe Pro Ser Ala Leu Gln Asp Thr Gln
            900                 905                 910

Glu Ser Ser Thr Thr Ala Thr Glu Ala Ala Gly Pro Arg Ser His Ser
                915                 920                 925

Ala Asp Ser Ser Ser Pro Gly Ala
            930                 935

<210> SEQ ID NO 2
<211> LENGTH: 783
<212> TYPE: PRT
<213> ORGANISM: Homo sapiens

<400> SEQUENCE: 2

Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
                20                  25                  30

Ala Ala Ala Val Glu Ser Glu Arg Ser Ala Glu Gln Lys Ala Ile Ile
            35                  40                  45

Arg Val Ile Pro Leu Lys Met Asp Pro Thr Gly Lys Leu Asn Leu Thr
        50                  55                  60

Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                85                  90                  95

Asp Asn Leu Glu Pro Gly Phe Ile Ser Ile Val Lys Leu Glu Ser Pro
                100                 105                 110

Arg Arg Ala Pro Arg Pro Cys Leu Ser Leu Ala Ser Lys Ala Arg Met
        115                 120                 125

Ala Gly Glu Arg Gly Ala Ser Ala Val Leu Phe Asp Ile Thr Glu Asp
    130                 135                 140
```

```
Arg Ala Ala Ala Glu Gln Leu Gln Gln Pro Leu Gly Leu Thr Trp Pro
145                 150                 155                 160

Val Val Leu Ile Trp Gly Asn Asp Ala Glu Lys Leu Met Glu Phe Val
            165                 170                 175

Tyr Lys Asn Gln Lys Ala His Val Arg Ile Glu Leu Lys Glu Pro Pro
        180                 185                 190

Ala Trp Pro Asp Tyr Asp Val Trp Ile Leu Met Thr Val Val Gly Thr
    195                 200                 205

Ile Phe Val Ile Ile Leu Ala Ser Val Leu Arg Ile Arg Cys Arg Pro
210                 215                 220

Arg His Ser Arg Pro Asp Pro Leu Gln Gln Arg Thr Ala Trp Ala Ile
225                 230                 235                 240

Ser Gln Leu Ala Thr Arg Arg Tyr Gln Ala Ser Cys Arg Gln Ala Arg
            245                 250                 255

Gly Glu Trp Pro Asp Ser Gly Ser Ser Cys Ser Ser Ala Pro Val Cys
                260                 265                 270

Ala Ile Cys Leu Glu Glu Phe Ser Glu Gly Gln Glu Leu Arg Val Ile
        275                 280                 285

Ser Cys Leu His Glu Phe His Arg Asn Cys Val Asp Pro Trp Leu His
    290                 295                 300

Gln His Arg Thr Cys Pro Leu Cys Met Phe Asn Ile Thr Glu Gly Asp
305                 310                 315                 320

Ser Phe Ser Gln Ser Leu Gly Pro Ser Arg Ser Tyr Gln Glu Pro Gly
            325                 330                 335

Arg Arg Leu His Leu Ile Arg Gln His Pro Gly His Ala His Tyr His
                340                 345                 350

Leu Pro Ala Ala Tyr Leu Leu Gly Pro Ser Arg Ser Ala Val Ala Arg
        355                 360                 365

Pro Pro Arg Pro Gly Pro Phe Leu Pro Ser Gln Glu Pro Gly Met Gly
    370                 375                 380

Pro Arg His His Arg Phe Pro Arg Ala Ala His Pro Arg Ala Pro Gly
385                 390                 395                 400

Glu Gln Gln Arg Leu Ala Gly Ala Gln His Pro Tyr Ala Gln Gly Trp
            405                 410                 415

Gly Leu Ser His Leu Gln Ser Thr Ser Gln His Pro Ala Ala Cys Pro
                420                 425                 430

Val Pro Leu Arg Arg Ala Arg Pro Pro Asp Ser Ser Gly Ser Gly Glu
        435                 440                 445

Ser Tyr Cys Thr Glu Arg Ser Gly Tyr Leu Ala Asp Gly Pro Ala Ser
    450                 455                 460

Asp Ser Ser Ser Gly Pro Cys His Gly Ser Ser Ser Asp Ser Val Val
465                 470                 475                 480

Asn Cys Thr Asp Ile Ser Leu Gln Gly Val His Gly Ser Ser Ser Thr
            485                 490                 495

Phe Cys Ser Ser Leu Ser Ser Asp Phe Asp Pro Leu Val Tyr Cys Ser
                500                 505                 510

Pro Lys Gly Asp Pro Gln Arg Val Asp Met Gln Pro Ser Val Thr Ser
        515                 520                 525

Arg Pro Arg Ser Leu Asp Ser Val Val Pro Thr Gly Glu Thr Gln Val
    530                 535                 540

Ser Ser His Val His Tyr His Arg His Arg His His Tyr Lys Lys
545                 550                 555                 560
```

```
Arg Phe Gln Trp His Gly Arg Lys Pro Gly Pro Glu Thr Gly Val Pro
                565                 570                 575
Gln Ser Arg Pro Pro Ile Pro Arg Thr Gln Pro Gln Pro Glu Pro Pro
            580                 585                 590
Ser Pro Asp Gln Gln Val Thr Arg Ser Asn Ser Ala Ala Pro Ser Gly
        595                 600                 605
Arg Leu Ser Asn Pro Gln Cys Pro Arg Ala Leu Pro Glu Pro Ala Pro
    610                 615                 620
Gly Pro Val Asp Ala Ser Ser Ile Cys Pro Ser Thr Ser Ser Leu Phe
625                 630                 635                 640
Asn Leu Gln Lys Ser Ser Leu Ser Ala Arg His Pro Gln Arg Lys Arg
                645                 650                 655
Arg Gly Gly Pro Ser Glu Pro Thr Pro Gly Ser Arg Pro Gln Asp Ala
            660                 665                 670
Thr Val His Pro Ala Cys Gln Ile Phe Pro His Tyr Thr Pro Ser Val
        675                 680                 685
Ala Tyr Pro Trp Ser Pro Glu Ala His Pro Leu Ile Cys Gly Pro Pro
    690                 695                 700
Gly Leu Asp Lys Arg Leu Leu Pro Glu Thr Pro Gly Pro Cys Tyr Ser
705                 710                 715                 720
Asn Ser Gln Pro Val Trp Leu Cys Leu Thr Pro Arg Gln Pro Leu Glu
                725                 730                 735
Pro His Pro Pro Gly Glu Gly Pro Ser Glu Trp Ser Ser Asp Thr Ala
            740                 745                 750
Glu Gly Arg Pro Cys Pro Tyr Pro His Cys Gln Val Leu Ser Ala Gln
        755                 760                 765
Pro Gly Ser Glu Glu Glu Leu Glu Glu Leu Cys Glu Gln Ala Val
    770                 775                 780

<210> SEQ ID NO 3
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Glu Leu Thr Gln Pro Pro Ser Val Ser Val Ser Pro Gly Gln
1               5                   10                  15
Thr Ala Ser Ile Thr Cys Ser Gly Asp Ser Ile Pro Ser Lys Tyr Ala
            20                  25                  30
His Trp Tyr Gln Gln Lys Pro Gly Gln Ala Pro Val Leu Val Ile Tyr
        35                  40                  45
Gly Lys Ser His Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Glu
65                  70                  75                  80
Asp Glu Ala Asp Tyr Tyr Cys Ala Ala Trp Asp Leu Leu Gly Asp Gly
                85                  90                  95
Trp Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
```

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
        210
```

<210> SEQ ID NO 4
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Met His Trp Val Arg Gln Ala Pro Gly Gln Gly Leu Glu Trp Met
        35                  40                  45

Gly Trp Ile Asn Pro Tyr Thr Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Lys Val Tyr Met Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Glu Phe Tyr Lys Asp
    210                 215                 220

Asp Asp Asp Lys Gly Ala Pro His His His His His His
225                 230                 235
```

<210> SEQ ID NO 5
<211> LENGTH: 213
<212> TYPE: PRT
<213> ORGANISM: Artificial Sequence
<220> FEATURE:
<223> OTHER INFORMATION: Description of Artificial Sequence: Synthetic

<400> SEQUENCE: 5

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 6
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Glu
    210                 215                 220

Phe Asp Tyr Lys Asp Asp Asp Asp Lys Gly Ala Pro His His His His
225                 230                 235                 240

His His

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccaguauga gaccaugua                                                    19

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uacauggucu cauacuggga g                                                 21

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gcugcuacac ugaggacua                                                    19

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uaguccucag uguagcagcc g                                                 21

<210> SEQ ID NO 11
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcagaacaga aagcuauua                                                  19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaaggaagga uuaguccaa                                                  19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aggauucacu guaacguua                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuacugaagc gacguguua                                                  19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uguggucacc ugugcagcu                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agcugcacag gugaccaca                                                  19

<210> SEQ ID NO 17
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatggagagg agctgagagt cattc                                        25

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gataactcgc tgttgctgct g                                            21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgggataaca ttcagggta                                               19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccatggcgg taactgtc                                                18

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctccagccac cagtaccaga tc                                           22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggagagtg gaaagtggtt g                                            21

<210> SEQ ID NO 23
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 23
tccacttgtg cagttccaca g                                               21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atctcttcat ggtgcctcag g                                               21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagattggtg ctggatatgc                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actgccttga tgactcctag                                                 20

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatcatggtc tgtataccgg gatcg                                           25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
catactttgg gctcatgagc aagc                                            24

<210> SEQ ID NO 29
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
gcaggtatac attaccacac cc                                                22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctctaacat ccactgccag a                                                 21

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gly Asp Ser Ile Pro Ser Lys Tyr Ala His
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Ile Tyr Gly Lys Ser His Arg Pro Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Trp Asp Leu Leu Gly Asp Gly Trp
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Thr Phe Thr Ser Tyr His Met His
1               5

<210> SEQ ID NO 35
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Asn Pro Tyr Thr Gly Asp Thr Asn Tyr Ala Gln Lys Phe Gln
1               5                   10                  15

Gly Arg

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Val Tyr Met Asp Ile Trp
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gly Asp Ser Leu Gly Ser Tyr Tyr Val His
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Val Ile Tyr Arg Asn Lys Gln Arg Pro Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Thr Tyr Asp Trp Met Tyr Ser Ser Arg
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Phe Thr Phe Ser Asp Tyr Gly Ile His
1               5

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ile Lys Ser Lys Thr Asp Gly Gly Ile Thr Glu Tyr Ala Ala Pro
1               5                   10                  15

Val Lys Gly

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ile Tyr Tyr Leu Glu Ala Phe Asp Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Gly Asp Ser Ile Pro Ser Lys Tyr Ala His
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Lys Ser His Arg Pro Ser
1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ala Trp Asp Leu Leu Gly Asp Gly Trp Val
1               5                   10

<210> SEQ ID NO 46
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Tyr His Met His
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Ile Asn Pro Tyr Thr Gly Asp Thr Asn Tyr Ala Gln Lys Phe Gln
1               5                   10                  15
Gly

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Lys Val Tyr Met Asp Ile
1               5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Gly Asp Ser Leu Gly Ser Tyr Tyr Val His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Asn Lys Gln Arg Pro Ser
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 51

Gln Thr Tyr Asp Trp Met Tyr Ser Ser Arg Val
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Tyr Gly Ile His
1               5

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ile Lys Ser Lys Thr Asp Gly Gly Ile Thr Glu Tyr Ala Ala Pro
1               5                   10                  15

Val Lys Gly

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ile Tyr Tyr Leu Glu Ala Phe Asp Val
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ser Ile Pro Ser Lys Tyr
1               5

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Lys Ser
1

<210> SEQ ID NO 57
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Asp Leu Leu Gly Asp Gly Trp
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Tyr Thr Phe Thr Ser Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Pro Tyr Thr Gly Asp
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Lys Val Tyr Met Asp Ile
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Ser Leu Gly Ser Tyr Tyr
1               5

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

Arg Asn Lys
1

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Asp Trp Met Tyr Ser Ser Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Phe Thr Phe Ser Asp Tyr
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Ser Lys Thr Asp Gly Gly Ile
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ile Tyr Tyr Leu Glu Ala Phe Asp Val
1               5                   10

<210> SEQ ID NO 67
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

```
Arg Asn Lys Gln Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Phe Asp Ser Gln Ala Val Thr
                 85                  90                  95

Asn Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
210

<210> SEQ ID NO 68
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Ile His Trp Val Arg Gln Ala Pro Gly Lys Gly Leu Glu Trp Val
         35                  40                  45

Gly Arg Ile Lys Ser Lys Thr Asp Gly Gly Ile Thr Glu Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Asp Tyr Lys Asp Asp Asp Lys Gly Ala Pro His His His His
225                 230                 235                 240

His His

<210> SEQ ID NO 69
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Phe Asp Ser Gln Ala Val Thr
                85                  90                  95

Asn Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
        210

<210> SEQ ID NO 70
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
            35                  40                  45

Gly Arg Ile Lys Ser Lys Thr Asp Gly Gly Ile Thr Glu Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Glu
210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
            275                 280                 285

Ala Pro His His His His His His
            290                 295

<210> SEQ ID NO 71
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
            35                  40                  45

Arg Asn Lys Gln Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80
```

```
Asp Asp Ala Asp Tyr Tyr Cys Ala Thr Tyr Asp Ser Ser Trp Trp
                85                  90                  95

Asn Val Phe Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 72
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
```

```
                   210                 215                 220
Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 73
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Trp Ala Arg His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 74
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 75
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

```
Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Tyr Thr Ser Pro Ile Asn Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
                115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
                195                 200                 205

Thr Glu Ala
    210

<210> SEQ ID NO 76
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Gly Ile His Trp Val Arg Gln Ala Pro Gly Lys Gly Leu Glu Trp Val
             35                  40                  45

Gly Arg Ile Lys Ser Lys Thr Asp Gly Gly Ile Thr Glu Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Ala Ile Tyr Tyr Leu Glu Ala Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
            245                 250                 255

Leu Glu Glu Leu Leu Lys His Leu Leu Glu Leu Leu Lys Gly Gly Ser
        260                 265                 270

Gly Gly Ala Pro Glu Gln Lys Leu Ile Ser Glu Glu Asp Leu Asn Asp
        275                 280                 285

Ala Pro His His His His His His
        290                 295

<210> SEQ ID NO 77
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Asp Ala Asp Tyr Tyr Cys Ala Val Trp Asp Asp Glu Pro His His
                85                  90                  95

Asp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 78
<211> LENGTH: 296
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 79
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
```

```
                    20                  25                  30
His Trp Tyr Gln Gln Lys Pro Gly Gln Ala Pro Val Leu Val Ile Tyr
            35                  40                  45

Arg Asn Lys Gln Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Asp Ala Asp Tyr Tyr Cys Gln Thr Tyr Asp Ser Leu Lys Phe Ser
                    85                  90                  95

Arg Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
            195                 200                 205

Ala Pro Thr Glu Ala
        210

<210> SEQ ID NO 80
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 81
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210
```

```
<210> SEQ ID NO 82
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly His Ile Lys Ser Ser Asn Met Gly Gly Ala Ala Gln Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 83
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
        210

<210> SEQ ID NO 84
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Phe Thr Lys Asn Glu Val Gly Gly Tyr Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 85
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
            195                 200                 205

Ala Pro Thr Glu Ala
    210

<210> SEQ ID NO 86
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ala Phe Lys Glu Gly Tyr Ile Thr Gln Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Pro Lys Pro Ser Thr Pro Pro Gly Ser Ser Gly Glu Leu Glu Glu
225                 230                 235                 240

Leu Leu Lys His Leu Lys Glu Leu Leu Lys Gly Pro Arg Lys Gly Glu
                245                 250                 255

Leu Glu Glu Leu Leu Lys His Leu Lys Glu Leu Leu Lys Gly Gly Ser
            260                 265                 270

Gly Gly Ala Pro Glu Gln Lys Leu Ile Ser Glu Glu Asp Leu Asn Asp
        275                 280                 285

Ala Pro His His His His His His
    290                 295

<210> SEQ ID NO 87
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Pro Ser Lys Tyr Ala
            20                  25                  30

His Trp Tyr Gln Gln Lys Pro Gly Gln Ala Pro Val Leu Val Ile Tyr
        35                  40                  45

Gly Lys Ser His Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ala Trp Asp Leu Leu Gly Asp Gly
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210
```

<210> SEQ ID NO 88
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Met His Trp Val Arg Gln Ala Pro Gly Gln Gly Leu Glu Trp Met
        35                  40                  45

Gly Trp Ile Asn Pro Tyr Thr Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Lys Val Tyr Met Asp Ile Trp Gly Gln Gly Thr Leu Val
            100                 105                 110
```

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 89
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
```

```
                        20                  25                  30
His Trp Tyr Gln Gln Lys Pro Gly Gln Ala Pro Val Leu Val Ile Tyr
                35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 90
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Gly Asp Ser Leu Gly Ser Tyr Tyr Val His
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 92

Leu Val Ile Tyr Arg Asn Lys Gln Arg Pro Ser
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Thr Phe Asp Ser Gln Ala Val Thr Asn
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Phe Thr Phe Ser Asp Tyr Gly Ile His
1               5

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ile Lys Ser Lys Thr Asp Gly Gly Ile Thr Glu Tyr Ala Ala Pro
1               5                   10                  15

Val Lys Gly

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ile Tyr Tyr Leu Glu Ala Phe Asp Val
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Asp Ser Leu Gly Ser Tyr Tyr Val His
1               5                   10
```

```
<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Val Ile Tyr Arg Asn Lys Gln Arg Pro Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Thr Phe Asp Ser Gln Ala Val Thr Asn
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Phe Thr Phe Ser Asp Tyr Gly Ile His
1               5

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ile Lys Ser Lys Thr Asp Gly Gly Ile Thr Glu Tyr Ala Ala Pro
1               5                   10                  15

Val Lys Gly

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Ile Tyr Tyr Leu Glu Ala Phe Asp Val
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 103

Ser Gly Asp Ser Leu Gly Ser Tyr Tyr Val His
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Val Ile Tyr Arg Asn Lys Gln Arg Pro Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Thr Tyr Asp Ser Ser Ser Trp Trp Asn
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Thr Phe Ser Asp Tyr Gly Ile His
1               5

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ile Lys Ser Lys Thr Asp Gly Gly Ile Thr Glu Tyr Ala Ala Pro
1               5                   10                  15

Val Lys Gly

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Ile Tyr Tyr Leu Glu Ala Phe Asp Val
1               5                   10

```
<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Gly Asp Ser Leu Gly Ser Tyr Tyr Val His
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Val Ile Tyr Arg Asn Lys Gln Arg Pro Ser
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Thr Trp Asp Trp Trp Ala Arg His Trp
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Thr Phe Ser Asp Tyr Gly Ile His
1               5

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ile Lys Ser Lys Thr Asp Gly Gly Ile Thr Glu Tyr Ala Ala Pro
1               5                   10                  15

Val Lys Gly

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 114

Ala Ile Tyr Tyr Leu Glu Ala Phe Asp Val
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Gly Asp Ser Leu Gly Ser Tyr Tyr Val His
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Val Ile Tyr Arg Asn Lys Gln Arg Pro Ser
1               5                   10

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Ser Tyr Thr Ser Pro Ile Asn
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Thr Phe Ser Asp Tyr Gly Ile His
1               5

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Ile Lys Ser Lys Thr Asp Gly Gly Ile Thr Glu Tyr Ala Ala Pro
1               5                   10                  15

Val Lys Gly
```

```
<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ile Tyr Tyr Leu Glu Ala Phe Asp Val
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Gly Asp Ser Leu Gly Ser Tyr Tyr Val His
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Val Ile Tyr Arg Asn Lys Gln Arg Pro Ser
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Val Trp Asp Asp Glu Pro His His Asp
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Phe Thr Phe Ser Asp Tyr Gly Ile His
1               5

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125
```

```
Arg Ile Lys Ser Lys Thr Asp Gly Gly Ile Thr Glu Tyr Ala Ala Pro
1               5                   10                  15

Val Lys Gly

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Ile Tyr Tyr Leu Glu Ala Phe Asp Val
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Gly Asp Ser Leu Gly Ser Tyr Tyr Val His
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Val Ile Tyr Arg Asn Lys Gln Arg Pro Ser
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Thr Tyr Asp Ser Leu Lys Phe Ser Arg
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Phe Thr Phe Ser Asp Tyr Gly Ile His
1               5

<210> SEQ ID NO 131
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ile Lys Ser Lys Thr Asp Gly Gly Ile Thr Glu Tyr Ala Ala Pro
1               5                   10                  15

Val Lys Gly

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Ile Tyr Tyr Leu Glu Ala Phe Asp Val
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Asp Ser Leu Gly Ser Tyr Tyr Val His
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Val Ile Tyr Arg Asn Lys Gln Arg Pro Ser
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Thr Tyr Asp Trp Met Tyr Ser Ser Arg
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136
```

```
Phe Thr Phe Ser Asn Ala Trp Met Ser
1               5
```

<210> SEQ ID NO 137
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
His Ile Lys Ser Ser Asn Met Gly Gly Ala Ala Gln Tyr Ala Ala Ser
1               5                   10                  15

Val Lys Gly
```

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Ala Ile Tyr Tyr Leu Glu Ala Phe Asp Val
1               5                   10
```

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Ser Gly Asp Ser Leu Gly Ser Tyr Tyr Val His
1               5                   10
```

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Leu Val Ile Tyr Arg Asn Lys Gln Arg Pro Ser
1               5                   10
```

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Gln Thr Tyr Asp Trp Met Tyr Ser Ser Arg
1               5                   10
```

<210> SEQ ID NO 142
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Thr Phe Ser Asn Ala Trp Met Ser
1               5

<210> SEQ ID NO 143
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Phe Thr Lys Asn Glu Val Gly Gly Tyr Thr Thr Glu Tyr Ala Ala Ser
1               5                   10                  15

Val Lys Gly

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile Tyr Tyr Leu Glu Ala Phe Asp Val
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly Asp Ser Leu Gly Ser Tyr Tyr Val His
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Val Ile Tyr Arg Asn Lys Gln Arg Pro Ser
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

```
Gln Thr Tyr Asp Trp Met Tyr Ser Ser Arg
1               5                   10
```

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Phe Thr Phe Ser Asn Ala Trp Met Ser
1               5
```

<210> SEQ ID NO 149
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Arg Ile Lys Ala Phe Lys Glu Gly Tyr Ile Thr Gln Tyr Ala Ala Ser
1               5                   10                  15

Val Lys Gly
```

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Ala Ile Tyr Tyr Leu Glu Ala Phe Asp Val
1               5                   10
```

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Ser Gly Asp Ser Ile Pro Ser Lys Tyr Ala His
1               5                   10
```

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

```
Leu Val Ile Tyr Gly Lys Ser His Arg Pro Ser
1               5                   10
```

<210> SEQ ID NO 153
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Ala Trp Asp Leu Leu Gly Asp Gly
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Phe Thr Ser Tyr His Met His
1               5

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Trp Ile Asn Pro Tyr Thr Gly Asp Thr Asn Tyr Ala Gln Lys Phe Gln
1               5                   10                  15

Gly

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Lys Val Tyr Met Asp Ile
1               5

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Gly Asp Ser Leu Gly Ser Tyr Tyr Val His
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Leu Val Ile Tyr Arg Asn Lys Gln Arg Pro Ser
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Thr Tyr Asp Trp Met Tyr Ser Ser Arg
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Phe Thr Phe Ser Asp Tyr Gly Ile His
1               5

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Ile Lys Ser Lys Thr Asp Gly Gly Ile Thr Glu Tyr Ala Ala Pro
1               5                   10                  15

Val Lys Gly

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Ile Tyr Tyr Leu Glu Ala Phe Asp Val
1               5                   10
```

ANTIBODIES AND METHODS FOR WNT PATHWAY-RELATED DISEASES

CROSS REFERENCE TO RELATED APPLICATIONS

This application is a U.S. National Phase Application filed under 35 U.S.C. §371 claiming benefit to International Patent Application No. PCT/IB2012/055560 filed on Oct. 12, 2012, which is entitled to priority under 35 U.S.C. §119(e) to U.S. Provisional Application No. 61/547,209 filed Oct. 14, 2011, each of which is hereby incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 11, 2014, is named PAT054745-US-PCT_SL.txt and is 113,126 bytes in size.

FIELD OF THE INVENTION

The invention relates generally to monoclonal antibodies that bind to receptors and specifically to antibodies that bind to ZNRF3 protein or to RNF43 protein.

BACKGROUND OF THE INVENTION

Wnt signaling pathways are a network of proteins in eukaryotic cells that are important for regulating cell growth and differentiation. Logan C Y and Nusse R, "The Wnt signaling pathway in development and disease." *Annu. Rev. Cell. Dev. Biol.* 20:781-810 (2004); Nusse R., "Wnt signaling in disease and in development." *Cell Res.* 15(1):28-32 (January 2005); Clevers H, "Wnt/beta-catenin signaling in development and disease." *Cell* 127(3):469-80 (3 Nov. 2006). Wnt signaling is essential for regulating cell growth and differentiation during embryonic development. In adults, Wnt signaling promotes tissue homeostasis.

Dysregulation of Wnt signaling has been implicated in many human diseases. Aberrant over-activation of Wnt pathway can be involved in causing tumorigenesis of colorectal carcinomas. Conversely, pathologically low levels of Wnt signaling have been associated with osteoporosis, osteoarthritis, polycystic kidney disease and neurodegenerative diseases. Controlled activation of Wnt pathway has been shown to promote regenerative processes such as tissue repair and wound-healing. Zhao J, Kim K A and Abo A, "Tipping the balance: modulating the Wnt pathway for tissue repair." *Trends Biotechnol.* 27(3):131-6 (March 2009).

Wnt proteins are proteins ligands that bind to cell surface receptors (the "Wnt receptor complex") to activate Wnt pathways in a cell. Several kinds of Wnt pathways have been identified, both canonical and non-canonical.

Wnt signaling through a canonical Wnt/β-catenin pathway regulates the cellular turn-over of the transcription cofactor protein β-catenin. MacDonald B T, Tamai K and He X, "Wnt/beta-catenin signaling: components, mechanisms, and diseases." *Dev. Cell* 17(1):9-26 (July 2009) and U.S. Patent Application 2009/0220488, entitled "Evaluating and treating scleroderma". In the absence of Wnt ligands, β-catenin remains phosphorylated by a multi-protein "destruction complex", which triggers polyubiquitination of the β-catenin and degradation of β-catenin in the proteosomes of the cell. When Wnt binds to the Wnt receptor complex, β-catenin is stabilized through inhibition of the "destruction complex". The β-catenin then translocates to the nucleus. In the nucleus, β-catenin activates transcription of Wnt target genes and thus activates the gene expression programs for cell growth and differentiation.

In the canonical Wnt/β-catenin pathway, Frizzled (FZD) proteins and Low-Density-Lipoprotein Receptor-Related Protein 5/6 (LRP5/6) form the receptor complex. Both Frizzled proteins and LRP5/6 are important for the canonical Wnt/β-catenin pathway.

In a non-canonical, β-catenin independent pathway, Wnt signaling regulates planar cell polarity (PCP) or tissue polarity signaling, which governs cells and tissue movements. Zallen J A, "Planar polarity and tissue morphogenesis." *Cell* 129(6):1051-63 (15 Jun. 2007); Simons M and Mlodzik M, "Planar cell polarity signaling: from fly development to human disease." *Annu. Rev. Genet;* 42:517-40 (2008); U.S. Patent Application 2009/0220488. Frizzled proteins are receptors in the non-canonical Wnt signaling, but LRP5/6 is not essential.

Despite the many proteins that are involved in Wnt signaling pathways, few druggable targets in the pathway have been identified, especially targets upstream in the pathway of β-catenin in the Wnt pathway. A need exists for agents that potentiate Wnt signaling, to develop therapies for Wnt signaling-related disorders.

SUMMARY OF THE INVENTION

The invention proceeds from the inventors' identification of two homologous transmembrane E3 ubiquitin ligases as active negative regulators of the amount of Wnt receptor complex on the surface of cells. The ligases are Zinc/RING finger protein 3 (ZNRF3) and Ring finger protein 43 (RNF43). The inventors also show that ZNRF3 and RNF43 are molecular targets of R-spondin (RSPO) proteins, a group of secreted proteins that strongly sensitize cells to Wnt signaling. The inventors further show that R-spondin induces the interaction between ZNRF3 and the leucine-rich repeat-containing G-protein coupled receptor 4 (LGR4), which leads to inhibition of ZNRF3 and activation of Wnt signaling.

The invention provides for the modulation of ZNRF3 or RNF43 activity by antibody binding to the extracellular domain of ZNRF3 or RNF43 proteins on the surface of a eukaryotic cell to increase Wnt signaling in the eukaryotic cell. In one embodiment, the invention is an anti-ZNRF3 antagonizing antibody that increases Wnt signaling. In another embodiment, the invention is an anti-RNF43 antagonizing antibody that increases Wnt signaling.

The invention also provides for the medical use of the antagonizing antibodies of the invention to treat diseases and conditions with low Wnt signaling. Some of the diseases and conditions associated with low Wnt signaling include, but are not limited to, mucositis short bowel syndrome, bacterial translocation in the gastrointestinal mucosa, enterotoxigenic or enteropathic infectious diarrhea, celiac disease, non-tropical sprue, lactose intolerance and other conditions where dietary exposures cause blunting of the mucosal villi and malabsorption, atrophic gastritis and type II diabetes mellitus. Also included are osteoporosis, bone fracture, metabolic diseases such as diabetes, neurodegenerative disease and melanoma. In addition, the antagonizing antibodies of the invention can be used to enhance Wnt signaling for tissue regeneration, such as tissue repair and wound healing.

The invention further provides an antibody with multiple binding specificities, such as a bispecific antibody. One part of the antibody binds to the extracellular domain of ZNRF3 or RNF43. The other part of the antibody binds to the extracellular domain of a coreceptor of R-spondin, e.g., LGR4, LGR5 (also known as GPR49) or LGR6. For example, in certain embodiments the disclosure relates:

(i) to antibodies where one part of the antibody binds to the extracellular domain of ZNRF3 and the other part of the antibody binds to the extracellular domain of a coreceptor of R-spondin, or (ii) to antibodies where one part of the antibody binds to the extracellular domain of RNF43 and the other part of the antibody binds to the extracellular domain of a coreceptor of R-spondin.

The invention provides for the use of the antibody of the invention in as a combination therapy with a DPP-4 inhibitor to treat type II diabetes mellitus. The antibody of the invention is administered to increase levels of incretin hormones. Since DPP-4 inhibitors require endogenous production of incretins for efficacy, the antibody of the invention can be administered as a combination therapy with a DPP-4 inhibitor, such as vildagliptin (Galvus®) or another DPP-4 inhibitor. The combination therapy may be the administration of the antibody of the invention before the administration of a DPP-4 inhibitor or with the administration of a DPP-4 inhibitor.

The invention provides for the use of anti-ZNRF3 or anti-RNF43 antibodies that bind to the external regions of ZNRF3 or RNF43, respectively, for utilities that do not require modulating ZNRF3 or RNF43 activity to increase Wnt signaling. Antibodies to ZNRF3 or RNF43 external regions can be used to diagnose diseases where ZNRF3 or RNF43 are highly expressed as a result of Wnt pathway hyper-activation, such as in certain types of tumors, for example colon adenocarcinoma. Antibodies to ZNRF3 or RNF43 external regions can also be used in antibody drug conjugate (ADC), antibody-dependent cell-mediated cytotoxicity (ADCC) or other similar methods for cancer cell specific delivery and killing.

The invention provides antibodies to ZNRF3 external regions that can be used to interfere with R-spondin binding to ZNRF3 and inhibit R-spondin-induced Wnt signaling. Such antibodies can be used to treated conditions associated with high Wnt signaling, including, but not limited to, cancers, osteoarthritis, sclerosteosis, idiopathic pulmonary fibrosis, and cardiac hypertrophy.

The invention also provides a soluble extracellular domain of a transmembrane E3 ubiquitin ligase (ZNRF3 or RNF43) in a pharmaceutically acceptable carrier, for use in treating a disease or other indication that will benefit from a decrease in Wnt signaling. The soluble extracellular domain of a ZNRF3 or RNF43 specifically binds to R-spondin to block R-spondin-stimulated Wnt signaling. Such antibodies can be used to treated conditions associated with high Wnt signaling, including, but not limited to, cancers, osteoarthritis, sclerosteosis, idiopathic pulmonary fibrosis, and cardiac hypertrophy.

DETAILED DESCRIPTION OF THE INVENTION

Figure 1:
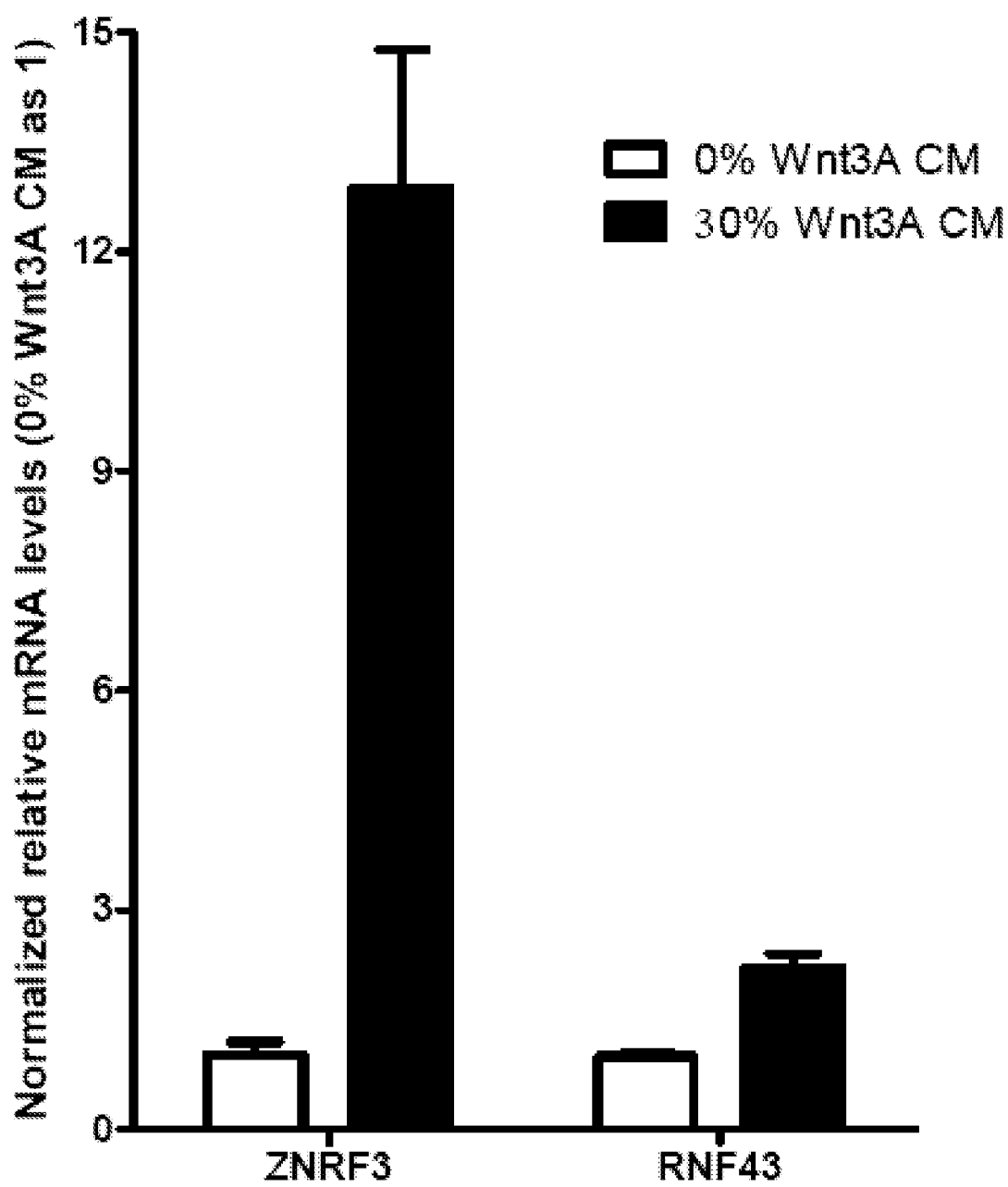
FIG. 1 is a set of bar graphs showing that ZNRF3 and RNF43 are Wnt target genes. Mouse L cells were treated with or without Wnt3A conditioned media (CM) for 24 hr. Total RNA was extracted to perform reverse transcription and qPCR analysis with ZNRF3, RNF43 and GUSB Taqman® probes. ΔΔCt method was used to obtain mRNA levels, with the levels shown in the bar graphs being normalized to mRNA levels for GUSB (the human gene for β-glucuronidase) and relative to no Wnt3A conditioned media.

The invention provides the following: First, ZNRF3 and RNF43 are cell surface proteins, and thus potentially druggable following antibody binding to ZNRF3 or RNF43. Second, ZNRF3 and RNF43 are negative regulators of β-catenin and the Wnt signaling pathway. Inhibition of ZNRF3 by the use of siRNA or by expression of dominant negative mutant ZNRF3 protein causes an increase in Wnt signaling. Third, RNF43 is a functional homolog of ZNRF3. Fourth, antibodies to ZNRF3 that bind to the extracellular domain of the protein mimic the effect of inhibition of ZNRF3 by the use of siRNA or by expression of dominant negative mutant ZNRF3 protein, thus causing an increase in Wnt signaling. Fifth, various types of antibodies to ZNRF3 or RNF43 that bind to the extracellular domain of the proteins can be produced by known methods of producing antibodies having a specified binding. Sixth, inhibition of ZNRF3 enhances Wnt/β-catenin signaling and disrupts Wnt/PCP signaling in vivo. Seventh, the use of antibodies to ZNRF3 and RNF43 that bind to the extracellular domains of the proteins to increase Wnt signaling and thus to treat deficiencies of Wnt signaling can be accomplished using known methods of administration of therapeutic antibodies. Eighth, because R-spondin has been shown by the inventors to inhibit ZNRF3 through increasing the association between ZNRF3 and LGR4, bispecific antibodies that bind to either ZNRF3 or RNF43, on one hand, and LGR4, LGR5 or LGR6, on the other hand, can be used to mimic R-spondin and increase Wnt signaling in eukaryotic cells. Ninth, because the membrane E3 ubiquitin ligase ZNRF3 has now been shown by the inventors to be the molecular target of R-spondin, antibodies that bind to ZNRF3 can be used to inhibit the activity of R-spondin for eukaryotic cells.

ZNRF3 and RNF43 are cell surface proteins. Zinc/RING finger protein 3 (ZNRF3, Swiss-Prot Q9ULT6, SEQ ID NO: 1) and Ring finger protein 43 (RNF43, Swiss-Prot Q68DV7, SEQ ID NO: 2) are structurally related RING finger proteins. Each of the proteins contains a signal peptide, an extracellular domain, a transmembrane domain, and an intracellular RING domain (an atypical zinc finger domain).

TABLE 1

Amino Acid Sequences for Human ZNRF3 Protein and Human RNF43 Protein

| | |
|---|---|
| Zinc/RING finger protein 3 (ZNRF3, Swiss-Prot Q9ULT6, SEQ ID NO: 1) The extracellular domain is from amino acids 56-219. | MRPRSGGRPG ATGRRRRRLR RRPRGLRCSR LPPPPPLPLL LGLLLAAAGP GAARAKETAF VEVVLFESSP SGDYTTYTTG LTGRFSRAGA TLSAEGEIVQ MHPLGLCNNN DEEDLYEYGW VGVVKLEQPE LDPKPCLTVL GKAKRAVQRG ATAVIFDVSE NPEAIDQLNQ GSEDPLKRPV VYVKGADAIK LMNIVNKQKV ARARIQHRPP RQPTEYFDMG IFLAFFVVVS LVCLILLVKI KLKQRRSQNS MNRLAVQALE KMETRKFNSK SKGRREGSCG ALDTLSSSST SDCAICLEKY IDGEELRVIP CTHRFHRKCV DPWLLQHHTC PHCRHNIIEQ KGNPSAVCVE TSNLSRGRQQ RVTLPVHYPG RVHRTNAIPA YPTRTSMDSH GNPVTLLTMD RHGEQSLYSP QTPAYIRSYP PLHLDHSLAA HRCGLEHRAY SPAHPFRRPK LSGRSFSKAA CFSQYETMYQ HYYFQGLSYP EQEGQSPPSL APRGPARAFP PSGSGSLLFP TVVHVAPPSH LESGSTSSFS CYHGHRSVCS GYLADCPGSD SSSSSSSGQC HCSSSDSVVD CTEVSNQGVY GSCSTFRSSL SSDYDPFIYR SRSPCRASEA GGSGSSGRGP ALCFEGSPPP EELPAVHSHG AGRGEPWPGP ASPSGDQVST CSLEMNYSSN SSLEHRGPNS STSEVGLEAS PGAAPDLRRT WKGGHELPSC ACCCEPQPSP AGPSAGAAGS STLFLGPHLY EGSGPAGGEP QSGSSQGLYG LHPDHLPRTD GVKYEGLPCC FYEEKQVARG GGGGSGCYTE DYSVSVQYTL TEEPPPGCYP GARDLSQRIP IIPEDVDCDL GLPSDCQGTH SLGSWGGTRG PDTPRPHRGL GATREEERAL CCQARALLRP GCPPEEAGAV RANFPSALQD TQESSTTATE AAGPRSHSAD SSSPGA |
| Ring finger protein 43 (RNF43, Swiss-Prot Q68DV7, SEQ ID NO: 2) The extracellular domain is from amino acids 24-197. | MSGGHQLQLA ALWPWLLMAT LQAGFGRTGL VLAAAVESER SAEQKAIIRV IPLKMDPTGK LNLTLEGVFA GVAEITPAEG KLMQSHPLYL CNASDDDNLE PGFISIVKLE SPRRAPRPCL SLASKARMAG ERGASAVLFD ITEDRAAAEQ LQQPLGLTWP VVLIWGNDAE KLMEFVYKNQ KAHVRIELKE PPAWPDYDVW ILMTVVGTIF VIILASVLRI RCRPRHSRPD PLQQRTAWAI SQLATRRYQA SCRQARGEWP DSGSSCSSAP VCAICLEEFS EGQELRVISC LHEFHRNCVD PWLHQHRTCP LCMFNITEGD SFSQSLGPSR SYQEPGRRLH LIRQHPGHAH YHLPAAYLLG PSRSAVARPP RPGPFLPSQE PGMGPRHHRF PRAAHPRAPG EQQRLAGAQH PYAQGWGLSH LQSTSQHPAA CPVPLRRARP PDSSGSGESY CTERSGYLAD GPASDSSSGP CHGSSSDSVV NCTDISLQGV HGSSSTFCSS LSSDFDPLVY CSPKGDPQRV DMQPSVTSRP RSLDSVVPTG ETQVSSHVHY HRHRHHHYKK RFQWHGRKPG PETGVPQSRP PIPRTQPQPE PPSPDQQVTR SNSAAPSGRL SNPQCPRALP EPAPGPVDAS SICPSTSSLF NLQKSSLSAR HPQRKRRGGP SEPTPGSRPQ DATVHPACQI FPHYTPSVAY PWSPEAHPLI CGPPGLDKRL LPETPGPCYS NSQPVWLCLT PRQPLEPHPP GEGPSEWSSD TAEGRPCPYP HCQVLSAQPG SEEELEELCE QAV |

An anti-ZNRF3 antibody is commercially available from Santa Cruz Biotechnology. ZNRF3 (P-15) (product sc-86958) is an affinity purified goat polyclonal antibody raised against a peptide mapping within an internal region (rather than the extracellular region) of ZNRF3 of human origin.

ZNRF3 has not been extensively characterized previously, but RNF43 has been demonstrated by Sugiura et al. to have an E3 ubiquitin ligase activity. Sugiura T, Yamaguchi A and Miyamoto K, "A cancer-associated RING finger protein, RNF43, is an ubiquitin ligase that interacts with a nuclear protein, HAP95." *Exp. Cell Res.* 314(7):1519-28 (15 Apr. 2008). RNF43 has also been described in U.S. Pat. No. 7,425,612, entitled "Genes and polypeptides relating to human colon cancers".

The inventors performed three tests to show that ZNRF3 and RNF43 are cell surface proteins.

First, microscopy observations showed that ZNRF3 localizes to the cell surface membrane. The inventors genetically engineered some HEK293 cells to stably express a C-terminal green fluorescent protein (GFP) fusion of ZNRF3 and other HEK293 cells to stably express ZNRF3-GFP with the signal peptide deleted.

For our transfection assays, the inventors generated a full length human ZNRF3 cDNA (NM_001206998) by fusing a short variant (NM_032173) and a synthesized 300 base pair N-terminal fragment. We constructed an siRNA-resistant ZNRF3 cDNA by two-step PCR and was used as template for generating ZNRF3 ΔRING (missing amino acids 293-334) and ZNF3 extracellular domain (ECD)-transmembrane (TM) (amino acids 1-256). cDNAs were cloned in mammalian expression vectors under control of the CMV promoter. Plasmids were sequenced to confirm identity and the absence of undesirable mutation.

The inventors introduced the various constructs into HEK293 or HEK293 cells with a cloned SuperTopFlash® (STF) reporter (i.e., HEK293-STF) cells through retroviral or lentiviral infection using standard protocols.

For cell culture for our assays, we grew HEK293 cells or the derivative cell lines in Dulbecco's Modified Eagle's Medium (DMEM) supplemented with 10% fetal bovine serum (FBS).

Second, confocal microscopy analysis of our HEK293 cells and the derivative cell lines showed that ZNRF3-GFP was localized on the plasma membrane, while ZNRF3-GFP with the signal peptide deleted was diffusedly localized in the cytoplasm.

Third, the inventors confirmed our microscopy results in a cell surface protein biotinylation assay. We transfected HEK293 cells with a cloned SuperTopFlash® (STF) reporter with either full length ZNRF3-HA or signal peptide deleted ZNRF3 ASP-HA.

For our immunoblotting and immunoprecipitation assays, we used the following methods: Total cell lysates were prepared by lysing cells using RIPA buffer (50 mM Tris-HCl, pH 7.4, 150 mM NaCl, 1% NP-40, 0.5% sodium deoxycholate, 0.1% SDS, 1 mM EDTA) supplemented with protease inhibitors and phosphatase inhibitors, followed by centrifugation at 14,000 rpm for 10 min at 4° C. Equal amount of protein from each lysate (25~50 µg) were then resolved by SDS-PAGE and transferred to nitrocellulose membranes for blocking and incubation with indicated primary antibodies for overnight at 4° C. Secondary antibodies conjugated with either HRP or infrared dyes were used for signal visualization by ECL-film method or LI-COR Odyssey scanner, respectively. Quantification of immunoblotting bands was performed by densitometric analysis with AlphaEaseFC® software. For coimmunoprecipitation experiments, cells were lysed in buffer containing 50 mM Tris-HCl, pH 7.5, 150 mM NaCl, 1 mM EDTA, 0.8% Nonidet P40, phosphatase and protease inhibitors. Cleared cell lysates were incubated with the indicated antibodies and Protein G-sepharose beads (Amersham) overnight at 4° C. Beads were washed four times with lysis buffer and the bound proteins were eluted in SDS sample buffer for immunoblotting analysis.

Both sets of transfected HEK293 cells were biotinylated and affinity purified by strepavidin agarose according to the instructions of the commercially available Pierce® Cell Surface Protein Isolation Kit (Thermo Fisher Scientific Inc., Product No. 89881). Both the cell lysate (input) and pulldown eluate were immunoblotted with commercially available anti-HA antibody (Roche).

Our results showed that ZNRF3-HA, but not signal peptide deficient (ASP) mutant protein, was recovered in strepavidin pulldown after biotinylation of cell surface proteins. These immunological results confirmed the presence of an extracellular region on the ZNRF protein.

Thus, our results show that ZNRF3 and RNF43 are E3 ubiquitin ligases localized on the cell surface. Because ZNRF3 and RNF43 are on the cell surface, their activities can be directly regulated by ligand binding and thus druggable.

ZNRF3 and RNF43 are β-ctenin signaling targets and negative regulators of β-catenin and the Wnt signaling pathway.

Taken together, our results from the figures FIG. 1 to FIG. 5 show that ZNRF3 and RNF43 are Wnt/β-catenin signaling targets and negative regulators of β-catenin and the Wnt signaling pathway.

First, the expression of ZNRF3 and RNF43 is induced by Wnt3a conditioned media (CM) in cells with normal Wnt signaling pathway, as shown in FIG. 1.

For our PCR assays, total RNA from treated cells was extracted using the RNeasy Plus Mini Kit® (Qiagen) and reverse transcribed with Taqman Reverse Transcription Reagents® (Applied Biosystems) according to the manufacturer's instructions. Transcript levels were assessed using the ABI PRISM 7900HT Sequence Detection System®. Real-time PCR was performed in 12 µl reactions consisting of 0.6 µl of 20× Assay-on-Demand® mix (premixed concentration of 18 µM for each primer and 5 µM for Taqman® probe), 6 µl 2× Taqman Universal PCR Master Mix®, and 5.4 µl diluted cDNA template. The thermocycling conditions utilized were 2 min at 50° C., 10 min at 95° C., followed by 40 cycles of 15 sec at 95° C. and 1 min at 60° C.

The inventors performed gene expression analysis using the comparative ΔΔCT method with the housekeeping gene, GUSB, for normalization. The Assay-on-Demand® reagents used were purchased from Applied Biosystems.

In mouse L cells, Wnt3A treatment increased ZNRF3 and RNF43 expression by 12.9 fold and 2.2 fold, respectively, as measured by quantitative PCR. Our results show that ZNRF3 and RNF43 are Wnt/β-catenin signaling targets.

Figure 2A:
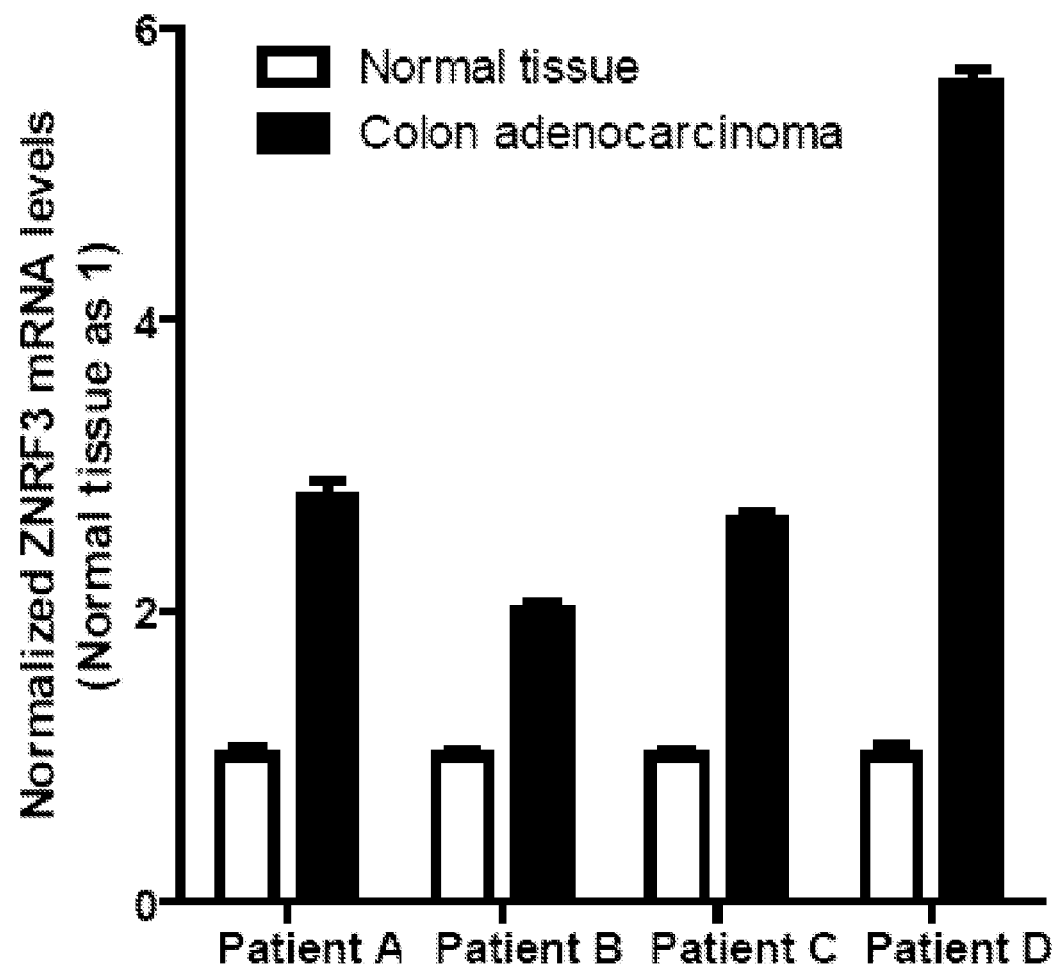
FIG. 2 is a set of bar graphs showing that ZNRF3 and RNF43 are upregulated in colon cancer. ZNRF3 mRNA levels (FIG. 2A) and RNF43 mRNA levels (FIG. 2B) were in colon adenocarcinoma and neighboring normal tissue from four patients. mRNA levels were measured and analyzed as described in FIG. 1.
Figure 2B:
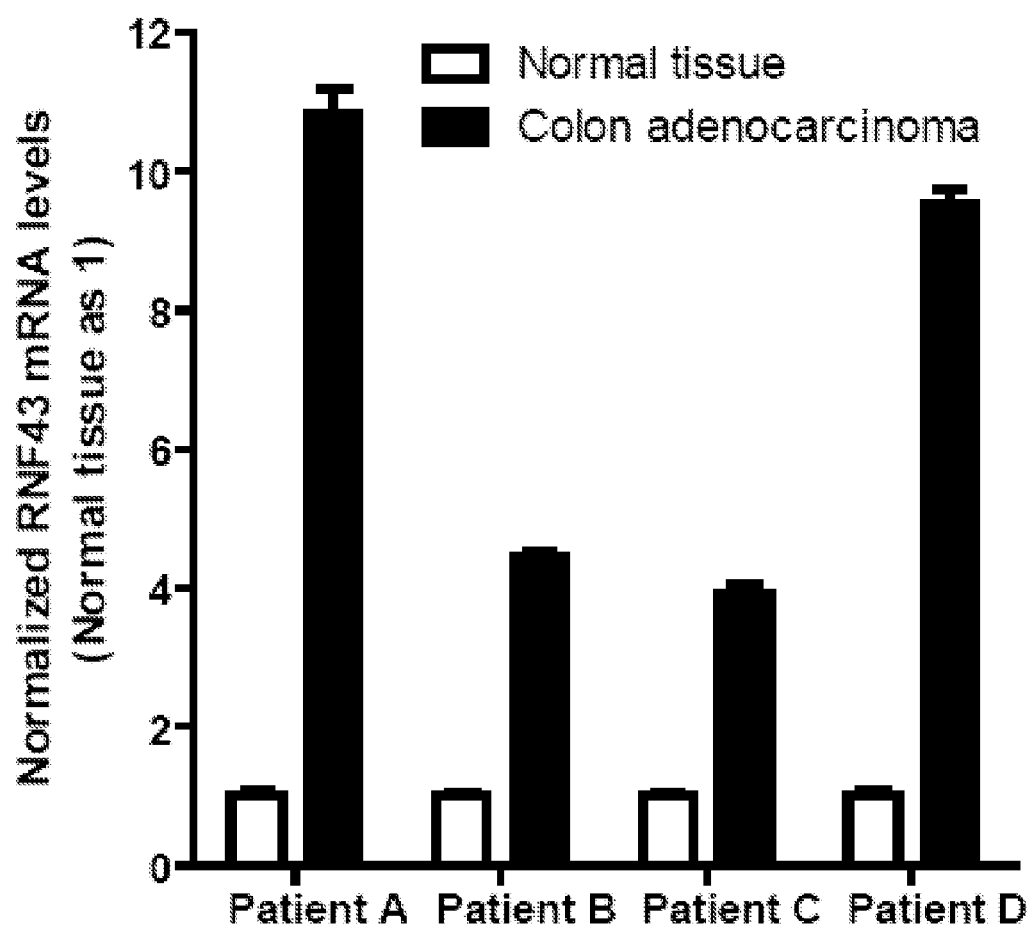

Second, the expression of ZNRF3 and RNF43 is increased in colorectal cancers with hyperactive β-catenin signaling, as shown in FIG. 2. Both ZNRF3 expression (FIG. 2A) and RNF43 expression (FIG. 2B) are elevated in colon adenocarcinoma cells, as shown by quantitative PCR analysis, by the methods described above.

Colon carcinoma is known to have hyperactivated Wnt signaling due to APC (adenomatous polyposis coli) gene mutation, such that the APC protein is truncated. The APC protein is a component of the β-catenin "destruction complex". Thus, the expression of ZNRF3 and RNF43 is induced because β-catenin is stabilized.

Figure 3:
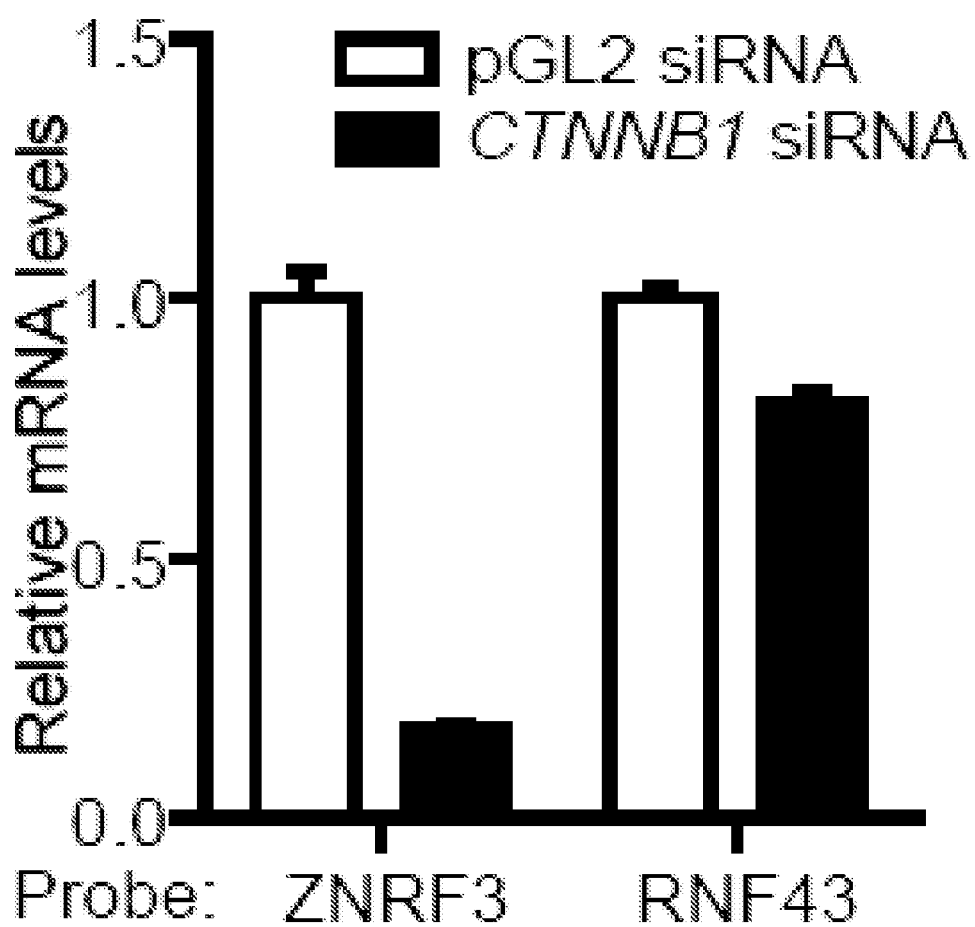
FIG. 3 is a set of bar graphs showing siRNA-mediated depletion of β-catenin gene (CTNNB1) in SW480 colon cancer cells and the effect on the relative mRNA levels of ZNRF3 and RNF43 in the cell line. All mRNA levels were measured using ΔΔCt method by TaqMan® probe-based quantitative RT-PCR with GUSB (the human gene for β-glucuronidase) as an internal control. Error bars denote the standard deviation (n=4).

Third, ZNRF3 mRNA expression in the SW480 colorectal cancer cell line is down-regulated upon siRNA-mediated depletion of β-catenin, as shown in FIG. 3.

Fourth, siRNA knockdown of ZNRF3 increases Wnt signaling in non-cancer cells. Fifth, expression of a dominant negative mutant of ZNRF3 likewise increases Wnt signaling.

Figure 4:
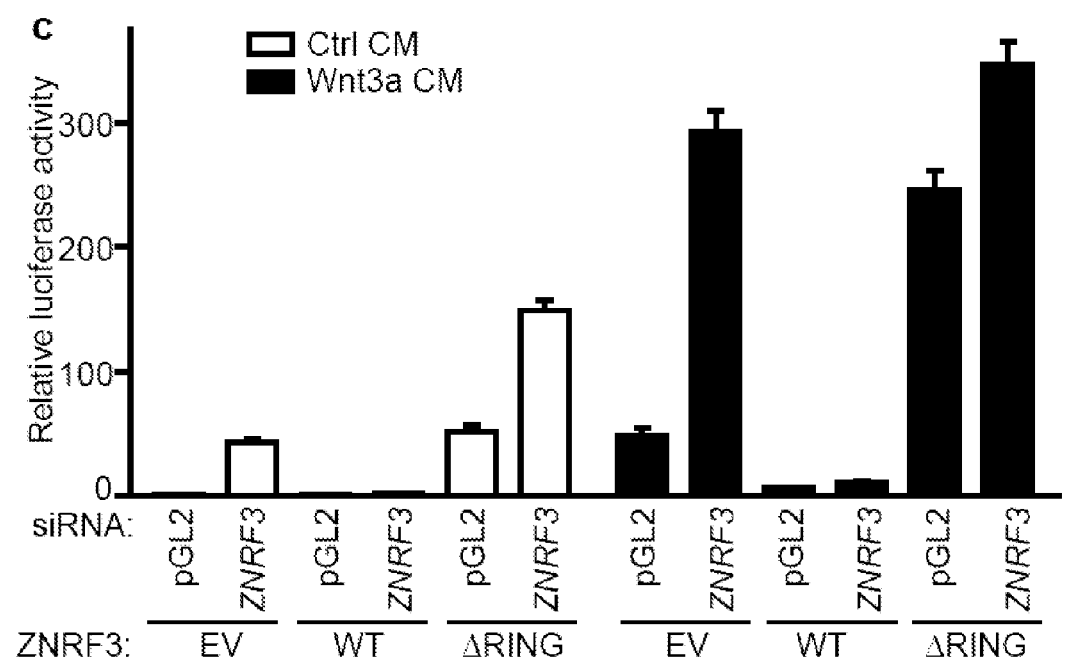
FIG. 4 is a set of bar graphs showing that ZNRF3 negatively regulates Wnt signaling. HEK293 cells with a cloned SuperTopFlash® (STF) reporter stably expressed either green fluorescent protein (GFP) or siRNA resistant (siR) and C-terminal hemagglutinin (HA) tagged wild-type (WT) ZNRF3 or ZNRF3 lacking the RING domain (ΔRING) were transfected with control siRNA (PGL2) or ZNRF3 siRNA. Two days post-transfection, 30% Wnt3A conditioned medium (CM) were added where indicated. Three days post transfection, luciferase activity was assayed using Bright-Glo® reagent from Promega.

Using HEK293 cells, the inventors found that siRNA knockdown of ZNRF3 significantly increased Wnt reporter activity as measured by SuperTopFlash® (STF) reporter activity, as shown in FIG. 4. HEK293-STF cells stably expressing empty vector (EV), siRNA resistant wild-type (WT) ZNRF3 or ZNRF3 ΔRING were transfected with control pGL2 siRNA or ZNRF3 siRNA, and STF activity was measured. For our assays, STF luciferase assays were performed using BrightGlo® or DualGlo® Luciferase Assay kits (Promega) according to the manufacturer's instructions. As described above, STF is a Wnt reporter assay. siRNA constructs used in the assays of FIG. 4 are listed in TABLE 2.

TABLE 2

| siRNA Constructs | |
| --- | --- |
| ZNRF3-1 (QiagenSI03089744), sense (SEQ. ID NO: 7) | cccaguauga gaccaugua |
| ZNRF3-1 (QiagenSI03089744), antisense (SEQ. ID NO: 8) | uacauggucu cauacuggga g |
| ZNRF3-2 (Qiagen1027020), sense (SEQ. ID NO: 9) | gcugcuacac ugaggacua |
| ZNRF3-2 (Qiagen1027020), antisense (SEQ. ID NO: 10) | uaguccucag uguagcagcc g |

Overexpression of siRNA-resistant ZNRF3 abolished ZNRF3 siRNA induced STF activation, as shown in FIG. 4. These results indicate that the effect of ZNRF3 siRNA is on-target.

We further found that overexpression of ZNRF3 mutant lacking the RING domain (ZNRF3 ΔRING) strongly increased STF activity, as shown in FIG. 4. Overexpression of ZNRF3 lacking the RING domain (ΔR) increased STF reporter activity by itself. Importantly, these effects were also observed without exogenous Wnt3A conditioned medium addition.

To summarize our results in FIG. 4, ZNRF3 siRNA-induced activation of STF is inhibited by siRNA resistant ZNRF3 and ZNRF3 ΔRING increases STF. Our results also show the dominant negative function of ZNRF3 ΔRING.

Figure 5:
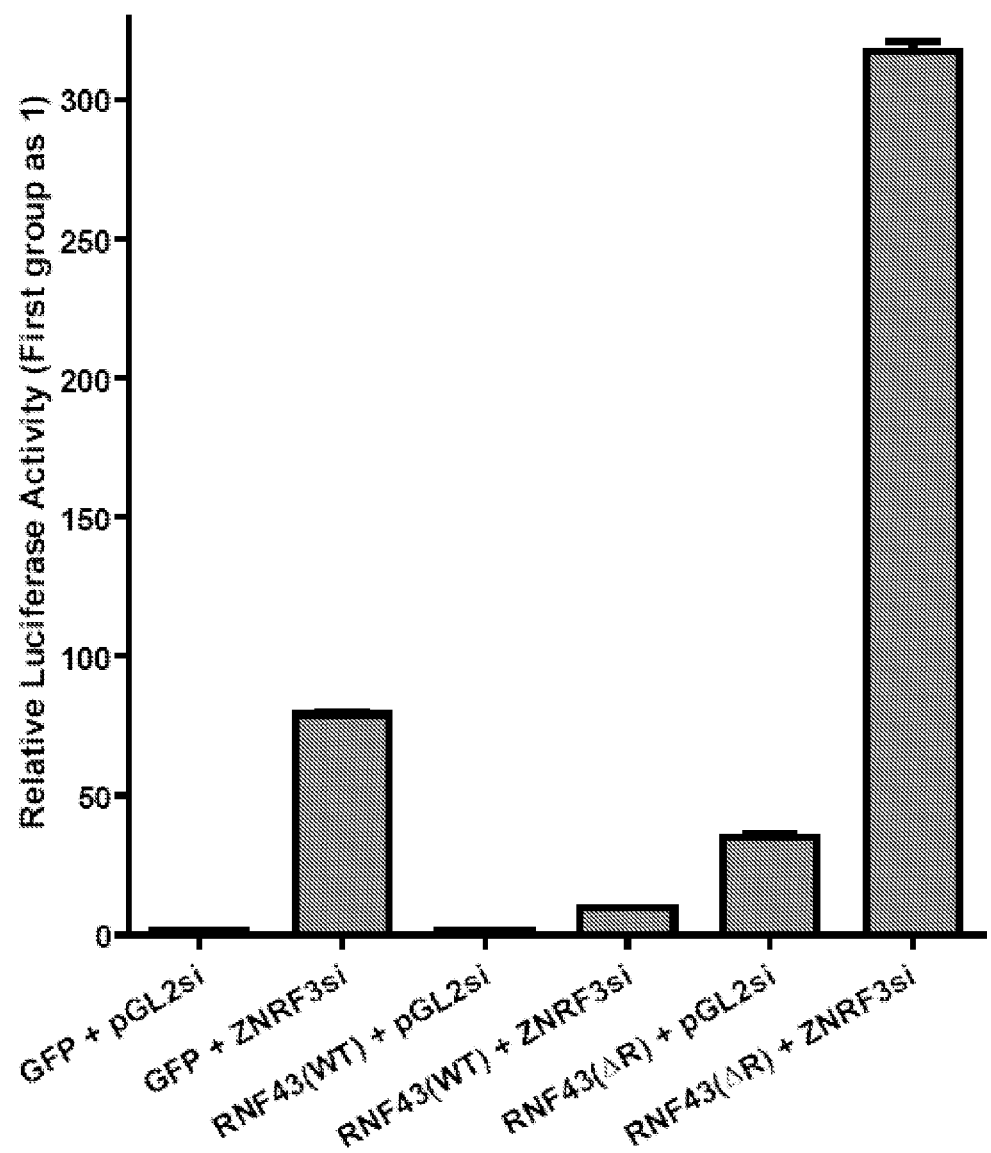
FIG. 5 is a set of bar graphs showing that RNF43 is a functional homolog of ZNRF3. The bar graphs represent the results of HEK293 cells with a cloned SuperTopFlash® (STF) reporter (i.e., 293-STF cells) stably expressing either GFP or wild-type (WT) RNF43 or RNF43 lacking the RING domain (ΔRING) were transfected with control siRNA (PGL2) or ZNRF3 siRNA. Three days post-transfection, luciferase activity was assayed using BrightGlo® reagent from Promega and normalized to GFP+pGL2si group.

Sixth, the results of FIG. 5 show that RNF43 is a functional homolog of ZNRF3 and thus a negative regulator of β-catenin and the Wnt signaling pathway. As described above, the E3 ligase RNF43 has high sequence homology with the E3 ligase ZNRF3. The results in FIG. 5 show that expression of RHF43 rescued the effect of ZNRF3 siRNA on STF reporter activity. siRNA constructs used in the assays of FIG. 5 are listed in TABLE 3.

TABLE 3

| siRNA Constructs | |
| --- | --- |
| RNF43 (Dharmacon J-007004-09-0005) (SEQ. ID NO: 11) | gcagaacaga aagcuauua |
| FZD6 (Dharmacon J-005505-07) (SEQ. ID NO: 12) | gaaggaagga uuaguccaa |

TABLE 3-continued

| siRNA Constructs | |
| --- | --- |
| LGR4-1 (Dharmacon J-003673-07) (SEQ. ID NO: 13) | aggauucacu guaacguua |
| LGR4-2 (Dharmacon J-003673-08) (SEQ. ID NO: 14) | uuacugaagc gacguguua |
| CTNNB1, sense (SEQ. ID NO: 15) | uguggucacc ugugcagcu |
| CTNNB1, antisense (SEQ. ID NO: 16) | agcugcacag gugaccaca |

Overexpression of wild-type RNF43 blocked ZNRF3 siRNA induced STF activation, while overexpression of RNF43 ΔRING increased STF. RNF43 (ΔR), which lacks the RING domain, also showed dominant negative activity against ZNRF3.

Seventh, IWP-2 is a known Porcupine inhibitor that blocks Wnt secretion. Chen B. et al. "Small molecule-mediated disruption of Wnt-dependent signaling in tissue regeneration and cancer." Nat. Chem. Biol. 5, 100-107 (2009). We found that IWP2 completely inhibited ZNRF3 siRNA or ZNRF3 ΔRING-induced β-catenin accumulation and STF activation in the absence of exogenous Wnt. Our results indicate that ZNRF3 suppresses β-catenin signaling initiated by endogenous Wnt proteins. Thus, our results distinguish ZNRF3 from other negative regulators of Wnt signaling.

Eighth, biochemical assays showed the molecular mechanism by which ZNRF3 regulates β-catenin signaling. HEK293 cells stably expressing empty vector (EV), siRNA-resistant wild-type or mutant ZNRF3 were transfected with control pGL2 siRNA or ZNRF3 siRNA.

Figure 6:
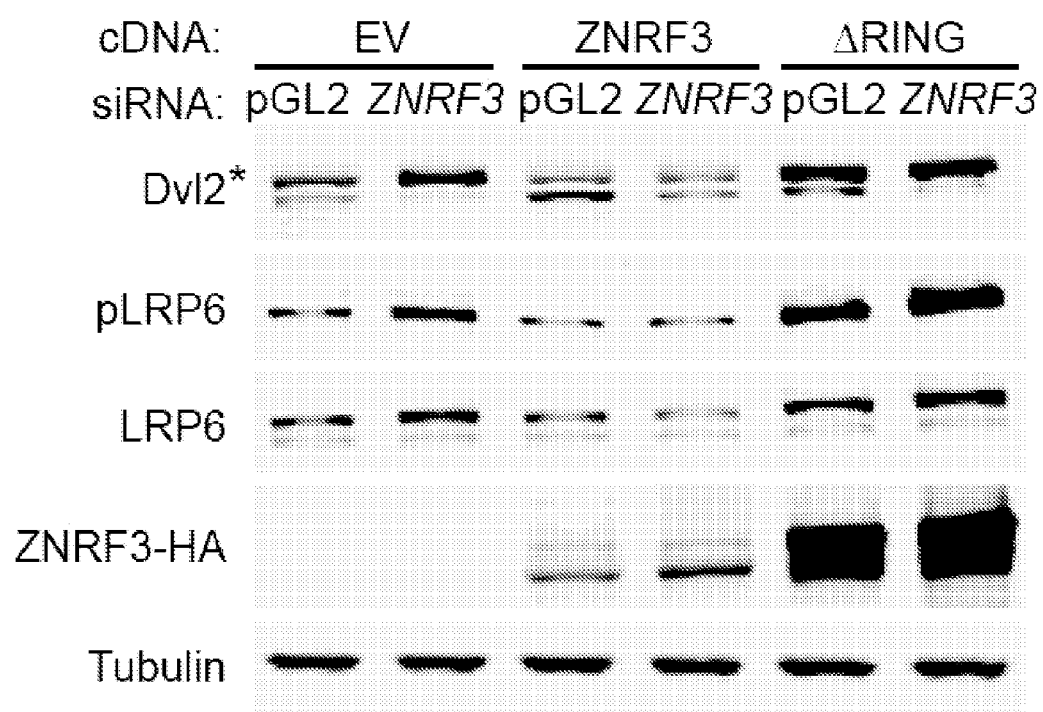
FIG. 6 is a set of polyacrylamide gel slices showing immunoblots of indicated proteins for the following cell lines and treatment: Wnt reporter assay of HEK293-STF cells stably expressing empty vector (EV), siRNA resistant ZNRF3 or ZNRF3 lacking the RING domain (ΔRING), after transfection of either control pGL2 siRNA or ZNRF3 siRNA. Error bars denote the standard deviation (n=4). The indicated proteins are phosphorylated Dvl2 (upper band); pLRP6, phosphorylated LRP6. Lower bands in LRP6 blot is the ER form of the protein, which is not affected by ZNRF3. Dvl2 is a segment polarity protein Dishevelled homolog.

Our immunoblot assay results are shown in FIG. 6. The sources of primary antibodies are: anti-LRP6, anti-Phospho-LRP6 (Ser1490) and anti-Dvl2 (Cell Signaling Technology); anti-HA (Roche); and anti-tubulin (Sigma).

Immunoblot assays showed that treatment with ZNRF3 siRNA or overexpression of ZNRF3 ΔRING increased the level of phospho-LRP6 and total LRP6. See, FIG. 7, lane 1, lane 2, and lane 5. The effect of ZNRF3 siRNA was blocked by expression of siRNA-resistant ZNRF3. See, FIG. 7, lane 2 and lane 4.

Figure 7:
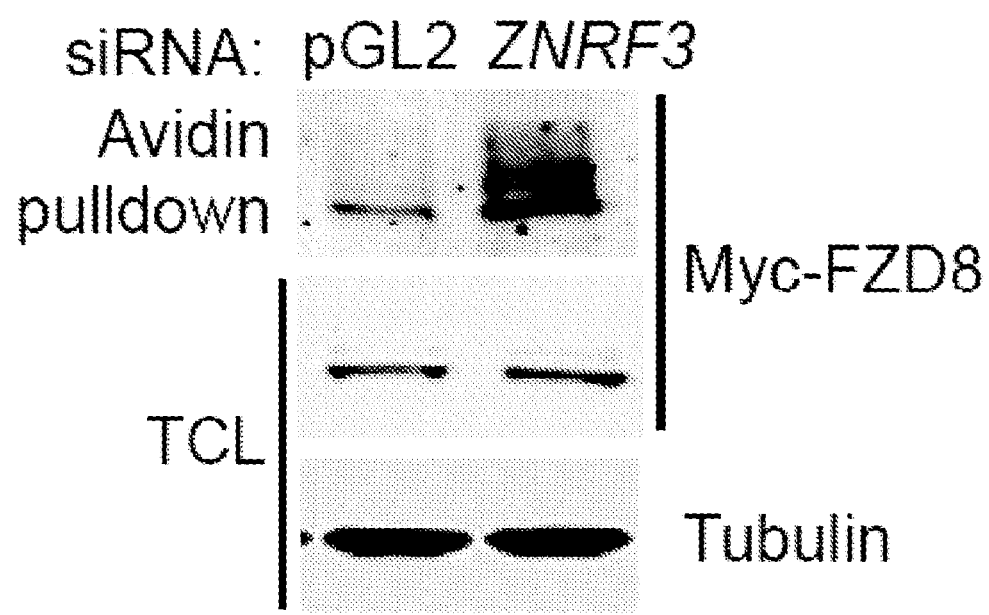
FIG. 7 is a set of polyacrylamide gel slices showing immunoblots of total and cell surface Myc-FZD8 (Frizzled 8) pulled down by neutravidin beads after biotinylation of HEK293 cells stably expressing Myc-FZD8. The cells were transfected with either control pGL2 siRNA or ZNRF3 siRNA. TCL, total cell lysate.

The protein expression level of ZNRF3 ΔRING is much higher compared to wild-type ZNRF3 in FIG. 7, consistent with ZNRF3 being an E3 ubiquitin ligase and subjected to autoubiquitination and subsequent degradation.

Interestingly, treatment with ZNRF3 siRNA and overexpression of ZNRF3 ΔRING increased segment polarity protein Dishevelled homolog Dvl2 phosphorylation. See, FIG. 7, lane 1, lane 2, and lane 5. Overexpression of wild-type ZNRF3 decreased Dvl2 phosphorylation. See, FIG. 7, lane 1 and lane 3. Dishevelled phosphorylation is a direct readout of Frizzled activation and not dependent on LRP6 activation. MacDonald BT, Tamai K, and He X, "Wnt/beta-catenin signaling: components, mechanisms, and diseases." Dev. Cell 17, 9-26 (2009). Thus, the results show that activity of Frizzled is also affected by ZNRF3.

Increased LRP6 plasma membrane expression upon ZNRF3 inhibition was confirmed using flow cytometric analysis, using anti-LRP6 antibody binding to HEK293 cells stably expressing either empty vector (EV) or ZNRF3 ΔRING.

For flow cytometry, cells were harvested using trypsin-free cell dissociation buffer (Invitrogen) and resuspended in FACS buffer (PBS with 1% BSA and 0.02% sodium azide). After blocking, cells were incubated with anti-LRP6 (R&D system) for 1 hour at 4° C. After extensive washes in FACS buffer, cells were stained with propidium iodide (PI) and subject to multi-channel analysis using BD LSR II flow cytometer.

Ninth, the inventors performed an assay to test that the level or activity of Frizzled is also affected by ZNRF3. To create an N-terminal Myc-tagged FZD8, we made genetic constructs where Frizzled 8 (FZD8) was tagged with an N-terminal triple Myc epitope right after the signal peptide. ZNRF3 was tagged with a triple Myc epitope right after a signal peptide, or a C-terminal hemagglutinin (HA) epitope.

HEK293 cells stably expressing N-terminal Myc-tagged FZD8 were constructed by transfection. Most of the Myc-FZD8 in this cell line is cytoplasmic and only a small fraction of Myc-FZD8 is localized on the plasma membrane.

cellular domain, the inventors performed a phage display based antibody panning using purified ZNRF3 extracellular domain and standard techniques to identify antibodies that bind ZNRF3 extracellular domain and modulate ZNRF3 function.

Fc-ZNRF3 ECD (extracellular domain, amino acids 56-219 of SEQ ID NO: 1) protein was used for phage panning. Fragment antigen-binding (Fab) clones were screened by ELISA using Fc-ZNRF3 ECD and their binding to ZNRF3 was verified by FACS analysis using HEK293 cells stably expressing ZNRF3 ΔRING.

Figure 8:
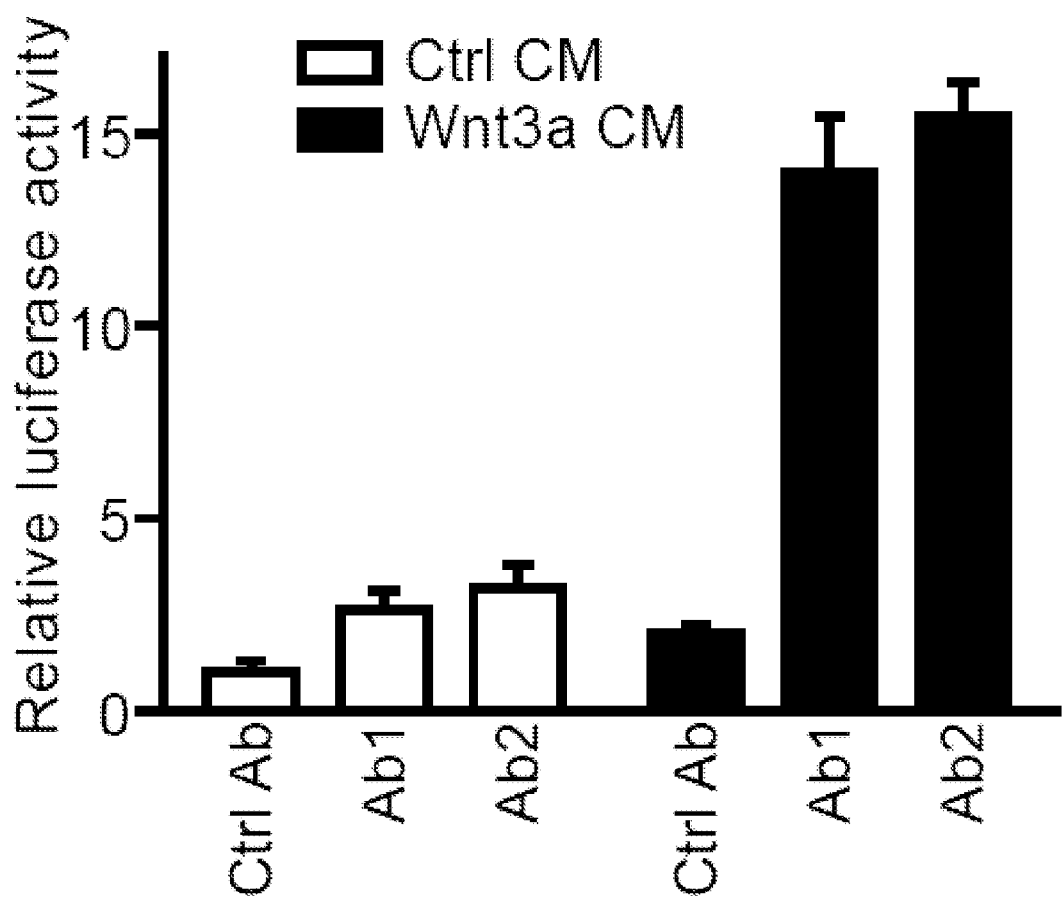
FIG. 8 is a set of bar graphs identifying two ZNRF3 hFabs that modulate Wnt signaling. In particular, the bar graphs show that ZNRF3 antibodies increase STF activity. HEK293-STF cells were treated with 50 μg/ml ZNRF3 antibody or control antibody in the absence and presence of 5% Wnt3a conditioned media overnight and subjected to STF luciferase reporter assay.

Two of the resulting antibodies (Fab clones Ab1 and Ab2) exhibited Wnt stimulating activity measured by STF reporter, even in the absence of exogenous Wnt3a addition. Additionally, FIG. 8 shows that the two antibodies enhanced Wnt3a-induced STF activity. The sequences of the antibodies are provided in SEQ. ID NO: 3 and SEQ ID NO: 4 (for Ab1) and in SEQ. ID NO: 5 and SEQ ID NO: 6 (for Ab2).

TABLE 4

Amino Acid Sequences of Light and heavy Chains for Fab Clones Ab1 and Ab2

| | |
|---|---|
| Ab1, Lch-lambda3 (SEQ. ID NO: 3) | DIELTQPPSV SVSPGQTASI TCSGDSIPSK YAHWYQQKPG QAPVLVIYGK SHRPSGIPER FSGSNSGNTA TLTISGTQAE DEADYYCAAW DLLGDGWVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab1, Hch-VH1B (SEQ. ID NO: 4) | QVQLVQSGAE VKKPGASVKV SCKASGYTFT SYHMHWVRQA PGQGLEWMGW INPYTGDTNY AQKFQGRVTM TRDTSISTAY MELSRLRSED TAVYYCAREK VYMDIWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSEF DYKDDDDKGA PHHHHHH |
| Ab2, Lch-lambda3 (SEQ. ID NO: 5) | DIELTQPPSV SVSPGQTASI TCSGDSLGSY YVHWYQQKPG QAPVLVIYRN KQRPSGIPER FSGSNSGNTA TLTISGTQAE DEADYYCQTY DWMYSSRVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab1, Hch-VH1B (SEQ. ID NO: 6) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFDYKDD DDKGAPHHHH HH |

A cell surface protein biotinylation assay revealed that ZNRF3 siRNA strongly increased the level of Myc-FZD8 on the plasma membrane without affecting the level of total Myc-FZD8. See, FIG. 7. The sources of primary antibodies were: anti-Myc tag (Cell Signaling Technology); and anti-tubulin (Sigma).

Further, ZNRF3 siRNA and ZNRF3 ΔRING increased, while wild-type ZNRF3 decreased, the membrane level of Myc-FZD8 as shown by flow cytometry. Using a pan-Frizzled antibody, we found that the cell surface level of endogenous Frizzled proteins was decreased or increased upon overexpression of wild-type ZNRF3 or ZNRF3 ΔRING, respectively.

Taken together, these results show that ZNRF3 regulates the level of Frizzled and LRP6 at the plasma membrane.

In summary, ZNRF3 and RNF43 are Wnt/β-catenin signaling targets and negative regulators of β-catenin and the Wnt signaling pathway.

Antagonizing antibodies to ZNRF3. Because ZNRF3 is localized at the cell surface and contains a conserved extra- Furthermore, the two antibodies modestly increased the level of LRP6 and membrane Myc-FZD8. These results further show that ZNRF3 inhibits Wnt signaling by decreasing the membrane level of Frizzled and LRP6.

Our results show that the two antibodies mimic the inhibition of ZNRF3 as shown above by siRNA knockdown and by expression of a dominant negative mutation of ZNRF3. These anti-ZNRF3 antibodies are antagonizing antibodies, since their activity is similar to ZNRF3 siRNA. Accordingly, these anti-ZNRF3 antibodies are antagonizing antibodies that increase Wnt signaling.

In addition, the inventors have selected Fab variants of Ab2 by affinity maturation according to a protocol provided by Morphosys. See, *HuCAL® Antibodies—Technical Manual* (2nd Edition, 2010), available for viewing at http://issuu.com/abdserotec/docs/hucal-manual 2nd-ed -highres. In brief, the inventors digested plasmids coding for the light chain Ab2 with restriction endonucleases and to remove sequences coding for LCDR3, added a LCDR3 cassette in the form of polynucleotides with random sequences in of a length that could code for an LCDR3 region, then religated the plasmid and the LCDR3 cassette to form an expression library that could express variant forms of light chains of Ab2. Using this library, variant Fabs of Ab2 (variant light chain and non-variant heavy chain), that bound to ZNRF3 were selected.

Likewise, the inventors digested plasmids coding for the heavy chain Ab2 with restriction endonucleases and to remove sequences coding for HCDR2, added a HCDR2 cassette in the form of polynucleotides with random sequences in of a length that could code for an HCDR2 region, then religated the plasmid and the HCDR2 cassette to form an expression library that could express variant forms of heavy chains of Ab2. For this library, the plasmid used had an HCDR1 cassette that differed from the HCDR1 of the unvaried heavy chain of Ab2. Using this library, variant Fabs of Ab2 (variant light chain and non-variant heavy chain), that bound to ZNRF3 were selected.

For the affinity maturation of the light chains, the LCDR3 domain was modified. Accordingly, the sequence of the LCDR3 of the light chain of Ab2 (SEQ ID NO: 39) differs from the LCDR3 of the light chain of the variants of Ab2, including 1F2(3_1B1) (SEQ ID NO: 93); 2A6(3_4 A10) (SEQ ID NO: 99); 2B7(3_4 G1) (SEQ ID NO: 105); 2B8 (4_3E10) (SEQ ID NO: 111); 2C9(4_4E3) (SEQ ID NO: 117); 2F5(3_4 A4) (SEQ ID NO: 123); and 2G6(3_4 D9) (SEQ ID NO: 129).

For the affinity maturation of the heavy chains, the HCDR2 domain was modified. Accordingly, the sequence of the HCDR2 of the heavy chain of Ab2 (SEQ ID NO: 41) differs from the HCDR3 of the heavy chain of the variants of Ab2, including and 2C1(2_3 A5) (SEQ ID NO: 137); 2D1(2_3 A7) (SEQ ID NO: 143); and 2H2(2_3H8) (SEQ ID NO: 149).

Moreover, the sequence HCR1 of the heavy chain of Ab2 (SEQ ID NO: 40) differs from the HCDR3 of the heavy chain of the variants of Ab2 where the heavy chains were modified from the heavy chain of Ab2, including SEQ ID NO: 136, SEQ ID NO: 142, and SEQ ID NO: 148.

Some of the heavy chains of the variants of Ab2 contain a peptide that permits the heavy chains to dimerize in a manner somewhat similar to the dimeric quarternary protein structure of IgG proteins. See, *HuCAL® Antibodies—Technical Manual* (2nd Edition, 2010), available for viewing at http://issuu.com/abdserotec/docs/hucal-manual_2nd-ed_-highres. See also, the pamphlet "Choosing the Best HuCAL® Antibody Format", available from AbD Serotec, a division of Morphosys at www.abdserotec.com/HuCAL. Accordingly, the heavy chains containing the peptide are referred to herein as "Hch-dimer".

The variants of Ab2 specifically bind to ZNRF3 in unpurified lysates as well or better than the parental Ab2 in an ELISA assay. The amino acid sequences of the light chains and heavy chains of the Ab2 variants are shown in TABLE 5.

TABLE 5

Amino Acid Sequences of Light and Heavy Chains for Fab Variants of Ab2

| | |
|---|---|
| Ab2, Lch-lambda3, variant 1F2(3_1B1) (SEQ. ID NO: 67) | DIELTQPPSV SVSPGQTASI TCSGDSLGSY YVHWYQQKPG QAPVLVIYRN KQRPSGIPER FSGSNSGNTA TLTISGTQAE DEADYYCQTF DSQAVTNVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch-VH1B, variant 1F2(3_1B1) (SEQ. ID NO: 68) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFDYKD DDDKGAPHHHH HH |
| Ab2, Lch-lambda3, variant 2A6(3_4A10) (SEQ. ID NO: 69) | DIELTQPPSV SVSPGQTASI TCSGDSLGSY YVHWYQQKPG QAPVLVIYRN KQRPSGIPER FSGSNSGNTA TLTISGTQAE DEADYYCQTF DSQAVTNVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2A6(3_4A10) (SEQ ID NO: 70) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2B7(3_4G1) (SEQ. ID NO: 71) | DIELTQPPSV SVSPGQTASI TCSGDSLGSY YVHWYQQKPG QAPVLVIYRN KQRPSGIPER FSGSNSGNTA TLTISGTQAE DDADYYCATY DSSSWWNVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |

TABLE 5-continued

Amino Acid Sequences of Light and Heavy Chains for Fab Variants of Ab2

| | |
|---|---|
| Ab2, Hch dimer, variant 2B7(3_4G1) (SEQ ID NO: 72) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2B8(4_3E10) (SEQ. ID NO: 73) | DIELTQPPSV SVSPGQTASI TCSGDSLGSY YVHWYQQKPG QAPVLVIYRN KQRPSGIPER FSGSNSGNTA TLTISGTQAE DEADYYCQTW DWWARHWVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2B8(4_3E10) (SEQ ID NO: 74) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2C9(4_4E3) (SEQ. ID NO: 75) | DIELTQPPSV SVSPGQTASI TCSGDSLGSY YVHWYQQKPG QAPVLVIYRN KQRPSGIPER FSGSNSGNTA TLTISGTQAE DEADYYCASY TSPINVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE A |
| Ab2, Hch dimer, variant 2C9(4_4E3) (SEQ ID NO: 76) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2F5(3_4A4) (SEQ. ID NO: 77) | DIELTQPPSV SVSPGQTASI TCSGDSLGSY YVHWYQQKPG QAPVLVIYRN KQRPSGIPER FSGSNSGNTA TLTISGTQAE DDADYYCAVW DDEPHHDVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2F5(3_4A4) (SEQ ID NO: 78) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2G6(3_4D9) (SEQ. ID NO: 79) | DIELTQPPSV SVSPGQTASI TCSGDSLGSY YVHWYQQKPG QAPVLVIYRN KQRPSGIPER FSGSNSGNTA TLTISGTQAE DDADYYCQTY DSLKFSRVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |

TABLE 5-continued

Amino Acid Sequences of Light and Heavy Chains for Fab Variants of Ab2

| | |
|---|---|
| Ab2, Hch dimer, variant 2G6(3_4D9) (SEQ ID NO: 80) | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2C1(2_3A5) (SEQ ID NO: 81) | DIELTQPPSV SVSPGQTASI TCSGDSLGSY YVHWYQQKPG QAPVLVIYRN KQRPSGIPER FSGSNSGNTA TLTISGTQAE DEADYYCQTY DWMYSSRVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2C1(2_3A5) (SEQ. ID NO: 82) | EVQLVESGGG LVKPGGSLRL SCAASGFTFS NAWMSWVRQA PGKGLEWVGH IKSSNMGGAA QYAASVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2D1(2_3A7) (SEQ ID NO: 83) | DIELTQPPSV SVSPGQTASI TCSGDSLGSY YVHWYQQKPG QAPVLVIYRN KQRPSGIPER FSGSNSGNTA TLTISGTQAE DEADYYCQTY DWMYSSRVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2D1(2_3A7) (SEQ. ID NO: 84) | EVQLVESGGG LVKPGGSLRL SCAASGFTFS NAWMSWVRQA PGKGLEWVGF TKNEVGGYTT EYAASVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |
| Ab2, Lch-lambda3, variant 2H2(2_3H8) (SEQ ID NO: 85) | DIELTQPPSV SVSPGQTASI TCSGDSLGSY YVHWYQQKPG QAPVLVIYRN KQRPSGIPER FSGSNSGNTA TLTISGTQAE DEADYYCQTY DWMYSSRVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TEA |
| Ab2, Hch dimer, variant 2H2(2_3H8) (SEQ. ID NO: 86) | EVQLVESGGG LVKPGGSLRL SCAASGFTFS NAWMSWVRQA PGKGLEWVGR IKAFKEGYIT QYAASVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSEFPKPST PPGSSGELEE LLKHLKELLK GPRKGELEEL LKHLKELLKG GSGGAPEQKL ISEEDLNDAP HHHHHH |

The inventors had the anti-ZNRF3 Fabs (Ab1 and Ab2) converted to a human IgG1 LALA format. The conversion was performed using a commercially available service from GeneWiz, which has a location at 19 Blackstone Street, Cambridge, Mass. 02139.

Figure 11:
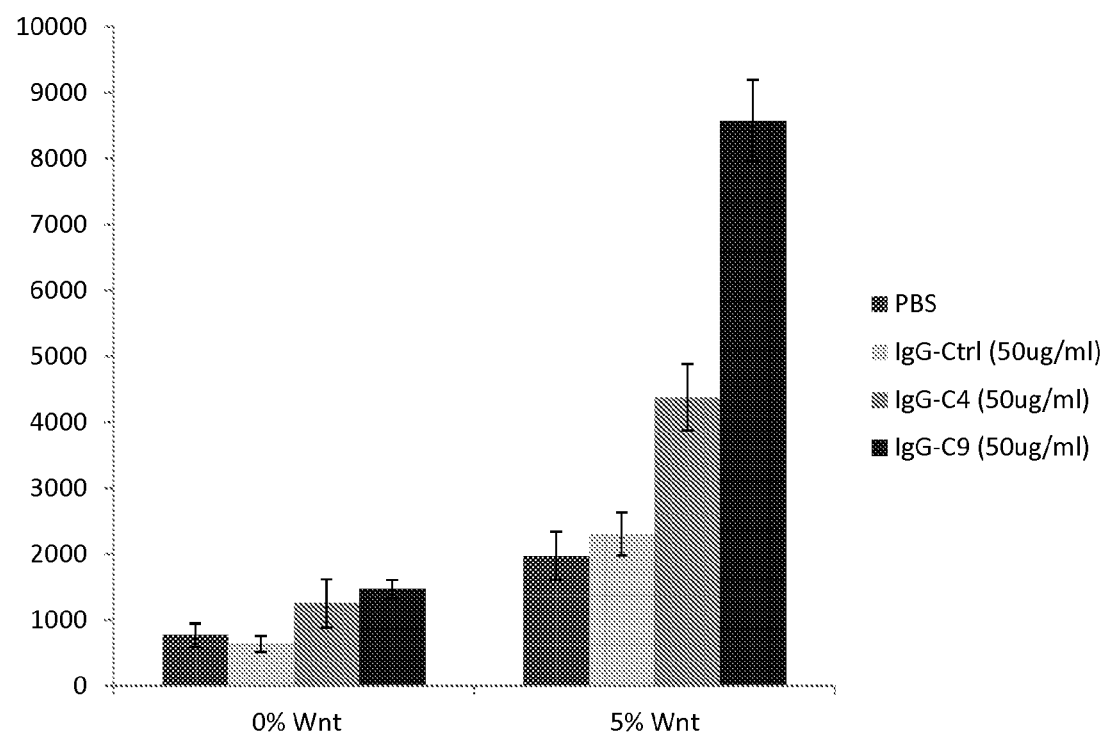
FIG. 11 is a bar graph showing the stimulatory effect of IgG-Ab1 and IgG-Ab2 in a SuperTopFlash® (STF) reporter assay.

The results of FIG. 11 show that the resulting IgGs (IgG-Ab1 and IgG-Ab2) retain the ZNRF3 antagonist activity as shown by a SuperTopFlash® (STF) reporter assay.

TABLE 6 shows the sequences of the human light and human heavy chains of IgG-Ab1 (h_Kappa_ZNRF3_Ab1_Lch and h_IgG1f_LALA_ZNRF3_Ab1_Hch) and IgG-Ab2 (h_Kappa_ZNRF3_Ab2_Lch and h_IgG1f_LALA_ZNRF3_Ab2_Hch).

The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs.

The term "antigen binding portion" of an antibody, as used herein, refers to one or more fragments of an intact antibody that retain the ability to specifically bind to a given antigen

TABLE 6

Amino Acid Sequences of anti-ZNRF3 Antibodies in a Human IgG1 LALA Format

| | |
|---|---|
| h_Kappa_ZNRF3_Ab1_Lch) (SEQ. ID NO: 87) The variable domain is from amino acids 1-110. The constant domain is from amino acids 111-214. | DIELTQPPSV SVSPGQTASI TCSGDSIPSK YAHWYQQKPG QAPVLVIYGK SHRPSGIPER FSGSNSGNTA TLTISGTQAE DEADYYCAAW DLLGDGWVFG GGTKLTVLGQ PKAAPSVTLF PPSSEELQAN KATLVCLISD FYPGAVTVAW KGDSSPVKAG VETTTPSKQS NNKYAASSYL SLTPEQWKSH RSYSCQVTHE GSTVEKTVAP TECS |
| h_IgG1f_LALA_ZNRF3_Ab1_Hch) (SEQ. ID NO: 88) The variable domain is from amino acids 1-116. The 3 constant domains are from amino acids 117-229, 230-339 and 340-446. | QVQLVQSGAE VKKPGASVKV SCKASGYTFT SYHMHWVRQA PGQGLEWMGW INPYTGDTNY AQKFQGRVTM TRDTSISTAY MELSRLRSED TAVYYCAREK VYMDIWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKRVEPKSCD KTHTCPPCPA PEAAGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| h_Kappa_ZNRF3_Ab2_Lch) (SEQ. ID NO: 89) The variable domain is from amino acids 1-110. The constant domain is from amino acids 111-214. | DIELTQPPSV SVSPGQTASI TCSGDSLGSY YVHWYQQKPG QAPVLVIYRN KQRPSGIPER FSGSNSGNTA TLTISGTQAE DEADYYCQTY DWMYSSRVFG GGTKLTVLGQ PKAAPSVTLF PPSSEELQAN KATLVCLISD FYPGAVTVAW KGDSSPVKAG VETTTPSKQS NNKYAASSYL SLTPEQWKSH RSYSCQVTHE GSTVEKTVAP TECS |
| h_IgG1f_LALA_ZNRF3_Ab2_Hch) (SEQ. ID NO: 90) The variable domain is from amino acids 1-121 The 3 constant domains are from amino acids 122-234, 235-344 and 345-451. | EVQLVESGGG LVKPGGSLRL SCAASGFTFS DYGIHWVRQA PGKGLEWVGR IKSKTDGGIT EYAAPVKGRF TISRDDSKNT LYLQMNSLKT EDTAVYYCAR AIYYLEAFDV WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKRVE PKSCDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |

Antibody production methods. Various types of antibodies to ZNRF3 or RNF43 can be produced by known methods of producing antibodies having a specified binding, as described below.

Definitions. Unless defined otherwise, all technical and scientific terms used herein have the same meaning as commonly understood by those of ordinary skill in the immunological art.

The term "antibody" as used herein includes whole antibodies and any antigen binding fragment (i.e., "antigen-binding portion") or single chains thereof. A naturally occurring antibody usually has at least two heavy (H) chains and two light (L) chains inter-connected by disulfide bonds. Each heavy chain is comprised of a heavy chain variable region (abbreviated herein as VH) and a heavy chain constant region.

(e.g., the extracellular regions of ZNRF or RNF43). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment, which consists of a VH domain or a VL domain; and an isolated complementarity determining region (CDR). (Ward et al., *Nature* 341:544-546 (1989).

The two domains of the Fv fragment, VL and VH, can be joined, using recombinant methods, by an artificial peptide linker that enables them to be made as a single protein chain in which the VL and VH regions pair to form monovalent antibodies and fragments thereof, known as single chain Fv (scFv). See, e.g., Bird et al., *Science* 242:423-426 (1988) and Huston et al., *Proc. Natl. Acad. Sci.* 85:5879-5883 (1988). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv. See, e.g., Hollinger and Hudson, *Nature Biotechnology* 23, 9, 1126-1136 (2005). Antigen binding portions of antibodies can be grafted into scaffolds based on polypeptides such as fibronectin type III (Fn3). See, U.S. Pat. No. 6,703,199, which describes fibronectin polypeptide monobodies.

Antigen binding portions can be incorporated into single chain antibodies and fragments thereof comprising a pair of tandem Fv segments (VH-CH1-VH-CH1) which, together with complementary light chain polypeptides, form a pair of antigen binding regions. Zapata et al., *Protein Eng.* 8(10): 1057-1062 (1995); and U.S. Pat. No. 5,641,870.

The term "binding specificity" as used herein refers to the ability of an individual antibody combining site to react with only one antigenic determinant. The combining site of the antibody is located in the Fab portion of the antibodies or fragment thereof and is constructed from the hypervariable regions of the heavy and light chains. Thus the invention provides a range of antibody structures by which an antibody "binds specifically" to the extracellular domain of ZNRF3 and a range of antibody structures by which an antibody "binds specifically" to the extracellular domain of RNF43.

The term "chimeric antibody" means an antibodies or fragment thereof in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The terms "complementarity determining region," and "CDR," as used herein refer to the sequences of amino acids within antibody variable regions which confer antigen specificity and binding affinity. In general, there are three CDRs (CDR1, CDR2 and CDR3) in each light chain variable region and three CDRs (CDR1, CDR2 and CDR3) in each heavy chain variable region.

The precise amino acid sequence boundaries of a given CDR can be readily determined using any of a number of well-known schemes, including those described by Kabat et al., *Sequences of Proteins of Immunological Interest*, 5th Edition (Public Health Service, National Institutes of Health, Bethesda, Md., 1991) ("Kabat" numbering method) or by Al-Lazikani et al., *J. Mol. Biol.* 273, 927-948 (1997) ("Chothia" numbering method).

As an example of how the determination of the amino acid sequence boundaries of a given CDR can be performed, TABLE 7 provides the CDRs for the light chains and heavy chains of Ab1 (SEQ ID NOS: 3 and 4) and Ab2 (SEQ ID NOS: 5 and 6). The inventors made the initial determination of the Kabat sequence for the CDRs for the light chains and the heavy chains of Ab1 and Ab2 (SEQ ID NOS: 31-42, "initial") using an alignment method similar to that provided by Dr. Andrew C R Martin's Group at the University College of London at www.bioinf.org.uk/abs/. Other information and alignment methods useful to make an initial determination of the Kabat sequences for CDRs are provided by the MRC Centre for Protein Engineering at http://vbase.mrc-cpe.cam.ac.uk/ and by the THE INTERNATIONAL IMMUNOGENETICS INFORMATION SYSTEM® at http://www.imgt.org/.

TABLE 7 also shows an updated determination of the CDRs for the light chains and the heavy chains of Ab1 and Ab2 (SEQ ID NOS: 43-54, "Kabat"), performed by the Kabat numbering method. TABLE 7 further shows an updated determination of the CDRs for the light chains and the heavy chains of Ab1 and Ab2 (SEQ ID NOS: 55-66, "Chothia"), performed by the Chothia numbering method.

TABLE 7

Amino Acid Sequences for CDRs of Ab1 and Ab2

| SEQ ID NO. | Antibody Chain | Amino Acids | CDR | Sequence | Method of determination |
|---|---|---|---|---|---|
| 31 | Ab1, LC | 23-33 | LCDR1 | SGDSIPSKYAH | initial |
| 32 | Ab1, LC | 45-55 | LCDR2 | LVIYGKSHRPS | initial |
| 33 | Ab1, LC | 88-97 | LCDR3 | AAWDLLGDGW | initial |
| 34 | Ab1, HC | 27-35 | HCDR1 | YTFTSYHMH | initial |
| 35 | Ab1, HC | 50-67 | HCDR2 | WINPYTGDTNYAQKFQGR | initial |
| 36 | Ab1, HC | 100-106 | HCDR3 | KVYMDIW | initial |
| 37 | Ab2 LC | 23-33 | LCDR1 | SGDSLGSYYVH | initial |
| 38 | Ab2 LC | 45-55 | LCDR2 | LVIYRNKQRPS | initial |
| 39 | Ab2 LC | 88-97 | LCDR3 | QTYDWMYSSR | initial |

TABLE 7-continued

Amino Acid Sequences for CDRs of Ab1 and Ab2

| SEQ ID NO. | Antibody Chain | Amino Acids | CDR | Sequence | Method of determination |
|---|---|---|---|---|---|
| 40 | Ab2 HC | 27-35 | HCDR1 | FTFSDYGIH | initial |
| 41 | Ab2 HC | 50-68 | HCDR2 | RIKSKTDGGITEYAAPVKG | initial |
| 42 | Ab2 HC | 101-110 | HCDR3 | AIYYLEAFDV | initial |
| 43 | Ab1, LC | 23-33 | LCDR1 | SGDSIPSKYAH | Kabat |
| 44 | Ab1, LC | 49-55 | LCDR2 | GKSHRPS | Kabat |
| 45 | Ab1, LC | 88-98 | LCDR3 | AAWDLLGDGWV | Kabat |
| 46 | Ab1, HC | 31-35 | HCDR1 | SYHMH | Kabat |
| 47 | Ab1, HC | 50-66 | HCDR2 | WINPYTGDTNYAQKFQG | Kabat |
| 48 | Ab1, HC | 99-105 | HCDR3 | EKVYMDI | Kabat |
| 49 | Ab2 LC | 23-33 | LCDR1 | SGDSLGSYYVH | Kabat |
| 50 | Ab2 LC | 49-55 | LCDR2 | RNKQRPS | Kabat |
| 51 | Ab2 LC | 88-98 | LCDR3 | QTYDWMYSSRV | Kabat |
| 52 | Ab2 HC | 31-35 | HCDR1 | DYGIH | Kabat |
| 53 | Ab2 HC | 50-68 | HCDR2 | RIKSKTDGGITEYAAPVKG | Kabat |
| 54 | Ab2 HC | 101-110 | HCDR3 | AIYYLEAFDV | Kabat |
| 55 | Ab1, LC | 25-31 | LCDR1 | DSIPSKY | Chothia |
| 56 | Ab1, LC | 49-51 | LCDR2 | GKS | Chothia |
| 57 | Ab1, LC | 90-97 | LCDR3 | WDLLGDGW | Chothia |
| 58 | Ab1, HC | 26-32 | HCDR1 | GYTFTSY | Chothia |
| 59 | Ab1, HC | 52-57 | HCDR2 | NPYTGD | Chothia |
| 60 | Ab1, HC | 99-105 | HCDR3 | EKVYMDI | Chothia |
| 61 | Ab2 LC | 25-31 | LCDR1 | DSLGSYY | Chothia |
| 62 | Ab2 LC | 49-51 | LCDR2 | RNK | Chothia |
| 63 | Ab2 LC | 90-97 | LCDR3 | YDWMYSSR | Chothia |
| 64 | Ab2 HC | 26-32 | HCDR1 | GFTFSDY | Chothia |
| 65 | Ab2 HC | 52-59 | HCDR2 | KSKTDGGI | Chothia |
| 66 | Ab2 HC | 101-110 | HCDR3 | AIYYLEAFDV | Chothia |

LC = Lch-lambda3
HC = Hch-VH1B

In addition, the CDR sequences for the Fab variants of Ab2 (see, TABLE 5) were calculated, using the method described above for determining the Kabat sequence by the "initial" method of determination. TABLE 8 shows the CDR sequences and the locations of the amino acids in the light or heavy chains.

TABLE 8

Amino Acid Sequences for CDRs of Variants of Ab2

| SEQ ID NO. | Antibody Chain | Amino Acids | CDR | Sequence | Method of determination |
|---|---|---|---|---|---|
| 91 | Ab2, LC, 1F2 | 23-33 | LCDR1 | SGDSLGSYYVH | initial |
| 92 | Ab2, LC, 1F2 | 45-55 | LCDR2 | LVIYRNKQRPS | initial |
| 93 | Ab2, LC, 1F2 | 88-97 | LCDR3 | QTFDSQAVTN | initial |

TABLE 8-continued

Amino Acid Sequences for CDRs of Variants of Ab2

| SEQ ID NO. | Antibody Chain | Amino Acids | CDR | Sequence | Method of determination |
|---|---|---|---|---|---|
| 94 | Ab2, HC, 1F2 | 26-35 | HCDR1 | FTFSDYGIH | initial |
| 95 | Ab2, HC, 1F2 | 50-68 | HCDR2 | RIKSKTDGGITEYAAPVKG | initial |
| 96 | Ab2, HC, 1F2 | 101-110 | HCDR3 | AIYYLEAFDV | initial |
| 97 | Ab2, LC, 2A6 | 23-33 | LCDR1 | SGDSLGSYYVH | initial |
| 98 | Ab2, LC, 2A6 | 45-55 | LCDR2 | LVIYRNKQRPS | initial |
| 99 | Ab2, LC, 2A6 | 88-97 | LCDR3 | QTFDSQAVTN | initial |
| 100 | Ab2, HC, 2A6 | 26-35 | HCDR1 | FTFSDYGIH | initial |
| 101 | Ab2, HC, 2A6 | 50-68 | HCDR2 | RIKSKTDGGITEYAAPVKG | initial |
| 102 | Ab2, HC, 2A6 | 101-110 | HCDR3 | AIYYLEAFDV | initial |
| 103 | Ab2, LC, 2B7 | 23-33 | LCDR1 | SGDSLGSYYVH | initial |
| 104 | Ab2, LC, 2B7 | 45-55 | LCDR2 | LVIYRNKQRPS | initial |
| 105 | Ab2, LC, 2B7 | 88-97 | LCDR3 | ATYDSSSWWN | initial |
| 106 | Ab2, HC, 2B7 | 26-35 | HCDR1 | FTFSDYGIH | initial |
| 107 | Ab2, HC, 2B7 | 50-68 | HCDR2 | RIKSKTDGGITEYAAPVKG | initial |
| 108 | Ab2, HC, 2B7 | 101-110 | HCDR3 | AIYYLEAFDV | initial |
| 109 | Ab2, LC, 2B8 | 23-33 | LCDR1 | SGDSLGSYYVH | initial |
| 110 | Ab2, LC, 2B8 | 45-55 | LCDR2 | LVIYRNKQRPS | initial |
| 111 | Ab2, LC, 2B8 | 88-97 | LCDR3 | QTWDWWARHW | initial |
| 112 | Ab2, HC, 2B8 | 27-35 | HCDR1 | FTFSDYGIH | initial |
| 113 | Ab2, HC, 2B8 | 50-68 | HCDR2 | RIKSKTDGGITEYAAPVKG | initial |
| 114 | Ab2, HC, 2B8 | 101-110 | HCDR3 | AIYYLEAFDV | initial |
| 115 | Ab2, LC, 2C9 | 23-33 | LCDR1 | SGDSLGSYYVH | initial |
| 116 | Ab2, LC, 2C9 | 45-55 | LCDR2 | LVIYRNKQRPS | initial |
| 117 | Ab2, LC, 2C9 | 88-95 | LCDR3 | ASYTSPIN | initial |
| 118 | Ab2, HC, 2C9 | 26-35 | HCDR1 | FTFSDYGIH | initial |
| 119 | Ab2, HC, 2C9 | 50-68 | HCDR2 | RIKSKTDGGITEYAAPVKG | initial |
| 120 | Ab2, HC, 2C9 | 101-110 | HCDR3 | AIYYLEAFDV | initial |
| 121 | Ab2, LC, 2F5 | 23-33 | LCDR1 | SGDSLGSYYVH | initial |
| 122 | Ab2, LC, 2F5 | 45-55 | LCDR2 | LVIYRNKQRPS | initial |
| 123 | Ab2, LC, 2F5 | 88-97 | LCDR3 | AVWDDEPHHD | initial |
| 124 | Ab2, HC, 2F5 | 26-35 | HCDR1 | FTFSDYGIH | initial |
| 125 | Ab2, HC, 2F5 | 50-68 | HCDR2 | RIKSKTDGGITEYAAPVKG | initial |
| 126 | Ab2, HC, 2F5 | 101-110 | HCDR3 | AIYYLEAFDV | initial |
| 127 | Ab2, LC, 2G6 | 23-33 | LCDR1 | SGDSLGSYYVH | initial |
| 128 | Ab2, LC, 2G6 | 45-55 | LCDR2 | LVIYRNKQRPS | initial |
| 129 | Ab2, LC, 2G6 | 88-97 | LCDR3 | QTYDSLKFSR | initial |
| 130 | Ab2, HC, 2G6 | 26-35 | HCDR1 | FTFSDYGIH | initial |

TABLE 8-continued

Amino Acid Sequences for CDRs of Variants of Ab2

| SEQ ID NO. | Antibody Chain | Amino Acids | CDR | Sequence | Method of determination |
|---|---|---|---|---|---|
| 131 | Ab2, HC, 2G6 | 50-68 | HCDR2 | RIKSKTDGGITEYAAPVKG | initial |
| 132 | Ab2, HC, 2G6 | 101-110 | HCDR3 | AIYYLEAFDV | initial |
| 133 | Ab2, LC, 2C1 | 23-33 | LCDR1 | SGDSLGSYYVH | initial |
| 134 | Ab2, LC, 2C1 | 45-55 | LCDR2 | LVIYRNKQRPS | initial |
| 135 | Ab2, LC, 2C1 | 88-97 | LCDR3 | QTYDWMYSSR | initial |
| 136 | Ab2, HC, 2C1 | 26-35 | HCDR1 | FTFSNAWMS | initial |
| 137 | Ab2, HC, 2C1 | 50-68 | HCDR2 | HIKSSNMGGAAQYAASVKG | initial |
| 138 | Ab2, HC, 2C1 | 101-110 | HCDR3 | AIYYLEAFDV | initial |
| 139 | Ab2, LC, 2D1 | 23-33 | LCDR1 | SGDSLGSYYVH | initial |
| 140 | Ab2, LC, 2D1 | 45-55 | LCDR2 | LVIYRNKQRPS | initial |
| 141 | Ab2, LC, 2D1 | 88-97 | LCDR3 | QTYDWMYSSR | initial |
| 142 | Ab2, HC, 2D1 | 26-35 | HCDR1 | FTFSNAWMS | initial |
| 143 | Ab2, HC, 2D1 | 50-68 | HCDR2 | FTKNEVGGYTTEYAASVKG | initial |
| 144 | Ab2, HC, 2D1 | 101-110 | HCDR3 | AIYYLEAFDV | initial |
| 145 | Ab2, LC, 2H2 | 23-33 | LCDR1 | SGDSLGSYYVH | initial |
| 146 | Ab2, LC, 2H2 | 45-55 | LCDR2 | LVIYRNKQRPS | initial |
| 147 | Ab2, LC, 2H2 | 88-97 | LCDR3 | QTYDWMYSSR | initial |
| 148 | Ab2, HC, 2H2 | 26-35 | HCDR1 | FTFSNAWMS | initial |
| 149 | Ab2, HC, 2H2 | 50-68 | HCDR2 | RIKAFKEGYITQYAASVKG | initial |
| 150 | Ab2, HC, 2H2 | 101-110 | HCDR3 | AIYYLEAFDV | initial |

LC = Lch-lambda3
HC = Hch-VH1B or Hch dimer

In addition, the CDR regions for the anti-ZNRF3 Antibodies in IgG Format were calculated, using the method described above for determining the Kabat sequence by the "initial" method of determination. TABLE 9 shows the sequences and the locations of the amino acids in the light or heavy chains.

TABLE 9

Amino Acid Sequences for CDRs of anti-ZNRF3 Antibodies in IgG Format

| SEQ ID NO. | Antibody Chain | Amino Acids | CDR | Sequence | Method of determination |
|---|---|---|---|---|---|
| 151 | h_Kappa_ZNRF3_Ab1_Lch | 23-33 | LCDR1 | SGDSIPSKYAH | initial |
| 152 | h_Kappa_ZNRF3_Ab1_Lch | 45-55 | LCDR2 | LVIYGKSHRPS | initial |
| 153 | h_Kappa_ZNRF3_Ab1_Lch | 87-96 | LCDR3 | AAWDLLGDG | initial |
| 154 | h_IgG1f_LALA_ZNRF3_Ab1Hch | 27-35 | HCDR1 | TFTSYHMH | initial |
| 155 | h_IgG1f_LALA_ZNRF3_Ab1Hch | 50-66 | HCDR2 | WINPYTGDTNYAQKFQG | initial |

TABLE 9-continued

Amino Acid Sequences for CDRs of anti-ZNRF3 Antibodies in IgG Format

| SEQ ID NO. | Antibody Chain | Amino Acids | CDR | Sequence | Method of determination |
|---|---|---|---|---|---|
| 156 | h_IgG1f_LALA_ZNRF3_Ab1Hch | 99-105 | HCDR3 | EKVYMDI | initial |
| 157 | h_Kappa_ZNRF3_Ab2_Lch | 23-33 | LCDR1 | SGDSLGSYYVH | initial |
| 158 | h_Kappa_ZNRF3_Ab2_Lch | 45-55 | LCDR2 | LVIYRNKQRPS | initial |
| 159 | h_Kappa_ZNRF3_Ab2_Lch | 87-96 | LCDR3 | QTYDWMYSSR | initial |
| 160 | h_IgG1f_LALA_ZNRF3_Ab2_Hch | 27-35 | HCDR1 | FTFSDYGIH | initial |
| 161 | h_IgG1f_LALA_ZNRF3_Ab2_Hch | 50-68 | HCDR2 | RIKSKTDGGITEYAAPVKG | initial |
| 162 | h_IgG1f_LALA_ZNRF3_Ab2_Hch | 101-110 | HCDR3 | AIYYLEAFDV | initial |

LC = human Kappa
HC = human IgG1f LALA

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984). In some embodiments, the term "conservative sequence modifications" are used to refer to amino acid modifications that do not significantly affect or alter the binding characteristics of the antibody containing the amino acid sequence.

The terms "cross-block", "cross-blocked" and "cross-blocking" are used interchangeably herein to mean the ability of an antibody or other binding agent to interfere with the binding of other ligands (such as R-spondin) in a standard competitive binding assay. The ability or extent to which an antibody or other binding agent is able to interfere with the binding of another ligand, and therefore whether it can be said to cross-block according to the invention, can be determined using standard competition binding assays. One suitable assay involves the use of the Biacore technology (e.g. by using the BIAcore 3000® instrument (Biacore, Uppsala, Sweden)), which can measure the extent of interactions using surface plasmon resonance technology. Another assay for measuring cross-blocking uses an ELISA-based approach.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. For the antibodies of the invention, the epitope may be or may be on the extracellular domain of ZNRF3 or RNF43. In one embodiment, the epitope is on the extracellular domain of vertebrate ZNRF3 or RNF43, for example zebrafish, *Xenopus*, murine or human ZNRF3 or RNF43. In a more specific embodiment, the epitope is on the extracellular domain of human or cynomolgus ZNRF3 or RNF43, or both human and cynomolgus ZNRF3 or RNF43.

The term "genetically engineered" refers to the alteration of the structure of genetic material in a living organism by human intervention, through the production and use of recombinant DNA techniques and the expression of polypeptides from the recombinant DNA. Techniques for the use of recombinant DNA and the expression of polypeptides are known to those of skill in the art. Techniques for the production of a genetically engineered antibody or antibody fragment of the invention are described in the references provided herein. See, e.g., Bird et al., *Science* 242:423-426 (1988) and Huston et al., *Proc. Natl. Acad. Sci.* 85:5879-5883 (1988).

See also, e.g., Riechmann L et al., *Nature* 332:323-327 (1998); Jones P et al., *Nature* 321:522-525 (1986); Queen C et al., *Proc. Natl. Acad., U.S.A.* 86:10029-10033 (1989); U.S. Pat. No. 5,225,539 to Winter, and U.S. Pat. Nos. 5,530,101; 5,585,089; 5,693,762 and 6,180,370 to Queen et al.).

The term "human antibody" includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., *Proc. Natl. Acad. Sci. USA*, 81:6851-6855, (1984); Morrison and Oi, *Adv. Immunol.*, 44:65-92 (1988); Verhoeyen et al., *Science*, 239:1534-1536, (1988); Padlan, *Molec. Immun.*, 28:489-498 (1991); and Padlan, *Molec. Immun.*, 31:169-217 (1994). Another example of human engineering technology is the Xoma technology disclosed in U.S. Pat. No. 5,766,886.

The term "isolated antibody" refers to an antibody that is substantially free of other antibodies having different antigenic specificities (e.g., an isolated antibody that specifically binds to ZNRF3 or RNF43 is substantially free of antibodies that specifically bind antigens other than ZNRF3 or RNF43). An isolated antibody that specifically binds to the protein of interest may, however, have cross-reactivity to other antigens. Moreover, an isolated antibody may be substantially free of other cellular material and/or chemicals.

The term "isotype" refers to the antibody class (e.g., IgM, IgE, and IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. For examples of anti-ZNRF3 antibodies in the IgG format, see TABLE 6.

The terms "monoclonal antibody" or "monoclonal antibody composition" as used herein refer to a preparation of antibodies of single molecular composition. A monoclonal antibody composition displays a single binding specificity and affinity for a particular epitope.

The term "vector" is intended to refer to a polynucleotide capable of transporting another polynucleotide to which it has been linked.

Antibodies with conservative modifications. In certain embodiments, an antibody of the invention has a heavy chain variable region comprising CDR1, CDR2, and CDR3 sequences or a light chain variable region comprising CDR1, CDR2, and CDR3 sequences or both, wherein one or more of these CDR sequences have specified amino acid sequences based on the antibodies described herein or conservative modifications thereof, and wherein the antibodies retain the desired functional properties of the antibodies of the invention. See, SEQ ID NOS: 3-6 and the CDR sequences described therein, SEQ ID NOS: 67-86 and the CDR sequences described therein and SEQ ID NOS: 87-90 and the CDR sequences described therein. See also, SEQ ID NOS: 31-66 in TABLE 7, SEQ ID NOS: 91-150 in TABLE 8, and SEQ ID NOS: 151-162 in TABLE 9.

Accordingly, in several embodiments, the antibody or antigen binding fragment of the invention can be a polypeptide having three CDR regions arranged from the amino terminus of the polypeptide toward the carboxyl terminus, as is understood by those of skill in the immunological art.

In one embodiment, this antibody or antigen binding fragment of the invention has (a) the first region has a peptide sequence selected from a first region of having a peptide sequence selected from the group consisting of SEQ ID NO: 31; SEQ ID NO: 37; SEQ ID NO: 43; SEQ ID NO: 49; SEQ ID NO: 55; SEQ ID NO: 61; SEQ ID NO: 91; SEQ ID NO: 97; SEQ ID NO: 103; SEQ ID NO: 109; SEQ ID NO: 115; SEQ ID NO: 121; SEQ ID NO: 127; SEQ ID NO: 133; SEQ ID NO: 139; SEQ ID NO: 145; SEQ ID NO: 151 or SEQ ID NO: 157; (b) the second region has a peptide sequence selected from SEQ ID NO: 32; SEQ ID NO: 38; SEQ ID NO: 44; SEQ ID NO: 50; SEQ ID NO: 56; SEQ ID NO: 62; SEQ ID NO: 92; SEQ ID NO: 98; SEQ ID NO: 104; SEQ ID NO: 110; SEQ ID NO: 116; SEQ ID NO: 122; SEQ ID NO: 128; SEQ ID NO: 134; SEQ ID NO: 140; SEQ ID NO: 146; SEQ ID NO: 152; or SEQ ID NO: 158; and (c) the third region has a peptide sequence selected from SEQ ID NO: 33; SEQ ID NO: 39; SEQ ID NO: 45; SEQ ID NO: 51; SEQ ID NO: 57; SEQ ID NO: 63; SEQ ID NO: 93; SEQ ID NO: 99; SEQ ID NO: 105; SEQ ID NO: 111; SEQ ID NO: 117; SEQ ID NO: 123; SEQ ID NO: 129; SEQ ID NO: 135; SEQ ID NO: 141; SEQ ID NO: 147; SEQ ID NO: 153; or SEQ ID NO: 159. In a specific embodiment, this antibody or antigen binding fragment has one or more polypeptides with at least one of the polypeptides having the peptide sequences of the CDR regions of the three CDR regions selected as described in the preceding sentence. In a more specific embodiment, this polypeptide is a light chain of an antibody or an antibody fragment.

In another embodiment, this antibody or antigen binding fragment of the invention has (a) the first region has a peptide sequence selected SEQ ID NO: 34; SEQ ID NO: 40; SEQ ID NO: 46; SEQ ID NO: 52; SEQ ID NO: 58; SEQ ID NO: 64; SEQ ID NO: 94; SEQ ID NO: 100; SEQ ID NO: 106; SEQ ID NO: 112; SEQ ID NO: 118; SEQ ID NO: 124; SEQ ID NO: 130; SEQ ID NO: 136; SEQ ID NO: 142; SEQ ID NO: 148; SEQ ID NO: 154; or SEQ ID NO: 160; (b) the second region has a peptide sequence selected from SEQ ID NO: 35; SEQ ID NO: 41; SEQ ID NO: 47; SEQ ID NO: 53; SEQ ID NO: 59; SEQ ID NO: 65; SEQ ID NO: 95; SEQ ID NO: 101; SEQ ID NO: 107; SEQ ID NO: 113; SEQ ID NO: 119; SEQ ID NO: 125; SEQ ID NO: 131; SEQ ID NO: 137; SEQ ID NO: 143; SEQ ID NO: 149; SEQ ID NO: 155; or SEQ ID NO: 161; and (c) the third region has a peptide sequence selected from SEQ ID NO: 36; SEQ ID NO: 42; SEQ ID NO: 48; SEQ ID NO: 54; SEQ ID NO: 60; SEQ ID NO: 66; SEQ ID NO: 96; SEQ ID NO: 102; SEQ ID NO: 108; SEQ ID NO: 114; SEQ ID NO: 120; SEQ ID NO: 126; SEQ ID NO: 132; SEQ ID NO: 138; SEQ ID NO: 144; SEQ ID NO: 150; SEQ ID NO: 156; or SEQ ID NO: 162. In a specific embodiment, this antibody or antigen binding fragment has one or more polypeptides with at least one of the polypeptides having the peptide sequences of the CDR regions of the three CDR regions selected as described in the preceding sentence. In a more specific embodiment, this polypeptide is a heavy chain of an antibody or an antibody fragment.

In yet another embodiment, this antibody or antigen binding fragment of the invention has (a) the first region has a peptide sequence selected from the group consisting of SEQ ID NO: 31 and SEQ ID NO: 37; (b) the second region has a peptide sequence selected from the group consisting of SEQ ID NO: 32 and SEQ ID NO: 38; and (c) the third region has a peptide sequence selected from the group consisting of SEQ ID NO: 33 and SEQ ID NO: 39. In a specific embodiment, this antibody or antigen binding fragment has one or more polypeptides with at least one of the polypeptides having the peptide sequences of the CDR regions of the three CDR regions selected as described in the preceding sentence. In a more specific embodiment, this polypeptide is a light chain of an antibody or an antibody fragment.

In yet another embodiment, this antibody or antigen binding fragment of the invention has (a) the first region has a peptide sequence selected from the group consisting of SEQ ID NO: 34 and SEQ ID NO: 40; (b) the second region has a peptide sequence selected from the group consisting of SEQ ID NO: 35 and SEQ ID NO: 41; and (c) the third region has a peptide sequence selected from the group consisting of SEQ ID NO: 36 and SEQ ID NO: 42. In a specific embodiment, this antibody or antigen binding fragment has one or more polypeptides with at least one of the polypeptides having the peptide sequences of the CDR regions of the three CDR regions selected as described in the preceding sentence. In a more specific embodiment, this polypeptide is a heavy chain of an antibody or an antibody fragment.

For the amino acids in the antibody of the invention that are outside of the CDR regions, conservative amino acid substitutions can be made without altering the functional properties of the antibodies of the invention.

Accordingly, in several embodiments, the antibody or antigen binding fragment of the invention can be a polypeptide having a high degree of peptide sequence identity with a light chain or heavy chain polypeptide selected from Ab1, Ab2, variants of Ab2, IgG-Ab1 or IgG-Ab2, disclosed herein.

In one embodiment, this antibody or antigen binding fragment of the invention has at least 95% sequence identity to a sequence selected from SEQ ID NO: 3; SEQ ID NO: 5; SEQ ID NO: 67; SEQ ID NO: 69; SEQ ID NO: 71; SEQ ID NO: 73; SEQ ID NO: 75; SEQ ID NO: 77; SEQ ID NO: 79; SEQ ID NO: 81; SEQ ID NO: 83; or SEQ ID NO: 85. In a specific embodiment, this antibody or antigen binding fragment has one or more polypeptides with at least one of the polypeptides having at least 95% sequence identity to a sequence selected from SEQ ID NO: 3; SEQ ID NO: 5; SEQ ID NO: 67; SEQ ID NO: 69; SEQ ID NO: 71; SEQ ID NO: 73; SEQ ID NO: 75; SEQ ID NO: 77; SEQ ID NO: 79; SEQ ID NO: 81; SEQ ID NO: 83; or SEQ ID NO: 85. In a more specific embodiment, this polypeptide is a light chain of an antibody or an antibody fragment of an Fab.

In another embodiment, this antibody or antigen binding fragment of the invention has at least 95% sequence identity to a sequence selected from SEQ ID NO: 4; SEQ ID NO: 6; SEQ ID NO: 68; SEQ ID NO: 70; SEQ ID NO: 72; SEQ ID NO: 74; SEQ ID NO: 76; SEQ ID NO: 78; SEQ ID NO: 80; SEQ ID NO: 82; SEQ ID NO: 84; SEQ ID NO: 86; SEQ ID NO: 88; or SEQ ID NO: 90. In a specific embodiment, this antibody or antigen binding fragment has one or more polypeptides with at least one of the polypeptides having at least 95% sequence identity to a sequence selected from SEQ ID NO: 4; SEQ ID NO: 6; SEQ ID NO: 68; SEQ ID NO: 70; SEQ ID NO: 72; SEQ ID NO: 74; SEQ ID NO: 76; SEQ ID NO: 78; SEQ ID NO: 80; SEQ ID NO: 82; SEQ ID NO: 84; SEQ ID NO: 86; SEQ ID NO: 88; or SEQ ID NO: 90. In a more specific embodiment, this polypeptide is a heavy chain of an antibody or an antibody fragment of an Fab.

In one embodiment, this antibody or antigen binding fragment of the invention has at least 95% sequence identity to a sequence selected from SEQ ID NO: 87 or SEQ ID NO: 89. In a specific embodiment, this antibody or antigen binding fragment has one or more polypeptides with at least one of the polypeptides having at least 95% sequence identity to a sequence selected from SEQ ID NO: 87 or SEQ ID NO: 89. In a more specific embodiment, this polypeptide is a light chain of an antibody or an antibody fragment of an IgG.

In another embodiment, this antibody or antigen binding fragment of the invention has at least 95% sequence identity to a sequence selected from SEQ ID NO: 88 or SEQ ID NO: 90. In a specific embodiment, this antibody or antigen binding fragment has one or more polypeptides with at least one of the polypeptides having at least 95% sequence identity to a sequence selected from SEQ ID NO: 88 and SEQ ID NO: 90. In a more specific embodiment, this polypeptide is a heavy chain of an antibody or an antibody fragment of an IgG.

Antibodies that bind to the same epitope. The invention provides antibodies that bind to the ZNRF23 and RNF43. Additional antibodies can therefore be identified based on their ability to cross-compete (e.g., to competitively inhibit the binding of, in a statistically significant manner) with antibodies of the invention in binding assays. As used herein, an antibody "competes" for binding when the competing antibody inhibits binding of an antibody of the invention by more than 50%, in the presence of competing antibody concentrations higher than $10^6 \times K_D$ of the competing antibody.

Genetically engineered and modified antibodies. An antibody of the invention further can be prepared using an antibody having one or more of the VH and/or VL sequences shown herein as starting material to engineer a modified antibody, which modified antibody may have altered properties from the starting antibody. One type of variable region engineering that can be performed is CDR grafting. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann L et al., *Nature* 332:323-327 (1998); Jones P et al., *Nature* 321:522-525 (1986); Queen C et al., *Proc. Natl. Acad., U.S.A.* 86:10029-10033 (1989); U.S. Pat. No. 5,225,539 to Winter, and U.S. Pat. Nos. 5,530,101; 5,585,089; 5,693,762 and 6,180,370 to Queen et al.). Such framework sequences can be obtained from public DNA databases or published references that include germline antibody gene sequences. For example, germline DNA sequences for human heavy and light chain variable region genes can be found in the "VBase" human germline sequence database. See, Kabat et al., *Sequences of Proteins of Immunological Interest, Fifth Edition*, NIH Publication No. 91-3242 (U.S. Department of Health and Human Services, Bethesda Md., 1991); Tomlinson I M et al., *J. fol. Biol.* 227:776-798 (1992); and Cox J P L et al., *Eur. J Immunol.* 24:827-836 (1994).

Grafting antigen-binding domains into alternative frameworks or scaffolds. A wide variety of antibody/immunoglobulin frameworks or scaffolds can be employed so long as the resulting polypeptide includes at least one binding region which specifically binds to ZNRF3 or RNF43. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein (e.g., human and/or cynomolgus ZNRF3 or RNF43). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Nos. 2004/0175756; 2005/0053973; 2005/0048512; and 2006/0008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants. See, e.g., U.S. Pat. No. 5,831,012. Affibody molecules mimic antibodies have a molecular weight of about 6 kDa, while the usual molecular weight of antibodies is about 150 kDa.

Human or humanized antibodies. The invention provides fully human antibodies that specifically bind to a ZNRF3 or RNF43 protein (e.g., human and/or cynomolgus ZNRF3 or RNF43). Compared to the chimeric or humanized antibodies, the human ZNRF3 or RNF43-binding antibodies of the invention have further reduced antigenicity when administered to human subjects.

The human ZNRF3 or RNF43-binding antibodies can be generated using methods that are known in the art. For example, the humaneering technology used to converting non-human antibodies into genetically engineered human antibodies. U.S. Patent Publication No. 2005/0008625 describes an in vivo method for replacing a nonhuman antibody variable region with a human variable region in an antibody while maintaining the same or providing better binding characteristics relative to that of the nonhuman antibody. In addition, human ZNRF3 or RNF43-binding antibodies can also be commercially obtained from companies which customarily produce human antibodies, e.g., KaloBios, Inc. (Mountain View, Calif.).

Camelid antibodies. Antibody proteins obtained from members of the camel and dromedary (*Camelus bactrianus* and *Camelus dromaderius*) family including new world members such as llama species (*Lama glama, Vicugna pacos* and *Vicugna vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See, International Patent Application WO 94/04678, published 3 Mar. 1994. A region of the camelid antibody which is the small single variable domain identified as VHH can be obtained by genetic engineering to yield a small protein having high affinity for a target, resulting in a low molecular weight antibody-derived protein known as a "camelid nanobody". See, U.S. Pat. No. 5,759,808, issued Jun. 2, 1998. See also, Stijlemans B et al., *J Biol Chem* 279: 1256-1261 (2004); Dumoulin M et al., *Nature* 424: 783-788 (2003); Pleschberger M et al. *Bioconjugate Chem* 14: 440-448 (2003); Cortez-Retamozo V et al., *Int J Cancer* 89: 456-62 (2002); and Lauwereys M et al., EMBO J 17: 3512-3520 (1998). Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

Methods of Producing Antibodies of the Invention. In some embodiments, mammalian host cells are used to express and produce the antibodies of the invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various COS cell lines, HeLa cells, myeloma cell lines, transformed B-cells and hybridomas. The use of mammalian tissue cell culture to express polypeptides is discussed generally in, e.g., Winnacker, *From Genes to Clones* (VCH Publishers, N.Y., N.Y., 1987). Expression vectors for mammalian host cells can include expression control sequences, such as an origin of replication, a promoter, and an enhancer. See, e.g., Queen, et al., *Immunol. Rev.* 89:49-68 (1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Generation of monoclonal antibodies of the invention. Monoclonal antibodies (mAbs) can be produced by a variety of techniques, including conventional monoclonal antibody methodology e.g., the standard somatic cell hybridization technique of Kohler and Milstein, *Nature* 256: 495 (1975). Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art. See e.g., U.S. Pat. No. 4,816,567 to Cabilly et al. To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against ZNRF3 or RNF43 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci. See e.g., Lonberg, et al., *Nature* 368(6474): 856-859 (1994). Accordingly, the mice exhibit reduced expression of mouse IgM or κ, and in response to immunization, the introduced human heavy and light chain transgenes undergo class switching and somatic mutation to generate high affinity human IgGκ monoclonal. Lonberg, N., *Handbook of Experimental Pharmacology* 113: 49-101 (1994); Lonberg, N. and Huszar, D., *Intern. Rev. Immunol.* 13: 65-93 (1995), and Harding, F. and Lonberg, N., *Ann. N. Y. Acad. Sci.* 764:536-546 (1995). The preparation and use of HuMAb mice, and the genomic modifications carried by such mice, is further described in Taylor, L. et al., *Nucleic Acids Research* 20:6287-6295 (1992); Chen, J. et al., *International Immunology* 5: 647-656 (1993); Tuaillon et al., *Proc. Natl. Acad. Sci. USA* 94:3720-3724 (1993); Choi et al., *Nature Genetics* 4:117-123 (1993); Chen, J. et al., *EMBO J.* 12: 821-830 (1993); Tuaillon et al., *J. Immunol.* 152:2912-2920 (1994); Taylor, L. et al., *International Immunology* 579-591 (1994); and Fishwild, D. et al., Nature Biotechnology 14: 845-851 (1996. See further, U.S. Pat. Nos. 5,545,806; 5,569, 825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise antibodies of the invention. For example, mice carrying both a human heavy chain transchromosome and a human light chain tranchromosome, referred to as "TC mice" can be used; such mice are described in Tomizuka et al., *Proc. Natl. Acad. Sci. USA* 97:722-727 (2000). Furthermore, cows carrying human heavy and light chain transchromosomes have been described in the art and can be used to raise antibodies of the invention. Kuroiwa et al., *Nature Biotechnology* 20:889-894 (2002).

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc engineering. Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described. See, Shields R L et al., *J. Biol. Chem.* 276:6591-6604 (2001).

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell. See also, Shields, R. L. et al., *J. Biol. Chem.* 277:26733-26740 (2002). International Patent Application WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies. See also, Umana et al., *Nat. Biotech.* 17:176-180 (1999).

Inhibition of ZNRF3 enhances Wnt/β-catenin signaling and disrupts Wnt/PCP signaling in vivo. Frizzled proteins are required for both Wnt/β-catenin and Wnt/PCP signaling, and inhibition of ZNRF3 increases the membrane level of Frizzled proteins. Therefore, inhibition of ZNRF3 is expected to promote both Wnt/β-catenin and Wnt/PCP signaling. The inventors tested this hypothesis in model organisms.

First, overexpression of ZNRF3 ΔRING, but not wild-type ZNRF3, in zebrafish embryos resulted in loss of anterioneural structures, most prominently the eyes. Suppression of Wnt/β-catenin signaling in the anterior neuroectoderm is an important step for early neural patterning during gastrulation, and ectopic activation of β-catenin signaling results in loss of anterioneural structures.

Zebrafish were maintained using standard methods. Nusslein-Volhard C and Dahm R *Zebrafish. A practical approach.* (Oxford University Press, UK, 2002); Westerfield M *The zebrafish book: a guide for the laboratory use of zebrafish (Brachydanio rerio).* (University of Oregon Press, Eugene, Oreg., 1995).

In vitro transcription was performed to synthesize capped mRNA using linearized plasmids containing human ZNRF3, ZNRF3 ΔRING, and the GFP coding sequence as template using mMESSAGE mMACHINE kit (Ambion). For zebrafish, 200 pg of ZNRF3 WT mRNA or 400 pg of ZNRF3 ΔRING mRNAs were injected into the embryos at the 1-2-cell stage.

For in situ hybridization, embryos at indicated stages were fixed overnight in 4% paraformaldehyde/PBS. DIG-labeled antisense probes were generated and used according to standard protocols. Nusslein-Volhard C and Dahm R, *Zebrafish. A practical approach.* (Oxford University Press, UK, 2002).

Analysis of movements by cell tracking was performed as previously described by Gerdes et al., *Nature Genetics* 39, 1350 (2007). Briefly, 1 nL of 10,000-MW dextran-conjugated Alexa 488 lineage tracer (Invitrogen) was injected into the yolk just below the cells at 256 cell stage. The embryos with fluorescent clones in the dorsal region were observed for cell movements toward the midline of the embryo and extend along the anteroposterior axis. Live images were taken at 30% Epiboly, shield, and 75% Epiboly stages of the same embryos.

Second, overexpression of ZNRF3 ΔRING in *Xenopus* embryos led to axis duplication and increased expression of β-catenin target genes in animal caps.

Experiments using *Xenopus* embryos were as described previously. Goentoro L and Kirschner M W, "Evidence that fold-change, and not absolute level, of beta-catenin dictates Wnt signaling." *Mol. Cell* 36, 872-884 (2009).

In vitro transcription was performed to synthesize capped mRNA using linearized plasmids containing human ZNRF3, ZNRF3 ΔRING, and the GFP coding sequence as template using mMESSAGE mMACHINE kit (Ambion). For *Xenopus*, 200 pg of either ZNRF3 WT or ZNRF3 ΔRING mRNA as well as GFP control mRNA were injected in to 2 blastomeres in 4-cell stage embryos at the marginal zone.

To analyze the expression pattern of *Xenopus* Znrf3, total RNA was extracted from embryos at different stages. Quantitative PCR was performed on this cDNA using Applied Biosystems SYBR-Green Master Mix. The primers used were: ZNRF3 5'-GATGGAGAGGAGCTGAGAGTCATTC-3' (forward) (SEQ ID NO: 17); 5'-GATAACTCGCTGT-TGCTGCTG-3' (reverse) (SEQ ID NO: 18); H4 histone 5'-CGGGATAACATTCAGGGTA-3' (forward) (SEQ ID NO: 19); 5'-TCCATGGCGGTAACTGTC-3' (reverse) (SEQ ID NO: 20). Samples were normalized against H4 histone as an internal control. For RT-PCR with *Xenopus* animal caps, mRNA was injected into the animal poles of both blastomeres at 2-cell stage. The animal caps were isolated at stage 8.5 and cultured until stage 10.5 for RT-PCR. The primers used were: Siamois, 5'-CTCCAGCCACCAGTACCAGATC-3' (forward) (SEQ ID NO: 21); 5'-GGGGAGAGTGGAAAGTG-GTTG-3' (reverse) (SEQ ID NO: 22); Xnr3, 5'-TCCACT-TGTGCAGTTCCACAG-3' (forward) (SEQ ID NO: 23); 5-ATCTCTTCATGGTGCCTCAGG-3' (reverse) (SEQ ID NO: 24); and Elf1alpha, 5-CAGATTGGTGCTGGATATGC-3' (forward) (SEQ ID NO: 25), 5'-ACTGCCTTGATGACTC-CTAG-3' (reverse) (SEQ ID NO: 26).

Taking our results from the zebrafish and *Xenopus* assays together, we found that induction of typical phenotypes associated with excessive β-catenin signaling by ZNRF3 AIRING indicates that ZNRF3 suppresses Wnt/β-catenin signaling in vivo. Precise regulation of PCP signaling output is required for normal gastrulation, and either increased or decreased PCP signaling disrupts convergent extension movements. Interestingly, overexpression of wild-type ZNRF3 or ZNRF3 AIRING in zebrafish embryos produced phenotypes characteristic of convergent extension defects, such as shortened body axes and broader somites as judged by staining with riboprobes against myoD and pcdh8. Overexpression of wild type ZNRF3 frequently caused axis bifurcation, and interestingly, the same phenotype was also produced by overexpression of a dominant negative Frizzled. Nasevicius A. et al. "Evidence for a frizzled-mediated wnt pathway required for zebrafish dorsal mesoderm formation." *Development* 125, 4283-4292 (1998).

All observed phenotypes are consistent with the convergent extension defects and indicate that perturbing the activity of ZNRF3 affects gastrulation movements. This is confirmed in a fluorescent lineage tracing experiment. In control embryos, cells converge upon the dorsal midline. In contrast, cells overexpressing either wild-type ZNRF3 or ZNRF3 AIR-ING showed defective dorsolateral movements as they did not converge normally towards the midline.

Third, to study the function of ZNRF3 in mice, the inventors constructed Znrf3 knockout mice and back-crossed the knockout mutation to a C57BL/6 background. Znrf3 deficient embryos died around birth.

In the targeting vector, exon 7 encoding the RING domain is flanked by two loxP sites. Linearized targeting vector was electroporated into 129/SvJ ES cells, and G418 resistant ES clones were first screened by nested PCR, and then subjected to Southern blot analysis. Genomic DNAs were digested with XmnI or BglII restriction enzymes, and hybridized with probes positioned outside the 5' and 3' homologous regions, respectively. ES clone 5A7 was used for blastocyst injection and chimeric males were mated with CRE deleter mice in the C57BL/6J background. F1 mice with cre-mediated deletion of exon 7 were identified by PCR, and further backcrossed in the C57BL/6J background before intercrosses of heterozygous mice to produce homozygous mice/embryos. Wild type, heterozygous and homozygous mice were identified by 'multiplex' PCR with following primers: NEO (T, forward), 5'-TATCATGGTCTGTATACCGGGATCG-3' (SEQ ID NO: 27); #523 (E, forward): 5'-CATACTTTGGGCTCATGAG-CAAGC-3' (SEQ ID NO: 28); #521 (E, T, reverse): 5'-GCAG-GTATACATTACCACACCC-3' (SEQ ID NO: 29). Znrf3 deficient mice were crossed into C57BL/6J background. Znrf3$^{-/-}$ mouse embryos and wild-type littermate controls were generated by timed mating of heterozygous parents. At indicated embryonic stage, pregnant females were sacrificed and embryos were dissected out for imaging or histology after fixation in 4% paraformaldehyde for overnight at 4° C. The genotypes of embryos were determined by PCR genotyping using genomic DNA extracted from yolk sac. After dehydration in gradient serials of ethanol, the embryo was paraffin embedded on head for horizontal sectioning, and slides were stained by hematoxylin and eosin. Whole mount in situ hybridization with E9.5 mouse embryos was carried out according to standard protocols using 25 nM double DIG labeled locked nucleic acid (LNA) probe from Exiqon was used. Mouse Axin2 probe sequence: TCTCTAACATC-CACTGCCAGA (SEQ ID NO: 30).

The most noticeable phenotype of Znrf3 null embryos is the lack of lens formation. This phenotype is likely due to hyperactive β-catenin signaling during lens development as the expression of β-catenin target gene Axin2 was significantly increased in the eye region of E9.5 Znrf3 null embryos.

It is known that suppression of Wnt/β-catenin signaling in the surface ectoderm is important for lens development. Ectopic activation of β-catenin signaling in eyes blocks lens formation while eye-specific deletion of β-catenin leads to formation of ectopic lentoid bodies. Smith A N, Miller L A, Song N, Taketo M M, and Lang R A, "The duality of beta-catenin function: a requirement in lens morphogenesis and signaling suppression of lens fate in periocular ectoderm." *Dev. Biol.* 285, 477-489 (2005); Kreslova J et al. "Abnormal lens morphogenesis and ectopic lens formation in the absence of beta-catenin function." *Genesis.* 45, 157-168 (2007); Machon O et al. "Lens morphogenesis is dependent on Pax6-mediated inhibition of the canonical Wnt/beta-catenin signaling in the lens surface ectoderm." *Genesis.* 48, 86-95 (2010).

It is known that Wnt/PCP signaling is important for cell movements during narrowing of the folding neural plate and that Frizzled- and Dishevelled-deficient mice show neural tube closure defects. Wang Y, Guo N, and Nathans J, The role of Frizzled3 and Frizzled6 in neural tube closure and in the planar polarity of inner-ear sensory hair cells. *J. Neurosci.* 26, 2147-2156 (2006); Yu H et al. "Frizzled 1 and frizzled 2 genes function in palate, ventricular septum and neural tube closure: general implications for tissue fusion processes." *Development* 137, 3707-3717 (2010); Wang J et al. "Dishevelled genes mediate a conserved mammalian PCP pathway to regulate convergent extension during neurulation." *Development* 133, 1767-1778 (2006); Etheridge S L et al. "Murine dishevelled 3 functions in redundant pathways with dishevelled 1 and 2 in normal cardiac outflow tract, cochlea, and neural tube development." *PLoS Genet.* 4, e1000259 (2008). Interestingly, about 20% of our Znrf3 null embryos show neural tube closure defects, which likely result from disrupted Wnt/PCP signaling. Taken together, these results indicate that ZNRF3 regulates both Wnt/β-catenin and Wnt/PCP signaling in vivo.

R-spondin enhances Wnt signaling through inhibiting ZNRF3. As described further below, R-spondin proteins (e.g., RSPO1-RSPO4) are a family of secreted molecules that strongly potentiate Wnt/β-catenin signaling and Wnt/PCP, thus having biological and therapeutic significance. The inventors have discovered that ZNRF3 is the molecular target of R-spondin. Our results show that ZNRF3 inhibits Wnt signaling by promoting the turnover of Frizzled and LRP6, and that this ZNRF3 activity is inhibited by R-spondin.

R-spondin potentiates Wnt/β-catenin and Wnt/PCP signaling. Since Frizzled is shared by Wnt/β-catenin and Wnt/PCP pathways and R-spondin induces Dvl phosphorylation, we tested whether R-spondin potentiates Wnt signaling through increasing the membrane level of Frizzled. Indeed, we found that R-spondin 1 (RSPO1) increases the membrane level of Myc-FZD8, by using a cell surface protein biotinylation assay and in a flow cytometry assay. We found that RSPO1 also increases the cell surface level of endogenous Frizzleds in a flow cytometry assay using a pan-Frizzled antibody.

Since ZNRF3 regulates the membrane level of Frizzled proteins, we tested whether R-spondin enhances Wnt signaling through inhibiting ZNRF3. We found that R-spondin physically interacts with the extracellular domain of R-spondin. To do so, the inventors transiently transfected HEK293 cells with N-terminal Myc-tagged FZD4 (Frizzled 4), or ZNRF3 ECD-TM, or ZNRF3 P103A ECD-TM, then incubated these cells with RSPO1-GFP conditioned medium for 1 hour. We determined the binding of RSPO1-GFP to Myc tagged proteins expressed on the cell surface using immunofluorescence using anti-GFP and anti-Myc antibodies. Using this cell-based binding assay, RSPO1-GFP was shown to bind to ZNRF3 ECD-TM, but not ZNRF3 P103A ECD-TM or FZD4. Thus, our result shows that R-spondin specifically interacts with the extracellular domain of ZNRF3.

Figure 9:
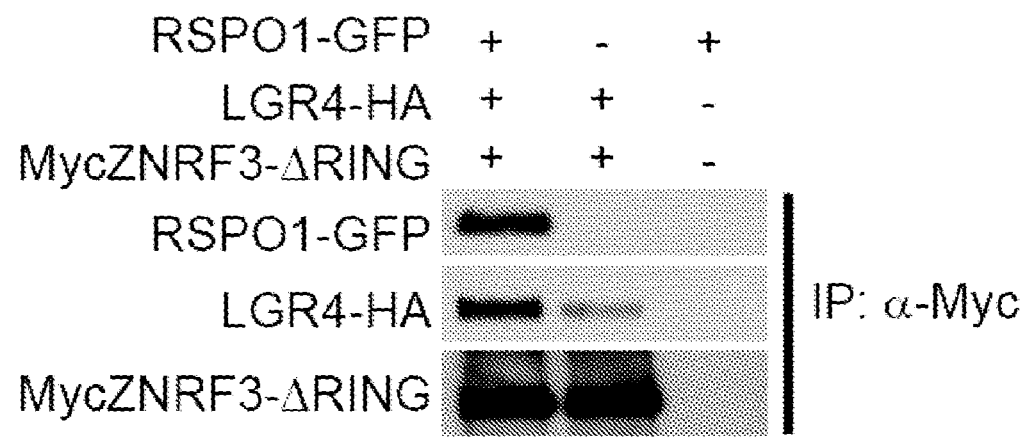
FIG. 9 is a set of polyacrylamide gel slices showing coimmunoprecipitation of R-spondin (RSPO), LGR4 and ZNRF3. HEK293 cells coexpressing LGR4-HA and Myc-ZNRF3 ΔRING were treated with RSPO1-GFP conditioned medium (CM) for 1 hour, and cell lysates were immunoprecipitated with anti-Myc antibody, and immunoprecipitates were resolved and blotted with anti-HA, anti-Myc, and anti-GFP antibodies. This figure shows that RSPO1 increases the interaction between ZNRF3 and LGR4.

Since R-spondin is also known to bind to LGR4, the inventors tested whether R-spondin interacts with LGR4 and ZNRF3 simultaneously to induce the interaction between ZNRF3 and R-spondin. This is shown in FIG. 9. HEK293 cells were coexpressing LGR4-HA and Myc-ZNRF3 ΔRING were treated with RSPO1-GFP conditioned medium (CM) for 1 hour. Cell lysates were then immunoprecipitated with anti-Myc antibody. The immunoprecipitates were resolved and blotted with anti-HA, anti-Myc, and anti-GFP antibodies. FIG. 9 shows that RSPO1 increases the interaction between ZNRF3 and LGR4.

Figure 10:
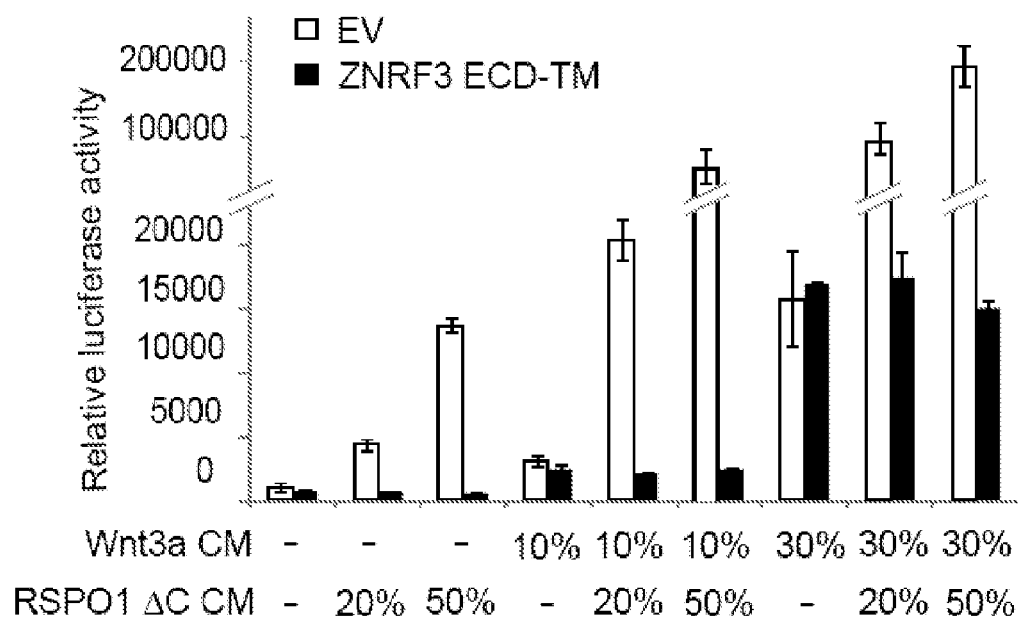
FIG. 10 is a set of bar graphs showing overexpressing ZNRF3 ECD-TM (a ZNRF3 mutant with the majority of the intracellular domain truncated) specifically inhibits RSPO1 but not Wnt3a induced STF activity. HEK293-STF cells stably expressing empty vector (EV) or ZNRF3 ECD-TM were treated with Wnt3a or RSPO1 ΔC overnight, and subjected to STF luciferase reporter assay.

Since R-spondin increases Wnt signaling through binding to ZNRF3 and suppressing its activity, we tested whether overexpression of ZNRF3 ECD prevents the interaction between R-spondin and endogenous ZNRF3, and inhibit R-spondin-mediated signaling. This is shown in FIG. 10. HEK293 cells stably expressing STF luciferase reporter together with empty vector or ZNRF3 ECD-TM were treated with Wnt3a conditioned medium or RSPO1 ΔC conditioned medium at indicated concentrations and combinations overnight. The cells were then subjected to the luciferase reporter assay. As shown in FIG. 10, overexpression of ZNRF3 ECD-TM blocked RSPO1 but not Wnt3a-induced STF activation.

Accordingly, our results show that overexpression of ZNRF3 ECD-TM inhibited R-spondin but not Wnt3a induced β-catenin stabilization in HEK293 cells. Overexpression of ZNRF3 ECD-TM also blocked RSPO1 induced membrane accumulation of endogenous Frizzleds in flow cytometry assay using a pan-Frizzled antibody. Together, our results from FIG. 9 and FIG. 10 show that R-spondin enhances Wnt signaling through inhibiting ZNRF3 and increasing the cell surface level of Frizzled proteins. R-spondin physically interacts with the extracellular domain of ZNRF3 and induces the association between ZNRF3 and LGR4.

As discussed further below, our results indicate that a bispecific antibody that binds to both ZNRF3 (or RNF43) and LGR4 (or LGR5 or LGR6) would mimic R-spondin activity and enhance Wnt signaling.

Administration of the antibodies of the invention to treat diseases resulting from insufficient Wnt signaling and pharmaceutical formulations for the administration of the antibodies of the invention. The antibodies of the invention are useful for the treatment of diseases characterized by low Wnt signaling.

Pathologically low levels of Wnt signaling have been associated with osteoporosis, polycystic kidney disease and neurodegenerative diseases. Controlled activation of Wnt pathway has been shown to promote regenerative processes such as tissue repair and wound-healing. Zhao J, Kim K A, and Abo A, "Tipping the balance: modulating the Wnt pathway for tissue repair." *Trends Biotechnol.* 27(3):131-6 (March 2009). See also, Logan C Y and Nusse R, "The Wnt signaling pathway in development and disease." *Annu. Rev. Cell. Dev. Biol.* 20:781-810 (2004); Nusse R., "Wnt signaling in disease and in development." *Cell Res.* 15(1):28-32 (January 2005); Clevers H, "Wnt/beta-catenin signaling in development and disease." *Cell* 127(3):469-80 (3 Nov. 2006). Proof-of-concept experiments have been done to show the role of Wnt signaling in osteoporosis or mucositis. Furthermore, it has been suggested that increasing of Wnt signaling might be beneficial for the treatment of diabetes and other metabolic diseases.

Antibodies that bind to the extracellular domain of ZNRF3 and RNF43 to inhibit the function of ZNRF3 and RNF43 will sensitize cells to Wnt signaling, and thus can be used for diseases or other indications that will benefit from Wnt stimulators. Some of the diseases and conditions associated with low Wnt signaling include, but are not limited to, mucositis short bowel syndrome, bacterial translocation in the gastrointestinal mucosa, enterotoxigenic or enteropathic infectious diarrhea, celiac disease, non-tropical sprue, lactose intolerance and other conditions where dietary exposures cause blunting of the mucosal villi and malabsorption, atrophic gastritis and diabetes. Also included are osteoporosis, bone fracture, metabolic diseases such as diabetes, neurodegenerative disease and melanoma. In addition, the antagonizing antibodies of the invention can be used to enhance Wnt signaling for tissue regeneration, such as tissue repair and wound healing. Examples of damaged tissue that can be treated using methods of the invention include, but are limited to, intestinal tissue, cardiac tissue, liver tissue, kidney tissue, skeletal muscle, brain tissue, bone tissue, connective tissue, and skin tissue.

U.S. Patent Application 2009/0220488 describes the administration of antibodies (not the antibodies of the invention) to therapeutically modulate activity of a Wnt signaling pathway, especially antibodies that bind to a secreted component of a Wnt signaling pathway or to an extracellular region of a component of a Wnt signaling pathway. U.S. Patent Application 2009/0220488 describes, for example, antibodies that bind to Wnt and inhibit Wnt activity, e.g., inhibit Wnt binding to a cell surface receptor, e.g., a Frizzled receptor or LRP5/6. Another class of antibodies cited by the patent application includes antibodies that bind to the extracellular region of a cell surface receptor for Wnt, such as a Frizzled receptor or LPR5/6, to reduce or prevent Wnt interaction with the receptor or otherwise reduce receptor signaling. The methods for administration of described by the patent application can be adapted for antibodies that bind to the extracellular domain of ZNRF3 or RNF43. Thus, the antibody of the invention can be used to administer to a subject with a disease or condition characterized by a low Wnt signaling. By this administration, the antibodies of the invention are used to "treat" the subject. As the Wnt signaling in the subject is increased, the administration of the antibody of the invention will "ameliorate" the disease or condition in the subject.

Mucositis is a clinical complication of cancer therapy. Mucositis is caused by the cytotoxic effects of irradiation or chemotherapy on fast proliferating cells. Mucositis consists of epithelial damage mainly affecting the intestinal and oral mucosa. Clinical signs are severe pain of the oral cavity, nausea, diarrhea, malnutrition, and, in severe cases, sepsis and death. The symptoms can often lead to dose limitation of cancer therapy. There are no currently available treatments for oral or gastrointestinal-mucositis associated with chemotherapy or radiation therapy for solid tumors.

Oral mucositis is a common and often debilitating complication of cancer treatment. 50% of patients undergoing radiotherapy for head and neck cancer and 10-15% of patients treated with 5-FU get grade 3-4 oral mucositis. RSPO1 has been shown to ameliorate oral mucositis in an animal model. Zhao J et al., *PNAS* 106:2331 (2010).

Short bowel syndrome (SBS) results from functional or anatomic loss of extensive segments of small intestine, so that digestive and absorptive capacities are severely compromised. Each year, many people undergo resection of long segments of small intestine for various disorders, including trauma, inflammatory bowel disease, malignancy, mesenteric ischemia and others. Various nonoperative procedures such as radiation can cause functional short-bowel syndrome. Current therapies for short-bowel syndrome include dietary approaches, total parenteral nutrition (TPN), intestinal transplantation, and nontransplantation abdominal operations. Although these treatments have contributed to the improved outcome of SBS patients, they only partially correct the underlying problem of reduced bowel function. No current therapy can accelerate the recovery of remaining small intestine in SBS patients. See, Seetharam and Rodrigues, "Short bowel syndrome: a review of management of options" *The Saudi Journal of Gastroenterology* 17, 229-235 (2011).

The adult mammalian gut constitutes one of the most rapidly self-renewing tissues, in which the intestinal mucosa comprises a continuous structure folded into the proliferative crypts and the differentiated villi. In response to mucosal disruption, the host initiates a healing response resulting in restoration of mucosal integrity and regeneration of the mucosal architecture. This process is heavily dependent on the proliferation of intestinal stem cells. Neal et al., "Intestinal stem cells and their roles during mucosal injury and repair." *Journal of Surgical Research* 167, 1-8 (2010); van der Flier and Clevers, "Stem cells, self-renewal, and differentiation in the intestinal epithelium." *Annual Review of Physiology* 71, 241-261 (2009).

Therefore, the factors that regulate the activity of intestinal stem cells play a dominant role in the ability of the host to respond to injury within the intestinal tract. Because Wnt proteins are the most important growth factors that support the proliferation of intestinal stem cells, enhancing Wnt signaling will increase the proliferation of intestinal epithelium. This will lead to increased number of small bowel villi and increased mucosal absorptive surface area.

Thus, in one embodiment, the antibody of the invention is administered to a person with short bowel syndrome. The antibody is administered with the purpose of increasing gastrointestinal mucosal absorptive surface area. The administration of the antibody of the invention has a successful outcome when the person with incident short bowel syndrome adapts to enteral feeding, or when the person with prevalent SBS absorbs nutrients from enteral feeds, or when the person decreases the amount of total parenteral nutrition required daily for the person to maintain weight.

Prevention of bacterial translocation. In one embodiment, the antibody of the invention is administered to a person at risk of septicemia caused by enteric bacteria. The antibody is administered with the purpose of increasing gastrointestinal mucosal integrity, thus preventing enteric bacteria from passing into the bloodstream of the person. Decreased gastrointestinal mucosal integrity (as compared with the gastrointestinal mucosal integrity that is normal for the human population) is a major source of bloodstream infections and sepsis in critically ill patients. The administration of the antibody has a successful outcome when fewer cases of bacteremia and sepsis are observed in intensive care unit (ICU) patients than in patients to whom the antibody of the invention is not administered.

Accelerated recovery during or after enterotoxigenic or enteropathic infectious diarrhea. Infectious diarrhea is a major pediatric problem. In one embodiment, the antibody of the invention is administered with the purpose of shortening the time to the end of diarrhea or the time to normal bowel movements. The antibody of the invention can be administered in addition to the standard of care, which includes oral or parenteral rehydration and sometimes, antibiotics. The administration of the antibody has a successful outcome when decrease hospitalizations, shorten hospitalizations, or a decrease the incidence of complications of dehydration and electrolyte abnormalities are observed in pediatric patients as compared with pediatric patients to whom the antibody of the invention is not administered.

Celiac disease, non-tropical sprue, lactose intolerance and other conditions where dietary exposures cause blunting of the mucosal villi and malabsorption. In one embodiment, the antibody of the invention is administered with the purpose of increasing mucosal absorptive surface area. The antibody of the invention can be administered in addition to the standard of care, which is primarily avoiding the offending foods and sometimes, dietary supplements. The administration of the antibody of the invention has a successful outcome when the person with celiac disease, non-tropical sprue, lactose intolerance or other condition adapts to enteral feeding, or when the person with any of the conditions absorbs nutrients from enteral feeds, or when the person decreases the amount of total parenteral nutrition required daily for the person to maintain weight.

Atrophic gastritis, specifically the Form termed environmental metaplastic atrophic gastritis. Atrophic gastritis is a common condition in the elderly, currently treated with vitamin B12 injections. The patients have an increased risk of carcinoid tumors and adenocarcinoma. The administration of the antibody has a successful outcome when decreased the tumor incidence, in the case of carcinoid by decreasing gastrin production from the metaplastic G cells, is observed by a medical expert. The antibody should not be administered to the subject if a medical expert determined that if the tumors are activated by increases in the Wnt pathway.

Type 2 diabetes mellitus. In one embodiment, the antibody of the invention is administered with the purpose of increasing levels of incretin hormones, for example glucagon-like peptide-1 (GLP-1) and gastric inhibitory peptide (GIP). Incretins cause an increase in the amount of insulin released from the beta cells of the islets of Langerhans after eating. Both incretins GLP-1 and GIP are rapidly inactivated by the enzyme dipeptidyl peptidase-4 (DPP-4). DPP-4 inhibitors increase active incretin levels by preventing the inactivation of endogenous incretins by DPP-4.

The efficacy of DPP-4 inhibitors is dependent upon endogenous active incretin levels that appear to be diminished in patients with type II diabetes mellitus. See, Pratley R E and Gilbert M, Rev. Diabet. Stud. 5(2):73-94 (2008).

The administration of the antibody of the invention increases the number of enteroendocrine cells (e.g., L cells and K cells) by inhibiting the Wnt pathway, which causes a proliferation of cells in the intestines that are able to produce incretins. Since DPP-4 inhibitors require endogenous production of incretins for efficacy, the antibody of the invention can be administered as a combination therapy with a DPP-4 inhibitor, such as vildagliptin (Galvus®), sitagliptin (Januvia®), saxagliptin (Onglyza®), linagliptin (Trajenta®), dutogliptin, gemigliptin, alogliptin or another DPP-4 inhibitor, or with a compound with DPP-4 inhibitor, such as berberine, for use by people with type II diabetes.

The combination therapy may be the administration of the antibody of the invention to the subject before the administration of a DPP-4 inhibitor. The amount of time before the administration of the DPP-4 inhibitor will be such that the subject's enteroendocrine cells will proliferate enough to produce incretins. The production of incretins can be tested by laboratory methods.

The combination therapy may instead be the administration of the antibody of the invention to the subject concurrent with the administration of a DPP-4 inhibitor, such that the proliferation of the enteroendocrine cells and the inhibition of DPP-4 occur concurrently. The term "concurrent with" means that the antibody of the invention is administered to the subject with type II diabetes while the subject is undergoing DPP-4 inhibitor therapy. The administration of the antibody of the invention may or may not be at the same time as the administration of the DPP-4 inhibitor or in a combination with the DPP-4 inhibitor. Because incretins such as GLP-1 also cause the proliferation of L cells (see, Grigoryan M et al., Endocrinology 153: 3076-3088 (2012), the administration of the antibody of the invention with a DPP-4 inhibitor can enhance a positive feedback loop, since the increased incretin levels (from DPP-4 inhibition) upregulates intestinal epithelial L cells and the the upregulated L cells (from ZNRF3 antagonism) upregulate incretin levels.

The administration of the antibody of the invention, either before the administration of a DPP-4 inhibitor or in combination with a DPP-4 inhibitor, has a successful outcome when the subject has a better control of the type II diabetes mellitus, as assessed by HgbA1c change from baseline. For a method of assessing HgbA1c change from baseline, see, e.g., Vilsbøll T et al., J Clin Endocrinol Metab 88:4897-4903 (2003).

Metabolic disease. Decreased Wnt signaling has been associated with metabolic disease. Loss-of-function LRP6$^{R611C}$ mutation results in early coronary artery disease, metabolic syndrome and osteoporosis in human. Main A et al., Science 315:1278 (2007). "LRP5 loss-of-function mutation is associated with osteoporosis, impaired glucose metabolism and hypercholesterolaemia in human." Saarinnen et al., Clin Endocrinol 72:481 (2010). Severe hypercholesterolemia, impaired fat tolerance, and advanced atherosclerosis in mice lacking both LRP5 and apoE. Magoori K et al., JBC 11331 (2003). LRP5 is essential for normal cholesterol metabolism and glucose-induced insulin secretion in mice. Fujino et al., PNAS 100:229 (2003). TCF7L2 variant confers risk of type 2 diabetes. Grant S F et al., Nat Genet 38:320 (2006); Florez J C et al., N Engl J Med 355:241 (2006). In summary, it is known that an increase of Wnt signaling can be beneficial for treating metabolic diseases. Accordingly, the administration of the antibody of the invention to a subject with metabolic disease is useful for treating the subject's metabolic disease.

Inflammatory bowel disease (IBD) is a group of inflammatory conditions of the colon and small intestine. The major types of IBD are Crohn's disease and ulcerative colitis. RSPO1 protein has been shown to ameliorate inflammatory bowel disease in an animal model. Zhao J et al., Gastroenterology 132:1331 (2007). Accordingly, the administration of the antibody of the invention to a subject with IBD is useful for treating the subject's IBD.

Formulations. The invention provides pharmaceutical compositions comprising the antibodies or antigen binding fragments of the invention formulated together with a pharmaceutically acceptable carrier. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific antibodies or fragments thereof, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy (Mack Publishing Co., 20th ed., 2000); and Sustained and Controlled Release Drug Delivery Systems, J. R. Robinson, ed., (Marcel Dekker, Inc., New York, 1978). Pharmaceutical compositions are preferably manufactured under GMP conditions. Typically, a therapeutically effective dose or efficacious dose of the antibody of the invention is employed in the pharmaceutical compositions of the invention. The antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Dosages. Actual dosage levels of the active ingredients in the pharmaceutical compositions of the invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular compositions of the invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the invention, for the treatment of an allergic inflammatory disorder described herein vary depending upon many different factors, including means of administration, target site, physiological state of the subject, whether the subject is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

Antibody is usually administered on multiple occasions. Intervals between single dosages can be weekly, monthly or yearly. Intervals can also be irregular as indicated by measuring blood levels of the antibody of the invention in the subject. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the subject. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

Bispecific antibodies. ZNRF3 is a molecular target of R-spondin. R-spondin interacts with both ZNRF3 and LGR4 and inhibits the function of ZNRF3. Induced dimerization of ZNRF3 and LGR4 is expected to mimic R-spondin and inhibit the function of ZNRF3. Accordingly, the invention provides bispecific or multispecific antibodies or antigen-binding fragments thereof. One part of the antibody binds to the extracellular domain of ZNRF3 or RNF43. The other part of the antibody binds to R-spondin coreceptor LGR4, LGR5, or LGR6. Such antibodies should mimic R-spondin and enhance Wnt signaling.

An antibody of the invention, or antigen-binding regions thereof, can be derivatized or linked to another functional molecule, e.g., another peptide or protein (e.g., another antibody or ligand for a receptor) to generate bispecific antibodies and fragments thereof that bind to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Additionally, for the invention in which the bispecific antibodies and fragments thereof are multispecific, the antibodies and fragments thereof can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as an Fv or a single chain construct as described in U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites. See e.g., Holliger et al., *Proc. Natl. Acad. Sci. USA* 90:6444-6448 (1993); Poljak et al., *Structure* 2:1121-1123 (1994). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues. See, Holliger and Winter, *Cancer Immunol. Immunother.* 45(3-4):

128-30 (1997); Wu et al., *Immunotechnology* 2(1):21-36 (1996). scDb can be expressed in bacteria in soluble, active monomeric form. See, Holliger and Winter, *Cancer Immunol. Immunother.*, 45(34): 128-30 (1997); Wu et al., *Immunotechnology* 2(1):21-36 (1996); Pluckthun and Pack, *Immunotechnology* 3(2): 83-105 (1997); Ridgway et al., *Protein Eng.* 9(7):617-21 (1996). A diabody can be fused to Fc to generate a "di-diabody". See, Lu et al., *J. Biol. Chem.* 279(4):2856-65 (2004).

Other antibodies which can be employed in the bispecific molecules of the invention are murine, chimeric and humanized monoclonal antibodies.

The bispecific antibodies of the invention can be prepared by conjugating the constituent binding specificities, using methods known in the art. For example, each binding specificity of the bispecific antibody can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohexane-1-carboxylate (sulfo-SMCC). See, e.g., Karpovsky et al., *J. Exp. Med.* 160:1686 (1984); Liu, M A et al., *Proc. Natl. Acad. Sci. USA* 82:8648 (1985)). Other methods include those described in Paulus, *Behring Ins. Mitt.* No. 78, 118-132 (1985); Brennan et al., *Science* 229:81-83 (1985), and Glennie et al., *J. Immunol.* 139: 2367-2375 (1987). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the invention provides multivalent compounds comprising at least two identical or different antigen-binding portions of the antibodies of the invention. The antigen-binding portions can be linked together via protein fusion or covalent or non-covalent linkage. Alternatively, methods of linkage have been described for the bispecific antibodies and fragments thereof. Tetravalent antibodies and fragments thereof can be obtained for example by cross-linking antibodies of the antibodies of the invention with an antibody that binds to the constant regions of the antibodies of the invention, for example the Fc or hinge region.

Thus, bispecific antibodies (or other similar agents such as protein chimeras) binding to both LGR4/LGR5/LGR6 and ZNRF3/RNF43 will sensitize cells to Wnt signaling and can be used for diseases or other indications that will benefit from Wnt stimulators. Such indications include, but are not limited to, mucositis short bowel syndrome, bacterial translocation in the gastrointestinal mucosa, enterotoxigenic or enteropathic infectious diarrhea, celiac disease, non-tropical sprue, lactose intolerance and other conditions where dietary exposures cause blunting of the mucosal villi and malabsorption, atrophic gastritis and type II diabetes mellitus. Also included are osteoporosis, bone fracture, metabolic diseases such as diabetes, neurodegenerative disease and melanoma.

For example, in certain embodiments the disclosure relates:
(i) to antibodies where one part of the antibody binds to the extracellular domain of ZNRF3 and the other part of the antibody binds to the extracellular domain of a coreceptor of R-spondin, or
(ii) to antibodies where one part of the antibody binds to the extracellular domain of RNF43 and the other part of the antibody binds to the extracellular domain of a coreceptor of R-spondin.

R-Spondin. R-spondin proteins (RSPO1-4) are a family of secreted molecules that strongly potentiate Wnt/β-catenin signaling and Wnt/PCP signaling. Kazanskaya O et al. "R-spondin2 is a secreted activator of Wnt/beta-catenin signaling and is required for *Xenopus* myogenesis". *Dev. Cell* 7, 525-534 (2004); Kim K A et al., "Mitogenic influence of human R-spondin1 on the intestinal epithelium." *Science* 309, 1256-1259 (2005); Kim K A, "R-Spondin family members regulate the Wnt pathway by a common mechanism." *Mol. Biol. Cell* 19, 2588-2596 (2008); Ohkawara B, Glinka A, and Niehrs C, "Rspo3 binds syndecan 4 and induces Wnt/PCP signaling via clathrin-mediated endocytosis to promote morphogenesis." *Dev. Cell* 20, 303-314 (2011); Kamata T et al., "R-spondin, a novel gene with thrombospondin type 1 domain, was expressed in the dorsal neural tube and affected in Wnts mutants." *Biochim. Biophys. Acta* 1676, 51-62 (2004); Nam J S., Turcotte T J, and Yoon J K, "Dynamic expression of R-spondin family genes in mouse development." *Gene Expr. Patterns.* 7, 306-312 (2007); Aoki M et al., "R-spondin3 is required for mouse placental development." *Dev. Biol.* 301, 218-226 (2007); Blaydon D C et al., "The gene encoding R-spondin 4 (RSPO4), a secreted protein implicated in Wnt signaling, is mutated in inherited anonychia." *Nat. Genet.* 38, 1245-1247 (2006); Kazanskaya O. et al. "The Wnt signaling regulator R-spondin 3 promotes angioblast and vascular development." *Development* 135, 3655-3664 (2008); Parma P et al., "R-spondin1 is essential in sex determination, skin differentiation and malignancy." *Nat. Genet.* 38, 1304-1309 (2006). R-spondins are coexpressed or induced by Wnt and are involved in tissue patterning and differentiation.

Rspo1 is expressed in paneth cells of intestinal crypts, which form the niche of Lgr5+ stem cells. RSPO1 stimulates the proliferation of crypt stem cells and protects mice from chemotherapy-induced mucositis. Zhao J et al. "R-Spondin1 protects mice from chemotherapy or radiation-induced oral mucositis through the canonical Wnt/beta-catenin pathway." *Proc. Natl. Acad. Sci. U.S.A* 106, 2331-2336 (2009).

Accordingly, the invention provides antibodies binding to the extracellular domain of ZNRF3 and RNF43 that block the interaction between R-spondin and ZNRF3 or RNF43. Such antibodies can be formulated in a pharmaceutically acceptable carrier. Such antibodies will block R-spondin-stimulated Wnt signaling and can be used for indications that will benefit from Wnt inhibitors. Such indications include, but are not limited to, various cancers, sclerosteosis, idiopathic pulmonary fibrosis, cardiac hypertrophy.

Moreover, the invention provides the extracellular domain of ZNRF3 and RNF43. These extracellular domains can be administered for therapeutic effect, because these proteins will bind to R-spondin circulating in tissues to inhibit R-spondin signaling. The administered extracellular domain of ZNRF3 or RNF43 acts as a pseudo-receptor. Such administered proteins can be formulated in a pharmaceutically acceptable carrier. Such administered proteins will block R-spondin-stimulated Wnt signaling and can be used for indications that will benefit from Wnt inhibitors. Such indications include, but are not limited to, various cancers, sclerosteosis, idiopathic pulmonary fibrosis, cardiac hypertrophy.

The contents of each of the patents and publications cited herein are incorporated by reference in their entirety.

The detailed description provided herein is to illustrate the invention but not to limit its scope. Other variants of the invention will be readily apparent to one of ordinary skill in the art and are encompassed by the appended claims.

We claim:

1. An isolated antibody or antigen binding fragment thereof comprising one or more polypeptides that specifically binds to the extracellular domain of the transmembrane E3 ubiquitin ligase ZNRF3, wherein said one or more polypeptides are selected from the group consisting of:

(a) one or more polypeptides having six regions, comprising:
(i) three regions from the amino terminus of the antibody or antigen binding fragment to the carboxyl terminus: a first region of having a peptide sequence of SEQ ID NO: 31; a second region having a peptide sequence of SEQ ID NO: 32; and a third region having a peptide sequence selected from the group consisting of SEQ ID NO: 33; and
(ii) three regions from the amino terminus of the antibody or antigen binding fragment to the carboxyl terminus: a first region of having a peptide sequence of SEQ ID NO: 34; a second region having a peptide sequence of SEQ ID NO: 35; and a third region having a peptide sequence selected from the group consisting of SEQ ID NO: 36; and (b) one or more polypeptides having six regions, comprising:
(i) three regions from the amino terminus of the antibody or antigen binding fragment to the carboxyl terminus:

a first region of having a peptide sequence of SEQ ID NO: 37; a second region having a peptide sequence of SEQ ID NO: 38; and a third region having a peptide sequence selected from the group consisting of SEQ ID NO: 39; and
(ii) three regions from the amino terminus of the antibody or antigen binding fragment to the carboxyl terminus: a first region of having a peptide sequence of SEQ ID NO: 40; a second region having a peptide sequence of SEQ ID NO: 41; and a third region having a peptide sequence selected from the group consisting of SEQ ID NO: 42; and (c) one or more polypeptides having six regions, comprising:
(i) three regions from the amino terminus of the antibody or antigen binding fragment to the carboxyl terminus: a first region of having a peptide sequence of SEQ ID NO: 43; a second region having a peptide sequence of SEQ ID NO: 44; and a third region having a peptide sequence selected from the group consisting of SEQ ID NO: 45; and
(ii) three regions from the amino terminus of the antibody or antigen binding fragment to the carboxyl terminus: a first region of having a peptide sequence of SEQ ID NO: 46; a second region having a peptide sequence of SEQ ID NO: 47; and a third region having a peptide sequence selected from the group consisting of SEQ ID NO: 48; and (d) one or more polypeptides having six regions, comprising:
(i) three regions from the amino terminus of the antibody or antigen binding fragment to the carboxyl terminus: a first region of having a peptide sequence of SEQ ID NO: 49; a second region having a peptide sequence of SEQ ID NO: 50; and a third region having a peptide sequence selected from the group consisting of SEQ ID NO: 51; and
(ii) three regions from the amino terminus of the antibody or antigen binding fragment to the carboxyl terminus: a first region of having a peptide sequence of SEQ ID NO: 52; a second region having a peptide sequence of SEQ ID NO: 53; and a third region having a peptide sequence selected from the group consisting of SEQ ID NO: 54; and (e) one or more polypeptides having six regions, comprising:
(i) three regions from the amino terminus of the antibody or antigen binding fragment to the carboxyl terminus: a first region of having a peptide sequence of SEQ ID NO: 55; a second region having a peptide sequence of SEQ ID NO: 56; and a third region having a peptide sequence selected from the group consisting of SEQ ID NO: 57; and
(ii) three regions from the amino terminus of the antibody or antigen binding fragment to the carboxyl terminus: a first region of having a peptide sequence of SEQ ID NO: 58; a second region having a peptide sequence of SEQ ID NO: 59; and a third region having a peptide sequence selected from the group consisting of SEQ ID NO: 60; and (f) one or more polypeptides having six regions, comprising:
(i) three regions from the amino terminus of the antibody or antigen binding fragment to the carboxyl terminus: a first region of having a peptide sequence of SEQ ID NO: 61; a second region having a peptide sequence of SEQ ID NO: 62; and a third region having a peptide sequence selected from the group consisting of SEQ ID NO: 63; and
(ii) three regions from the amino terminus of the antibody or antigen binding fragment to the carboxyl terminus: a first region of having a peptide sequence of SEQ ID NO: 64; a second region having a peptide sequence of SEQ ID NO: 65; and a third region having a peptide sequence selected from the group consisting of SEQ ID NO: 66; and (g) one or more polypeptides having six regions, comprising:
(i) three regions from the amino terminus of the antibody or antigen binding fragment to the carboxyl terminus: a first region of having a peptide sequence of SEQ ID NO: 91; a second region having a peptide sequence of SEQ ID NO: 92; and a third region having a peptide sequence selected from the group consisting of SEQ ID NO: 93; and
(ii) three regions from the amino terminus of the antibody or antigen binding fragment to the carboxyl terminus: a first region of having a peptide sequence of SEQ ID NO: 94; a second region having a peptide sequence of SEQ ID NO: 95; and a third region having a peptide sequence selected from the group consisting of SEQ ID NO: 96; and (h) one or more polypeptides having six regions, comprising:
(i) three regions from the amino terminus of the antibody or antigen binding fragment to the carboxyl terminus: a first region of having a peptide sequence of SEQ ID NO: 97; a second region having a peptide sequence of SEQ ID NO: 98; and a third region having a peptide sequence selected from the group consisting of SEQ ID NO: 99; and
(ii) three regions from the amino terminus of the antibody or antigen binding fragment to the carboxyl terminus: a first region of having a peptide sequence of SEQ ID NO: 100; a second region having a peptide sequence of SEQ ID NO: 101; and a third region having a peptide sequence selected from the group consisting of SEQ ID NO: 102; and (i) one or more polypeptides having six regions, comprising:
(i) three regions from the amino terminus of the antibody or antigen binding fragment to the carboxyl terminus: a first region of having a peptide sequence of SEQ ID NO: 103; a second region having a peptide sequence of SEQ ID NO: 104; and a third region having a peptide sequence selected from the group consisting of SEQ ID NO: 105; and
(ii) three regions from the amino terminus of the antibody or antigen binding fragment to the carboxyl terminus: a first region of having a peptide sequence of SEQ ID NO: 106; a second region having a peptide sequence of SEQ ID NO: 107; and a third region having a peptide sequence selected from the group consisting of SEQ ID NO: 108; and (j) one or more polypeptides having six regions, comprising:
(i) three regions from the amino terminus of the antibody or antigen binding fragment to the carboxyl terminus: a first region of having a peptide sequence of SEQ ID NO: 109; a second region having a peptide sequence of SEQ ID NO: 110; and a third region having a peptide sequence selected from the group consisting of SEQ ID NO: 111; and (ii) three regions from the amino terminus of the antibody or antigen binding fragment to the carboxyl terminus: a first region of having a peptide sequence of SEQ ID NO: 112; a second region having a peptide sequence of SEQ ID NO: 113; and a third region having a peptide sequence selected from the group consisting of SEQ ID NO: 114; and (k) one or more polypeptides having six regions, comprising:
 (i) three regions from the amino terminus of the antibody or antigen binding fragment to the carboxyl terminus: a first region of having a peptide sequence of SEQ ID NO: 115; a second region having a peptide sequence of SEQ ID NO: 116; and a third region having a peptide sequence selected from the group consisting of SEQ ID NO: 117; and
 (ii) three regions from the amino terminus of the antibody or antigen binding fragment to the carboxyl terminus: a first region of having a peptide sequence of SEQ ID NO: 118; a second region having a peptide sequence of SEQ ID NO: 119; and a third region having a peptide sequence selected from the group consisting of SEQ ID NO: 120; and one or more polypeptides having six regions, comprising:
 (i) three regions from the amino terminus of the antibody or antigen binding fragment to the carboxyl terminus: a first region of having a peptide sequence of SEQ ID NO: 121; a second region having a peptide sequence of SEQ ID NO: 122; and a third region having a peptide sequence selected from the group consisting of SEQ ID NO: 123; and
 (ii) three regions from the amino terminus of the antibody or antigen binding fragment to the carboxyl terminus: a first region of having a peptide sequence of SEQ ID NO: 124; a second region having a peptide sequence of SEQ ID NO: 125; and a third region having a peptide sequence selected from the group consisting of SEQ ID NO: 126; and (m) one or more polypeptides having six regions, comprising:
 (i) three regions from the amino terminus of the antibody or antigen binding fragment to the carboxyl terminus: a first region of having a peptide sequence of SEQ ID NO: 127; a second region having a peptide sequence of SEQ ID NO: 128; and a third region having a peptide sequence selected from the group consisting of SEQ ID NO: 129; and
 (ii) three regions from the amino terminus of the antibody or antigen binding fragment to the carboxyl terminus: a first region of having a peptide sequence of SEQ ID NO: 130; a second region having a peptide sequence of SEQ ID NO: 131; and a third region having a peptide sequence selected from the group consisting of SEQ ID NO: 132; and (n) one or more polypeptides having six regions, comprising:
 (i) three regions from the amino terminus of the antibody or antigen binding fragment to the carboxyl terminus: a first region of having a peptide sequence of SEQ ID NO: 133; a second region having a peptide sequence of SEQ ID NO: 134; and a third region having a peptide sequence selected from the group consisting of SEQ ID NO: 135; and
 (ii) three regions from the amino terminus of the antibody or antigen binding fragment to the carboxyl terminus: a first region of having a peptide sequence of SEQ ID NO: 136; a second region having a peptide sequence of SEQ ID NO: 137; and a third region having a peptide sequence selected from the group consisting of SEQ ID NO: 138; and (o) one or more polypeptides having six regions, comprising:
 (i) three regions from the amino terminus of the antibody or antigen binding fragment to the carboxyl terminus: a first region of having a peptide sequence of SEQ ID NO: 139; a second region having a peptide sequence of SEQ ID NO: 140; and a third region having a peptide sequence selected from the group consisting of SEQ ID NO: 141; and
 (ii) three regions from the amino terminus of the antibody or antigen binding fragment to the carboxyl terminus: a first region of having a peptide sequence of SEQ ID NO: 142; a second region having a peptide sequence of SEQ ID NO: 143; and a third region having a peptide sequence selected from the group consisting of SEQ ID NO: 144; and (p) one or more polypeptides having six regions, comprising:
 (i) three regions from the amino terminus of the antibody or antigen binding fragment to the carboxyl terminus: a first region of having a peptide sequence of SEQ ID NO: 145; a second region having a peptide sequence of SEQ ID NO: 146; and a third region having a peptide sequence selected from the group consisting of SEQ ID NO: 147; and
 (ii) three regions from the amino terminus of the antibody or antigen binding fragment to the carboxyl terminus: a first region of having a peptide sequence of SEQ ID NO: 148; a second region having a peptide sequence of SEQ ID NO: 149; and a third region having a peptide sequence selected from the group consisting of SEQ ID NO: 150; and (q) one or more polypeptides having six regions, comprising:
 (i) three regions from the amino terminus of the antibody or antigen binding fragment to the carboxyl terminus: a first region of having a peptide sequence of SEQ ID NO: 151; a second region having a peptide sequence of SEQ ID NO: 152; and a third region having a peptide sequence selected from the group consisting of SEQ ID NO: 153; and
 (ii) three regions from the amino terminus of the antibody or antigen binding fragment to the carboxyl terminus: a first region of having a peptide sequence of SEQ ID NO: 154; a second region having a peptide sequence of SEQ ID NO: 155; and a third region having a peptide sequence selected from the group consisting of SEQ ID NO: 156; and (r) one or more polypeptides having six regions, comprising:
 (i) three regions from the amino terminus of the antibody or antigen binding fragment to the carboxyl terminus: a first region of having a peptide sequence of SEQ ID NO: 157; a second region having a peptide sequence of SEQ ID NO: 158; and a third region having a peptide sequence selected from the group consisting of SEQ ID NO: 159.; and
 (ii) three regions from the amino terminus of the antibody or antigen binding fragment to the carboxyl terminus: a first region of having a peptide sequence of SEQ ID NO: 160; a second region having a peptide sequence of SEQ ID NO: 161; and a third region having a peptide sequence selected from the group consisting of SEQ ID NO: 162.

2. The isolated antibody or antigen binding fragment of claim 1, wherein the increased Wnt signaling can be detected in an in vitro assay.

3. The isolated antibody or antigen binding fragment of claim 1, wherein the antibody or antigen binding fragment comprises a one or more polypeptides having peptide sequences selected from the group consisting of:
 (a) SEQ ID NO: 3 and SEQ ID NO: 4;
 (b) SEQ ID NO: 5 and SEQ ID NO: 6;
 (c) SEQ ID NO: 67 and SEQ ID NO: 68;
 (d) SEQ ID NO: 69 and SEQ ID NO: 70;
 (e) SEQ ID NO: 71 and SEQ ID NO: 72;
 (f) SEQ ID NO: 73 and SEQ ID NO: 74;
 (g) SEQ ID NO: 75 and SEQ ID NO: 76;
 (h) SEQ ID NO: 77 and SEQ ID NO: 78;
 (i) SEQ ID NO: 79 and SEQ ID NO: 80;
 (j) SEQ ID NO: 81 and SEQ ID NO: 82;
 (k) SEQ ID NO: 83 and SEQ ID NO: 84;
 (l) SEQ ID NO: 85 and SEQ ID NO: 86;
 (k) SEQ ID NO: 87 and SEQ ID NO: 88; and
 (l) SEQ ID NO: 89 and SEQ ID NO: 90.

4. The antibody or antigen binding fragment of claim 1, in a pharmaceutically acceptable carrier.

5. A method of treating a disease or other indication that will benefit from an increase in Wnt signaling, comprising: administering an antibody or antigen binding fragment of claim 1 to a subject having the disease or other indication.

6. The method of claim 5, wherein the disease or other indications that will benefit from an increase in Wnt signaling are selected from the group consisting of mucositis short bowel syndrome, bacterial translocation in the gastrointestinal mucosa, enterotoxigenic or enteropathic infectious diarrhea, celiac disease, non-tropical sprue, lactose intolerance, other conditions where dietary exposures cause blunting of the mucosal villi and malabsorption, atrophic gastritis, osteoporosis, bone fracture, metabolic disease, diabetes, neurodegenerative disease, melanoma and conditions requiring tissue regeneration, tissue repair or wound healing.

7. The method of claim 5, wherein the subject is a human subject.

8. A method of treating type II diabetes mellitus, comprising:
 administering an antibody or antigen binding fragment of claim 1 to a subject with type II diabetes mellitus:
 (a) before the administration of a dipeptidyl peptidase-4 (DPP-4) inhibitor to the subject; or
 (b) concurrent with the administration of a DPP-4 inhibitor to the subject; or
 (c) before the administration of a DPP-4 inhibitor to the subject and then concurrent with the administration of a DPP-4 inhibitor to the subject.

9. The method of claim 8, wherein the DPP-4 inhibitor is vildagliptin (Galvus®).

10. The method of claim 8, wherein the subject is a human subject.

* * * * *